(12) United States Patent
Barney et al.

(10) Patent No.: US 12,162,994 B2
(45) Date of Patent: Dec. 10, 2024

(54) BIOCOMPATIBLE HYDROGEL CAPSULES AND PROCESS FOR PREPARING SAME

(71) Applicant: SIGILON THERAPEUTICS, INC., Cambridge, MA (US)

(72) Inventors: Lauren Emily Barney, Cambridge, MA (US); Richard Heidebrecht, Somerville, MA (US); Erika Ellen Johnston, Cambridge, MA (US); Robert James Miller, East Bridgewater, MA (US)

(73) Assignee: SIGILON THERAPEUTICS, INC., Cambridge, MA (US)

( * ) Notice: Subject to any disclaimer, the term of this patent is extended or adjusted under 35 U.S.C. 154(b) by 1023 days.

(21) Appl. No.: 16/977,735

(22) PCT Filed: Mar. 1, 2019

(86) PCT No.: PCT/US2019/020248
§ 371 (c)(1),
(2) Date: Sep. 2, 2020

(87) PCT Pub. No.: WO2019/169245
PCT Pub. Date: Sep. 6, 2019

(65) Prior Publication Data
US 2021/0002433 A1 Jan. 7, 2021

Related U.S. Application Data

(60) Provisional application No. 62/637,803, filed on Mar. 2, 2018.

(51) Int. Cl.
| | | |
|---|---|---|
| *A61K 9/50* | (2006.01) | |
| *C08J 3/075* | (2006.01) | |
| *C08J 3/20* | (2006.01) | |
| *C08J 3/24* | (2006.01) | |
| *C08K 3/16* | (2006.01) | |

(52) U.S. Cl.
CPC .............. *C08J 3/075* (2013.01); *C08J 3/203* (2013.01); *C08J 3/245* (2013.01); *C08K 3/16* (2013.01); *A61K 9/5036* (2013.01); *C08J 2305/04* (2013.01); *C08K 2003/162* (2013.01)

(58) Field of Classification Search
CPC .................................................. C08J 2305/04
See application file for complete search history.

(56) References Cited

U.S. PATENT DOCUMENTS

| | | |
|---|---|---|
| 4,784,950 A | 11/1988 | Hagen et al. |
| 6,361,771 B1 | 3/2002 | Tao et al. |
| 6,533,819 B1 | 3/2003 | Urry et al. |
| 8,741,340 B2 | 6/2014 | Kusk et al. |
| 9,121,037 B2 | 9/2015 | Kusk et al. |
| 9,422,373 B2 | 8/2016 | Vegas et al. |
| 9,555,007 B2 | 1/2017 | Ma et al. |
| 9,867,781 B2 | 1/2018 | Anderson et al. |
| 9,925,219 B2 | 3/2018 | Kauper et al. |
| 10,172,791 B2 | 1/2019 | Ma et al. |
| 10,278,922 B2 | 5/2019 | Anderson et al. |
| 10,285,949 B2 | 5/2019 | Vegas et al. |
| 10,292,936 B2 | 5/2019 | Vegas et al. |
| 10,426,735 B2 | 10/2019 | Vegas et al. |
| 2008/0076174 A1 | 3/2008 | Selden et al. |
| 2013/0259924 A1 | 10/2013 | Bancel et al. |
| 2014/0010861 A1 | 1/2014 | Bancel et al. |
| 2014/0271843 A1 | 9/2014 | Ma et al. |
| 2016/0030359 A1 | 2/2016 | Ma et al. |
| 2016/0030360 A1 | 2/2016 | Vegas et al. |
| 2016/0207978 A1 | 7/2016 | Kelly |
| 2017/0226232 A1 | 8/2017 | Vegas et al. |
| 2017/0260516 A1 | 9/2017 | Tan et al. |
| 2018/0318612 A1 | 11/2018 | Tzahor et al. |
| 2019/0000932 A1 | 1/2019 | Martini et al. |

FOREIGN PATENT DOCUMENTS

| | | | |
|---|---|---|---|
| CN | 104072478 A | 10/2014 | |
| CN | 106795225 A | 5/2017 | |
| JP | 2004-532234 A | 10/2004 | |
| JP | 5725475 B2 | 5/2015 | |
| JP | 2016-516020 A | 6/2016 | |
| JP | 2016-517879 A | 6/2016 | |
| JP | 2017-524768 A | 8/2017 | |
| WO | WO-2004064971 A2 * | 8/2004 | .............. B01J 13/04 |
| WO | 2008/021388 A1 | 2/2008 | |
| WO | 2008/036308 A2 | 3/2008 | |
| WO | 2010/005533 A2 | 1/2010 | |
| WO | 2012/112982 A2 | 8/2012 | |
| WO | 2012/167223 A1 | 12/2012 | |

(Continued)

OTHER PUBLICATIONS

Mettler et al., "Poloxamer 188 as a Supplement to Barium Cross-Linked Ultra-High Viscosity Alginate for Immunoisolation of Transplanted Islet Cells", 2015, Metabolomics, 5:4 (Year: 2015).*
Bremond et al., "Formation of liquid-core capsules having a thin hydrogel membrane: liquid pearls" Soft Matter, 2010, vol. 6, No. 11, pp. 2484-2488.
Veiseh et al., "Size- and shape-dependent foreign body immune response to materials implanted in rodents and non-human primates" Nature Materials, 2015, vol. 14, pp. 643-652.
Lee et al., "Size and shape of calcium alginate beads produced by extrusion dripping" Chemical Engineering and Technology, 2013, vol. 36, No. 10, pp. 1627-1642.
Vegas et al., "Combinatorial hydrogel library enables identification of materials that mitigate the foreign body response in primates" Nature Biotechnology, 2016, vol. 34, No. 3, pp. 345-352.
International Search Report and Written Opinion for Application No. PCT/US2019/020248 mailed Jun. 26, 2019.
International Search Report and Written Opinion for Application No. PCT/US2019/020405 mailed Jul. 15, 2019.

(Continued)

*Primary Examiner* — Melissa A Rioja
(74) *Attorney, Agent, or Firm* — Lando & Anastasi, LLP

(57) ABSTRACT

Described herein are compositions and methods for preparing hydrogel capsules using a cross-linking solution comprising a process additive. The process additive improves the quality of the resulting hydrogel capsules, such as increasing the number of defect-free capsules.

14 Claims, 9 Drawing Sheets
Specification includes a Sequence Listing.

(56) References Cited

FOREIGN PATENT DOCUMENTS

| | | | |
|---|---|---|---|
| WO | 2014/147386 A1 | 9/2014 |
| WO | 2014/153126 A1 | 9/2014 |
| WO | 2015/143418 A2 | 9/2015 |
| WO | 2016/019391 A1 | 2/2016 |
| WO | 2016/187225 A1 | 11/2016 |
| WO | 2017/018086 A1 | 2/2017 |
| WO | 2017/075630 A1 | 5/2017 |
| WO | 2017/075631 A1 | 5/2017 |
| WO | 2017/136358 A1 | 8/2017 |
| WO | 2018/067615 A1 | 4/2018 |
| WO | 2018/206168 A1 | 11/2018 |
| WO | 2019/067766 A1 | 4/2019 |
| WO | 2019/195056 A1 | 10/2019 |

OTHER PUBLICATIONS

International Search Report and Written Opinion for Application No. PCT/US2018/053191 mailed Mar. 5, 2019.
Sieving et al., "Ciliary neurotrophic factor (CNTF) for human retinal degeneration: Phase I trial of CNTF delivered by encapsulated cell intraocular implants" Proceedings of the National Academy of Sciences, 2006, vol. 103, No. 10, pp. 3896-3901.
Shintani et al., "Review and update: Current treatment trends for patients with retinitis pigmentosa" Optometry, 2009, vol. 80, No. 7, pp. 384-401.
Wikstrom et al., "Alginate-based microencapsulation of retinal pigment epithelial cell line for cell therapy" Biomaterials, 2008, vol. 29, pp. 869-876.
Carvalho et al., "'Click Chemistry' synthesis of a library of 1,2,3-triazole-substituted galactose derivatives and their evaluation against Trypanosoma cruzi and its cell surface trans-sialidase," Bioorganic & Medicinal Chemistry, vol. 18, No. 7, pp. 2412-2427, (2010).
Corbel et al., "Identification of potential cellular targets of aloisine A by affinity chromatography," Bioorganic & Medicinal Chemistry, vol. 17, No. 15, pp. 5572-5582, (2009).
Struthers et al., "'Click-to-Chelate': Design and Incorporation of Triazole-containing Metal-chelating Systems into Biomolecules of Diagnostic and Therapeutic Interest," Chemistry—A European Journal, vol. 14, No. 20, pp. 6173-6183, (2008).
International Search Report and Written Opinion for PCT/US2017/055001 mailed Nov. 27, 2017.
Arunrungvichian et al., "Selectivity optimization of substituted 1,2,3-Triazoles as a7 nicotinic acetylcholine receptor agonists" ACS Chemical Neuroscience, vol. 6, No. 8, 2015, pp. 1317-1330.
RN:1545351-08-3, Database Registry [Online], Retrieved from STN, Feb. 16, 2014.
Panda et al., "A nucleus-imaging probe that selectively stabilizes a minor conformation of c-MYC G-quadruplex and Down-regulates c-MYC Transcription in Human Cancer Cells" Scienctific Reports, 2015, vol. 5, pp. 1-16.
Bochenek et al., "Alginate encapsulation as long-term immune protection of allogeneic pancreatic islet cells transplanted into the omental bursa of macaques" Nature Biomedical Engineering, 2018, vol. 2, No. 11, pp. 810-821.
Vegas et al., "Long-term glycemic control using polymer-encapsulated human stem cell-derived beta cells in immune- competent mice" Nature Medicine, 2016, vol. 22, No. 3, pp. 306-311.
International Search Report and Written Opinion for Application No. PCT/US2019/024385 mailed Aug. 7, 2019.
International Search Report and Written Opinion for Application No. PCT/US2019/024371 mailed Aug. 14, 2019.
Llacua et al., "Extracellular matrix molecules and their potential contribution to the function of transplanted pancreatic islets" Diabetologia, 2018, vol. 61, pp. 1261-1272.
Llacua et al., "Laminin and collagen IV inclusion in immunoisolating microcapsules reduces cytokine-mediated cell death in human pancreatic islets" Journal of Tissue Engineering and Regenerative Medicine, 2017, 25 pages.
Orive et al., "Engineering a clinically translatable bioartificial pancreas to treat type I diabetes" Trends in Biotechnology, 2018, 12 pages.
Llacua et al., "Extracellular matrix components supporting human islet function in alginate-based immunoprotective microcapsules for treatment of diabetes" Journal of Biomedical Materials Research Part A, 2018, 10 pages.
Bochenek et al., "Alginate encapsulation as long-term immune protection of allogeneic pancreatic islet cells transplanted into the omental bursa of macaques" Nature Biomedical Engineering, vol. 2, No. 11, pp. 810-821, 2018.
Belhaj, "Enhancements in alginate microencapsulation technology & impacts on cell therapy development", Disseration, Jan. 2018 (109 pages).
Weber et al., "Multifunctional pancreatic islet encapsulation barriers achieved via multilayer PEG hydrogels", Cell Transplantation, vol. 16, No. 10, pp. 1049-1057, 2007.
Jeon et al., "Biodegradable, photocrosslinked alginate hydrogels with independently tailorable physical properties and cell adhesivity", Tissue Engineering, vol. 16, No. 9, pp. 2915-2925, 2010.
International Search Report and Written Opinion for Application No. PCT/US2019/053637 mailed Feb. 14, 2020.
International Search Report and Written Opinion for Application No. PCT/2020/02585 mailed Aug. 28, 2020.
International Search Report and Written Opinion for Application No. PCT/2020/025511 mailed Aug. 28, 2020.
Mettler et al., "Poloxamer 188 as a supplement to barium cross-linked ultra-high viscosity alginate for immunoisolation of transplanted islet cells" Metabolomics, 2015, vol. 5, Issue 4, 5 pages.

* cited by examiner

SEQ ID NO: 1

*MQIELSTCFFLCLLRFCF*SATRRYYLGAVELSWDYMQSDLGELPVDARFPPRVPKSFPFN
TSVVYKKTLFVEFTDHLFNIAKPRPPWMGLLGPTIQAEVYDTVVITLKNMASHPVSLHAV
GVSYWKASEGAEYDDQTSQREKEDDKVFPGGSHTYVWQVLKENGPMASDPLCLTYSYLSH
VDLVKDLNSGLIGALLVCREGSLAKEKTQTLHKFILLFAVFDEGKSWHSETKNSLMQDRD
AASARAWPKMHTVNGYVNRSLPGLIGCHRKSVYWHVIGMGTTPEVHSIFLEGHTFLVRNH
RQASLEISPITFLTAQTLLMDLGQFLLFCHISSHQHDGMEAYVKVDSCPEEPQLRMKNNE
EAEDYDDDLTDSEMDVVRFDDDNSPSFIQIRSVAKKHPKTWVHYIAAEEEDWDYAPLVLA
PDDRSYKSQYLNNGPQRIGRKYKKVRFMAYTDETFKTREAIQHESGILGPLLYGEVGDTL
LIIFKNQASRPYNIYPHGITDVRPLYSRRLPKGVKHLKDFPILPGEIFKYKWTVTVEDGP
TKSDPRCLTRYYSSFVNMERDLASGLIGPLLICYKESVDQRGNQIMSDKRNVILFSVFDE
NRSWYLTENIQRFLPNPAGVQLEDPEFQASNIMHSINGYVFDSLQLSVCLHEVAYWYILS
IGAQTDFLSVFFSGYTFKHKMVYEDTLTLFPFSGETVFMSMENPGLWILGCHNSDFRNRG
MTALLKVSSCDKNTGDYYEDSYEDISAYLLSKNNAIEPRSFSQNPPVLKRHQREITRTTL
QSDQEEIDYDDTISVEMKKEDFDIYDEDENQSPRSFQKKTRHYFIAAVERLWDYGMSSSP
HVLRNRAQSGSVPQFKKVVFQEFTDGSFTQPLYRGELNEHLGLLGPYIRAEVEDNIMVTF
RNQASRPYSFYSSLISYEEDQRQGAEPRKNFVKPNETKTYFWKVQHHMAPTKDEFDCKAW
AYFSDVDLEKDVHSGLIGPLLVCHTNTLNPAHGRQVTVQEFALFFTIFDETKSWYFTENM
ERNCRAPCNIQMEDPTFKENYRFHAINGYIMDTLPGLVMAQDQRIRWYLLSMGSNENIHS
IHFSGHVFTVRKKEEYKMALYNLYPGVFETVEMLPSKAGIWRVECLIGEHLAGMSTLFL
VYSNKCQTPLGMASGHIRDFQITASGQYGQWAPKLARLHYSGSINAWSTKEPFSWIKVDL
LAPMIIHGIKTQGARQKFSSLYISQFIIMYSLDGKKWQTYRGNSTGTLMVFFGNVDSSGI
KHNIFNPPIIARYIRLHPTHYSIRSTLRMELMGCDLNSCSMPLGMESKAISDAQITASSY
FTNMFATWSPSKARLHLQGRSNAWRPQVNNPKEWLQVDFQKTMKVTGVTTQGVKSLLTSM
YVKEFLISSSQDGHQWTLFFQNGKVKVFQGNQDSFTPVVNSLDPPLLTRYLRIHPQSWVH
QIALRMEVLGCEAQDLY

FIG. 9

```
SEQ ID NO: 2
YNSGKLEEFVQGNLERECMEEKCSFEEAREVFENTERTTEFWKQYVDGDQCESN
PCLNGGSCKDDINSYECWCPFGFEGKNCELDVTCNIKNGRCEQFCKNSADNKVV
CSCTEGYRLAENQKSCEPAVPFPCGRVSVSQTSKLTRAETVFPDVDYVNSTEAE
TILDNITQSTQSFNDFTRVVGGEDAKPGQFPWQVVLNGKVDAFCGGSIVNEKWI
VTAAHCVETGVKITVVAGEHNIEETEHTEQKRNVIRIIPHHNYNAAINKYNHDI
ALLELDEPLVLNSYVTPICIADKEYTNIFLKFGSGYVSGWGRVFHKGRSALVLQ
YLRVPLVDRATCLRSTKFTIYNNMFCAGFHEGGRDSCQGDSGGPHVTEVEGTSF
LTGIISWGEECAMKGKYGIYTKVSRYVNWIKEKTKLT
```

FIG. 10

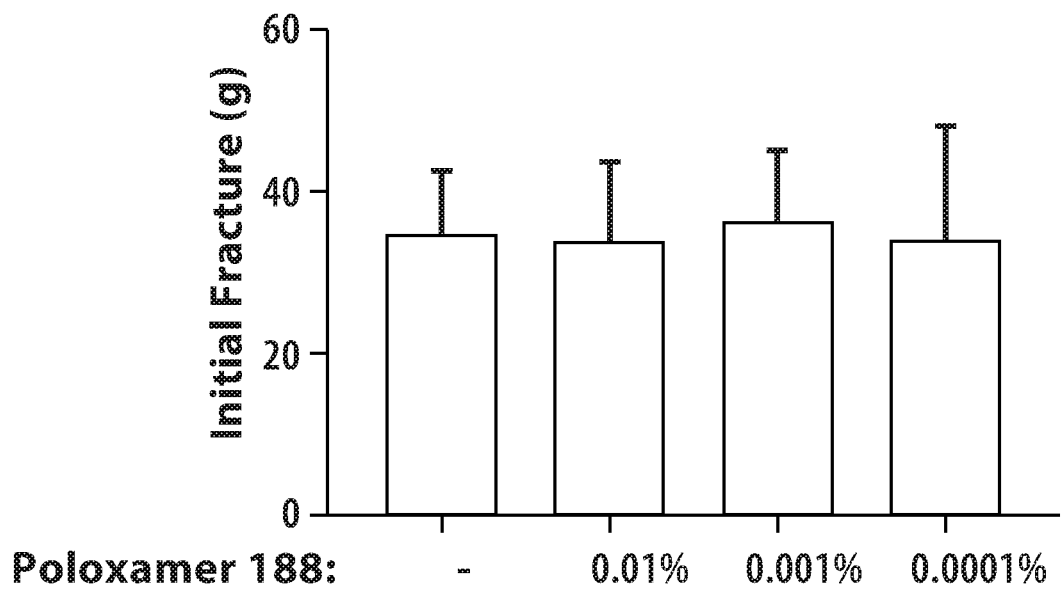

FIG. 11

BIOCOMPATIBLE HYDROGEL CAPSULES AND PROCESS FOR PREPARING SAME

CLAIM OF PRIORITY

This application is a U.S. national phase application and claims the benefit of priority under 35 U.S.C § 371 of International Application No. PCT/US2019/020248, filed on Mar. 1, 2019, which claims priority to U.S. Provisional Application No. 62/637,803, filed Mar. 2, 2018. The disclosure of each of the foregoing applications is incorporated herein by reference in its entirety.

BACKGROUND

Capsules prepared with hydrogel-forming polymers and encapsulating therapeutic or diagnostic agents have been proposed for use as implantable medical devices to treat various diseases in humans (see, e.g., U.S. Pat. Nos. 9,867, 78 and 9,555,007). The performance of such a device after implant will depend to a large extent on its biocompatibility, including the degree to which the device is afibrotic, e.g., avoids or mitigates the foreign-body response. Several publications have reported that the foreign body response (FBR) to implanted hydrogel capsules in rodents and non-human primates can be significantly reduced by using spherical capsules that have a size of at least 1 mm in diameter, e.g., millicapsules (Vesieh, O., et al, *Nature Materials* 14:643-652 (2015); WO2014/153126; WO2016/187225) and/or that are prepared using hydrogel-forming polymers that are chemically modified with certain compounds that mitigate the FBR (referred to herein as an afibrotic compound) (Vegas, A., et al., *Nature Medicine* 22(3):306-311 (2016), Vegas, A., et al., *Nature Biotechnology* 34(3):345-352 (2016); WO 2012/167223; WO 2017/075631). A need exists to develop robust processes that will facilitate commercial-scale manufacturing of hydrogel capsules encapsulating cells for use in implantable medical devices.

SUMMARY

A process for forming hydrogel capsules comprising an afibrotic alginate (e.g., an alginate chemically modified with an afibrotic compound) has been described in the art. The process uses an electrostatic droplet generator to form multiple droplets of a desired volume from a solution comprising a mixture of the afibrotic alginate and an unmodified alginate and then contacting the droplets with a cross-linking solution comprising multivalent cations to cross-link each droplet into a capsule.

The invention described herein is based on a surprising discovery: the number of defect-free spherical hydrogel capsules is significantly increased when a process additive (e.g., a surfactant) is added to the cross-linking solution. Inclusion of a process additive in the cross-linking solution may be useful, for example, during the preparation of a manufacturing batch of hydrogel capsules, or when using alginate solutions that have a wide range of viscosities (from 21.3 cP to at least 925.5 cP), or when using afibrotic alginates or unmodified alginates of different purity levels. Use of this process additive in the cross-linking solution provides another unexpected benefit for encapsulating cells: the hydrogel capsules generated in the presence of the additive have a significantly higher cell loading capacity for multiple cell types than when the same process is performed without the additive (e.g., at least a 10-fold increase for retinal pigment epithelial cells (e.g., ARPE-19 cells, ATCC® CRL-2302™) when provided as a single cell suspension). Also, one of these process additives, poloxamer 188, surprisingly generates spherical hydrogel capsules having smooth surfaces. A spherical capsule with a smooth surface may induce a lower amount of foreign body response (FBR) after implant than a spherical capsule of the same composition and size but with a rough surface, e.g., a surface with one or more ridges.

Thus, the present invention provides a process for preparing a hydrogel capsule composition from a polymer solution which comprises at least one afibrotic hydrogel-forming polymer (e.g., a polymer chemically modified with an afibrotic compound) and optionally an unmodified hydrogel-forming polymer (e.g., a polymer that has not been chemically modified with an afibrotic compound). The process comprises contacting a plurality of droplets of the polymer solution with an aqueous cross-linking solution which comprises a cross-linking agent, a buffer, an osmolarity-adjusting agent and a process additive. In an embodiment, at least 95% of the hydrogel capsules in the composition produced by the process are spherical capsules, e.g., as defined herein.

In an embodiment, the process additive is a surfactant. In an embodiment, the process additive is an amphiphilic compound. In an embodiment, the process may reduce the surface tension of the cross-linking solution.

In an embodiment, the process additive is a compound that has one or more properties of the surfactants listed in Table 1 herein. In some embodiments, the process additive comprises a surfactant. In some embodiments, the surfactant is a non-ionic surfactant. In some embodiments, the non-ionic surfactant is a polysorbate-type surfactant, e.g., Tween® 80 (Millipore Sigma). In some embodiments, the surfactant is a hydrophilic surfactant. In some embodiments, the hydrophilic surfactant is a copolymer of polyethylene oxide (PEO) and polypropylene oxide (PPO). In some embodiments, the hydrophilic surfactant is a polyethylene oxide-polypropylene oxide-polyethylene oxide (PEO-PPO-PEO) triblock copolymer, e.g., and has a hydrophilic-lipophilic balance (HLB) of at least 18 or at least 24. In an embodiment, the surfactant is selected from the group of surfactants listed in Table 1 herein. In an embodiment, the surfactant is poloxamer 188.

In some embodiments, the process additive (e.g., surfactant) is present in the cross-linking solution at a concentration of at least 0.0001% or more. In some embodiments, the cross-linking solution comprises at least 0.001%, 0.01%, or 0.1% of the process additive. In some embodiments, the process additive is present at a concentration selected from the group consisting of: about 0.001% to about 0.1%, about 0.005% to about 0.05%, about 0.005% to about 0.01%, and about 0.01% to about 0.5%. In an embodiment, the process additive is a surfactant and is present at a concentration that is below the critical micelle concentration for the surfactant.

In some embodiments, the cross-linking agent comprises divalent cations of a single type or a mixture of different types, e.g., one or more of $Ba^{2+}$, $Ca^{2+}$, $Sr^{2+}$. In some embodiments, the cross-linking agent is $BaCl_2$, e.g., at a concentration of 1 mM to 100 mM or 7.5 mM to 20 mM. In some embodiments, the cross-linking agent is $CaCl_2$, e.g., at a concentration of 50 mM to 100 mM. In some embodiments, the cross-linking agent is $SrCl_2$, e.g., at a concentration of 37.5 mM to 12.5 mM In some embodiments, the cross-linking agent is $SrCl_2$, e.g., at a concentration of 37.5 mM to 100 mM. In some embodiments, the cross-linking agent is a mixture of $BaCl_2$ (e.g., 5 mM to 20 mM) and CaCl$_2$)(e.g., 37.5 mM to 12.5 mM) or a mixture of BaCl$_2$ (e.g., 5 mM to 20 mM) and SrCl$_2$ (e.g., 37.5 mM to 12.5 mM).

In some embodiments, the cross-linking agent is SrCl$_2$, and the process additive is polysorbate 80 at a concentration of less than 0.1%, e.g., about 0.005% to 0.05%, about 0.005% to about 0.01%. In some embodiments, the concentration of SrCl$_2$ is about 50 mM. In some embodiments, the cross-linking agent is SrCl$_2$ and the process additive is poloxamer 188 at a concentration of 1%.

The type and concentration of buffer in the aqueous cross-linking solution is selected to maintain the solution pH at approximately neutral, e.g., from about 6.5 to about 7.5, about 7.0 to about 7.5, or about 7.0. In an embodiment, the buffer is compatible with a biological material to be encapsulated in the capsule, e.g., a cell. In some embodiments, the buffer in the aqueous cross-linking solution comprises HEPES (4-(2-hydroxyethyl)-1-piperazineethanesulfonic acid).

The osmolarity-adjusting agent in the aqueous cross-linking solution is selected to maintain the solution osmolarity at a value similar to the osmolarity of the polymer solution (which in some embodiments comprises a suspension of cells), e.g., an osmolarity that has a higher or lower variance of up to 20%, 10% or 5%. In some embodiments, the osmolarity agent is mannitol at a concentration of 0.1 M to 0.3 M.

In some embodiments, the afibrotic polymer comprises an afibrotic compound of Formula (I) or a salt thereof (e.g., Formulas (I-a), (II), (II-b), (II-c), (II-d), (III), (III-a), (IV), (IV-a), or (IV-b)) as described herein. In some embodiments, the afibrotic compound is a Compound shown in Table 2 herein. In some embodiments, the afibrotic compound is Compound No. 100 shown in Table 2 herein. In some embodiments, the afibrotic compound is Compound No. 101 shown in Table 2 herein. In some embodiments, the afibrotic compound is Compound No. 102 shown in Table 2 herein. In some embodiments, the afibrotic compound is other than Compound Nos. 100, 101, and 102 shown in Table 2 herein.

In some embodiments, the afibrotic polymer comprises a low molecular weight alginate (e.g., less than 75 kD) that is chemically modified with an afibrotic compound. In some embodiments, one of the afibrotic polymers and unmodified polymers (if present) in the polymer solution comprises an alginate. In some embodiments, the polymer solution comprises a mixture of an afibrotic alginate and an unmodified alginate in a saline solution, e.g., 0.8% to 1.0% saline or about 0.9%. In some embodiments, the viscosity of the alginate solution (e.g., a solution comprising afibrotic alginate but no unmodified alginate or a solution comprising a mixture of afibrotic and unmodified alginate) is 21.3 cP to 925.5 cP. In some embodiments, the unmodified alginate has a molecular weight that is higher than the alginate in the afibrotic alginate, and in some embodiments, the higher molecular weight is 150-250 kD. In an embodiment, the unmodified alginate had a molecular weight of greater than 100 kD (e.g., about 150 to about 250 kD) and the afibrotic alginate has a molecular weight of less than 100 kD (e.g., less than 75 kD).

In some embodiments of the process, the polymer solution further comprises a suspension of cells, which may be provided as single cells, cell clusters (e.g., as spheroids), or cells attached to microcarriers. In some embodiments, the concentration of single cells in the polymer solution is at least any of 5, 10, 15, 20, 30, 40, 50, 75 or 100 million cells/ml or any number between these values. In some embodiments, the cells in the suspension are engineered cells, e.g., engineered RPE cells, that express a therapeutic protein.

In some embodiments of the process, at least 90%, 95% or 99% of the droplets in the plurality of droplets have an approximately equal volume that is selected to produce a hydrogel millicapsule of a desired size, e.g., a sphere having a diameter of at least 1 millimeters (mm) and up to 5 mm. In some embodiments the desired diameter of the hydrogel millicapsule is 1 mm to about 3 mm, 1 mm to about 2 mm, or about 1.5 mm.

In some embodiments of the process, at least 90%, 95% or 99% of the droplets in the plurality of droplets have an approximately equal volume that is selected to produce a hydrogel microcapsule of a desired size, e.g., a sphere having a diameter of at least 250 micrometers (μm) to less than 1 millimeter (mm), e.g., at least 300 (μm), 500 μm, 700 (μm) or 900 (μm).

In some embodiments, the process further comprises separating the hydrogel capsules from the cross-linking solution and washing the separated hydrogel capsules one or more times in a buffered aqueous solution. In some embodiments, the wash solution comprises HEPES and one or more additional salts (e.g., NaCl, KCl, MgCl$_2$). In some embodiments, the hydrogel capsules are stored in the buffered aqueous solution at 4° C. In some embodiments, hydrogel capsules encapsulating cells are stored in culture medium at 37° C.

The present invention provides a composition produced by any of the process embodiments described above or elsewhere herein. In some embodiments, the composition is characterized by having a population of hydrogel capsules in which less than 10%, less than 5%, less than 2% or less than 1% of the capsules in the population have a capsule defect, as defined herein. In some embodiments, at least 95%, at least 98% or at least 99% of the capsules in the composition are spherical capsules having a diameter that is within about 20% of the desired size, e.g., between 1.2 and 1.8 diameter for a 1.5 ml millicapsule, or within about 15% of the desired size, e.g., between 1.35 and 1.65 diameter for a 1.5 millicapsule. In some embodiments, the composition comprises 220 spherical hydrogel capsules of the desired size per ml. In some embodiments, the composition is characterized as comprising a detectable amount of the process additive. In some embodiments, each of the hydrogel millicapsules in the composition encapsulate 500 to 20,000 cells (e.g., engineered RPE cells). In some embodiments, each of the hydrogel millicapsules in the composition encapsulate at least 20,000 cells, at least 25,000 cells, or at least 30,000 to 50,000 cells.

In yet another aspect, the present invention provides a composition comprising spherical hydrogel capsules encapsulating cells, wherein the hydrogel capsules comprise an afibrotic polymer in the hydrogel and at least 95%, 97% or at least 99% of the capsules are spherical and each of the spherical capsules contains at least about 100, 250, 500, 750, 1,000, 2,500, 5,000, 7,500, or 10,000 cells (e.g., engineered RPE cells). In an embodiment, all the capsules in the composition comprise a smooth surface. In an embodiment, the composition is formulated for administration to a human subject. In an embodiment, the composition comprises a medical device intended for implant into a human subject. In an embodiment, the composition further comprises a surfactant. In an embodiment, molecules of the surfactant are disposed on or within the surface of the hydrogel capsules. In an embodiment, the surfactant comprises poloxamer 188.

The details of one or more embodiments of the invention are set forth herein. Other features, objects, and advantages of the invention will be apparent from the Detailed Description, the Figures, the Examples, and the Claims.

BRIEF DESCRIPTION OF THE DRAWINGS

FIG. 9 shows the amino acid sequence (SEQ ID NO:1) of a Factor VIII-BDD protein encoded by an exemplary engineered cell.

FIG. 10 shows the amino acid sequence (SEQ ID NO:2) of a human wild-type Factor IX protein.

FIG. 11 is a bar graph that illustrates the effect of various concentrations of poloxamer 188 in the barium chloride cross-linking solution on capsule strength in a composition comprising empty alginate hydrogel milllicapsules (about 1.5 mm in diameter) as assessed by initial fracture ex vivo.

DETAILED DESCRIPTION

Figure 1A:
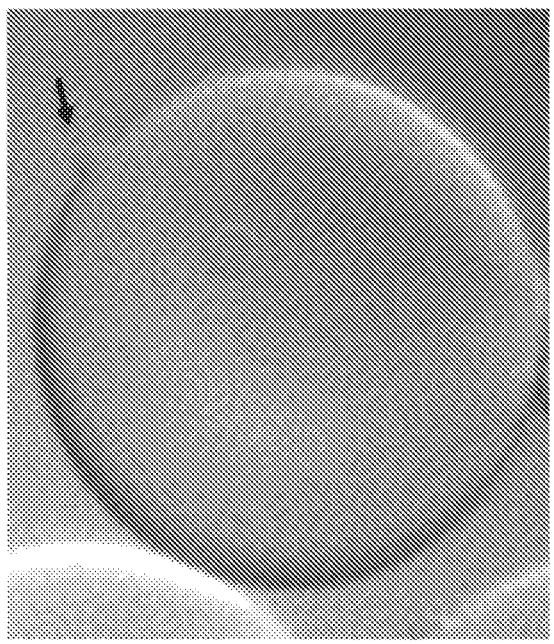
FIGS. 1A-1B are representative bright field images of two types of capsule composition defects that are frequently seen when an afibrotic alginate droplet is cross-linked with barium chloride in the absence of a hydrophilic surfactant, with the FIG. 1A showing a spherical hydrogel capsule with a protuberance (indicated by the arrow) and FIG. 1B showing non-capsular debris, e.g., a non-spherical entity with a large tail (indicated by the arrow).

The present invention features a process for preparing spherical hydrogel capsules from afibrotic hydrogel-forming polymers which comprises cross-linking droplets of a hydrogel forming polymer in the presence of a process additive (e.g., hydrophilic surfactant) as well as compositions produced by the process. The process described herein provides is robust and can facilitate commercial-scale manufacturing of afibrotic compositions and devices comprising the spherical hydrogel capsules.

Definitions

So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

"About", when used herein to modify a numerically defined parameter (e.g., a physical description of a hydrogel capsule such as diameter, sphericity, number of encapsulated cells, the concentration of a component in the cross-linking solution), means that the parameter may vary by as much as 10% above or below the stated numerical value for that parameter. For example, a hydrogel capsule defined as having a diameter of about 1.5 millimeters (mm) and encapsulating about 5 million (M) cells may have a diameter of 1.35 to 1.65 mm and may encapsulate about 4.5 M to 5.5 M cells. Similarly, a cross-linking solution comprising a process additive of about 0.01% may have 0.009% to 0.011%.

"Acquire" or "acquiring", as used herein, refer to obtaining possession of a value, e.g., a numerical value, or image, or a physical entity (e.g., a sample), by "directly acquiring" or "indirectly acquiring" the value or physical entity. "Directly acquiring" means performing a process (e.g., performing an analytical method or protocol) to obtain the value or physical entity. "Indirectly acquiring" refers to receiving the value or physical entity from another party or source (e.g., a third-party laboratory that directly acquired the physical entity or value). Directly acquiring a value or physical entity includes performing a process that includes a physical change in a physical substance or the use of a machine or device. Examples of directly acquiring a value include obtaining a sample from a human subject. Directly acquiring a value includes performing a process that uses a machine or device, e.g., fluorescence microscope to acquire fluorescence microscopy data.

"Administer", "administering", or "administration", as used herein, refer to implanting, absorbing, ingesting, injecting, or otherwise introducing an entity described herein (e.g., a device comprising one or more hydrogel capsules (including hydrogel capsules encapsulating cells, e.g., engineered RPE cells), a composition comprising hydrogel capsules), or providing the same to a subject.

"Afibrotic", as used herein, means a compound or material that mitigates the foreign body response (FBR). For example, the FBR induced by a hydrogel capsule comprising an afibrotic compound (e.g., a hydrogel-forming polymer chemically modified with any of the compounds listed in Table 2) implanted in a biological tissue may be lower than the FBR induced by implantation of a hydrogel capsule of substantially the same composition, size and shape that lacks the afibrotic compound. In an embodiment, the degree of the FBR is assessed by the immunological response in the tissue containing the implanted hydrogel capsule, e.g., protein adsorption, macrophages, multinucleated foreign body giant cells, fibroblasts, and angiogenesis, using assays known in the art, e.g., as described in WO 2017/075630, or using one or more of the assays/methods described Vegas, A., et al., *Nature Biotechnol* (supra), (e.g., subcutaneous cathepsin measurement of implanted capsules, Masson's trichrome (MT), hematoxylin or eosin staining of tissue sections, quantification of collagen density, cellular staining and confocal microscopy for macrophages (CD68), myfibroblasts (alpha-muscle actin, SMA) or general cellular deposition, quantification of 79 RNA sequences of known inflammation factors and immune cell markers, or FACS analysis for macrophage and neutrophil cells on retrieved capsules after 14 days in the intraperitoneal space). In an embodiment, the FBR is assessed by measuring the levels in the tissue of one or more biomarkers of immune response, e.g., cathepsin, TNF-α, IL-13, IL-6, G-CSF, GM-CSF, IL-4, CCL2, or CCL4. In some embodiments, the FBR induced by a hydrogen capsule comprising an afibrotic polymer is at least about 80%, about 85%, about 90%, about 95%, about 99%, or about 100% lower than the FBR induced by the same polymer without the afibrotic compound. In some embodiments, the FBR (e.g., level of a biomarker(s)) is measured after about 30 minutes, about 1 hour, about 6 hours, about 12 hours, about 1 day, about 2 days, about 3 days, about 4 days, about 1 week, about 2 weeks, about 1 month, about 2 months, about 3 months, about 6 months, or longer.

"Capsule Composition Defect", as used herein, means the presence of an undesirable component in a composition or preparation of hydrogel capsules, e.g., components other than spherical hydrogel capsules of the desired size, and include capsule defects, non-capsule debris and satellite capsules.

"Capsule defect", as used herein, means any physical attribute of a hydrogel capsule that contributes to a non-spherical shape and is observable under a microscope (e.g., using 2× or 4× objective), e.g., a protrusion extending from a capsule as shown in FIG. 1A. In an embodiment, a capsule defect is a protrusion extending at least about 20 to 50 microns from the capsule.

Figure 1B:
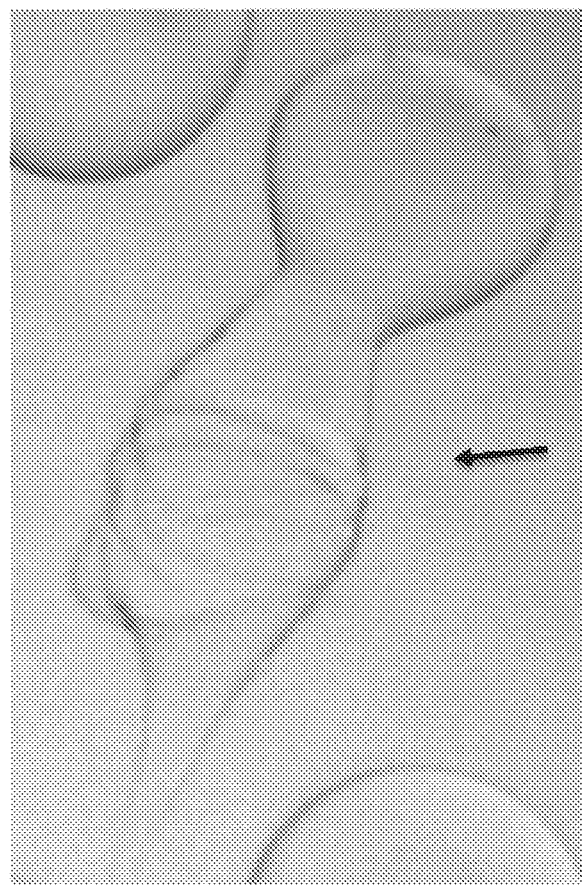

"Non-capsule debris", as used herein, means any extra-capsular entity that forms when a droplet of polymer solution contacts the cross-linking solution (e.g., a non-capsular entity with a large tail (e.g., as shown in FIG. 1B), incompletely cross-linked hydrogel, clumps of capsules cross-linked together, components of the polymer solution that did not become incorporated into a hydrogel capsule (e.g., afibrotic polymer, unmodified polymer, cells). In an embodiment, the cross-linking solution is contained in a vessel and non-capsule debris forms on the surface of the cross-linking solution.

"Satellite capsule", as used herein, means a hydrogel capsule (spherical or non-spherical) formed from a droplet that is significantly smaller than a droplet desired capsule size, e.g., at least 30%, 40% or 50% smaller than the desired capsule size. In an embodiment, the desired capsule size is a millicapsule of about 1.5 mm in diameter and a satellite capsule is less than about 500 microns in diameter.

"Cell," as used herein, refers to an engineered cell or a cell that is not engineered.

"Cell loading capacity", as used herein, reflects the ability to prepare a composition of hydrogel capsules encapsulating cells that has one or more desired quality attributes when using a high cell-loading concentration in the afibrotic hydrogel-forming polymer solution, e.g., a cell loading concentration of at least about 30, 40 or 50 million cells/ml polymer solution. In an embodiment, the desired quality attributes are low numbers of non-capsule debris and capsule defects in the cross-linking solution, e.g., the combined number of these attributes is less than about 10%, or about 5% of the total number of capsules in the composition. A capsule with more than one capsule defect is only counted once. In an embodiment, the cell loading capacity is quantified as shown in the table below:

| Cell Loading Capacity | % Combined Capsule Defects and Non-Capsule Debris |
|---|---|
| High | 0-5% |
| Moderate | >5% and up to 20% |
| Low | >20% |

"Effective amount" as used herein refers to an amount of a composition of hydrogel capsules encapsulating cells, e.g., engineered cells, or an agent, e.g., a therapeutic agent, produced by engineered cells, e.g., an engineered RPE cell, sufficient to elicit a biological response, e.g., to treat a disease, disorder, or condition. As will be appreciated by those of ordinary skill in this art, the effective amount may vary depending on such factors as the desired biological endpoint, the pharmacokinetics of the therapeutic agent, composition or implantable element, the condition being treated, the mode of administration, and the age and health of the subject. An effective amount encompasses therapeutic and prophylactic treatment. For example, to treat a fibrotic condition, an effective amount of a compound may reduce the fibrosis or stop the growth or spread of fibrotic tissue.

An "endogenous nucleic acid" as used herein, is a nucleic acid that occurs naturally in a subject cell.

An "endogenous polypeptide," as used herein, is a polypeptide that occurs naturally in a subject cell.

"Engineered cell," as used herein, is a cell (e.g., an RPE cell) having a non-naturally occurring alteration, and typically comprises a nucleic acid sequence (e.g., DNA or RNA) or a polypeptide not present (or present at a different level than) in an otherwise similar cell under similar conditions that is not engineered (an exogenous nucleic acid sequence). In an embodiment, an engineered cell comprises an exogenous nucleic acid (e.g., a vector or an altered chromosomal sequence). In an embodiment, an engineered cell comprises an exogenous polypeptide. In an embodiment, an engineered cell comprises an exogenous nucleic acid sequence, e.g., a sequence, e.g., DNA or RNA, not present in a similar cell that is not engineered. In an embodiment, the exogenous nucleic acid sequence is chromosomal, e.g., the exogenous nucleic acid sequence is an exogenous sequence disposed in endogenous chromosomal sequence. In an embodiment, the exogenous nucleic acid sequence is chromosomal or extra chromosomal, e.g., a non-integrated vector. In an embodiment, the exogenous nucleic acid sequence comprises an RNA sequence, e.g., an mRNA. In an embodiment, the exogenous nucleic acid sequence comprises a chromosomal or extra-chromosomal exogenous nucleic acid sequence that comprises a sequence which is expressed as RNA, e.g., mRNA or a regulatory RNA. In an embodiment, the exogenous nucleic acid sequence comprises a chromosomal or extra-chromosomal nucleic acid sequence, which comprises a sequence that encodes a polypeptide, or which is expressed as a polypeptide. In an embodiment, the exogenous nucleic acid sequence comprises a first chromosomal or extra-chromosomal exogenous nucleic acid sequence that modulates the conformation or expression of a second nucleic acid sequence, wherein the second amino acid sequence can be exogenous or endogenous. For example, an engineered cell can comprise an exogenous nucleic acid that controls the expression of an endogenous sequence. In an embodiment, an engineered cell comprises a polypeptide present at a level or distribution which differs from the level found in a similar cell that has not been engineered. In an embodiment, an engineered cell comprises an RPE engineered to provide an RNA or a polypeptide. For example, an engineered cell may comprise an exogenous nucleic acid sequence comprising a chromosomal or extra-chromosomal exogenous nucleic acid sequence that comprises a sequence which is expressed as RNA, e.g., mRNA or a regulatory RNA. In an embodiment, an engineered cell (e.g., an RPE cell) comprises an exogenous nucleic acid sequence that comprises a chromosomal or extra-chromosomal nucleic acid sequence comprising a sequence that encodes a polypeptide, or which is expressed as a polypeptide. In an embodiment, an engineered cell (e.g., an RPE cell) comprises an exogenous nucleic acid sequence that modulates the conformation or expression of an endogenous sequence.

An "exogenous nucleic acid," as used herein, is a nucleic acid that does not occur naturally in a subject cell.

An "exogenous polypeptide," as used herein, is polypeptide that does not occur naturally in a subject cell.

"Islet cell", as used herein means a cell that comprises any naturally occurring or any synthetically created, or modified, cell that is intended to recapitulate, mimic or otherwise express, in part or in whole, the functions, in part or in whole, of the cells of the pancreatic islets of Langerhans. The term islet cells includes glucose-responsive, insulin producing cells derived from stem cells, e.g., an induced pluripotent stem cell line.

"Mannitol", as used herein, refers to D-mannitol unless otherwise explicitly stated.

"Poloxamer", as used herein, refers to the standard generic term for a class of nonionic triblock linear copolymers composed of a central hydrophobic chain of polyoxypropylene (poly(propylene oxide)) flanked by two polyoxyethylene (poly(ethylene oxide)) moieties.

"Poloxamer 188" or "P 188", as used herein, refers to a poloxamer with an approximate molecular mass of 1800 g/mole for the polyoxypropylene core and an oxyethylene content of about 80% weight percent, e.g., 79.0 to 83.7 percent. In an embodiment, poloxamer 188 has an average molecular weight of 8350 g/mole. In an embodiment, poloxamer 188 has an average molecular weight of 7680 g/mole to 9510 g/mole, e.g., as determined by size exclusion chromatography, and an oxyethylene content of 81.8±1.9% weight percent. In an embodiment, each polyoxyethylene chain in poloxamer 188 has 75-85 (e.g., 80) ethylene oxide monomers and the polyoxypropylene core has 25-30 (e.g., 27) propylene oxide monomers. In an embodiment, poloxamer 188 used in a process described herein substantially meets the specifications set forth in a poloxamer monograph published by the United States Pharmacopia-National Formulary (USP-NF) or the European Pharmacopoeia (Ph. Eur.) that is official at the time the process is performed.

"Poloxamer 407" or "P 407", as used herein, means a poloxamer with an approximate molecular mass of 4000 g/mole for the polypropylene core and an oxyethylene content of about 70% by weight. In an embodiment, poloxamer 407 has an average molecular weight of 9,840 g/mole to 14,600 g/mole and an oxyethylene content of 73.2±1.7% by weight. In an embodiment, each polyoxyethylene chain in poloxamer 407 has 95-105 (e.g., 101) ethylene oxide monomers (e.g., and the polyoxypropylene core has 54-60 (e.g., 56) propylene oxide monomers.

"Polypeptide", as used herein, refers to a polymer comprising amino acid residues linked through peptide bonds and having at least two, and in embodiments, at least 10, 100, or 200 amino acid residues.

"Polysorbate 20", as used herein, refers to a laurate ester of sorbitol and related anhydrides, copolymerized with approximately 20 moles of ethylene oxide for each mole of sorbitol and sorbitol anhydrides. In an embodiment, polysorbate 20 has a molecular weight of 1,225 Da, assuming 20 ethylene oxide units, 1 sorbitol unit, and 1 lauric acid unit as the primary fatty acid. In an embodiment, polysorbate 80 used in a process described herein substantially meets the specifications set forth in a Polysorbate 20 monograph published by the United States Pharmacopeia-National Formulary (USP-NF) (e.g., the USP-NF monograph entitled: Interim Revision Announcement, Official Sep. 1, 2014), or a monograph published by the USP-NF or the European Pharmacopoeia (Ph. Eur.) that is official at the time the process is performed.

"Polysorbate 80", as used herein, refers to a mixture of partial esters of fatty acids, mainly oleic acid, with sorbitol and its anhydrides ethoxylated with approximately 20 moles of ethylene oxide for each mole of sorbitol and sorbitol anhydrides. In an embodiment, polysorbate 80 used in a process described herein substantially meets the specifications set forth in a Polysorbate monograph published by the United States Pharmacopeia-National Formulary (USP-NF) (e.g., the monograph entitled: Stage 6 Harmonization Revision, Official Aug. 1, 2017), or a monograph published by the USP-NF or the European Pharmacopoeia (Ph. Eur.) that is official at the time the process is performed.

"Prevention," "prevent," and "preventing" as used herein refers to a treatment that comprises administering or applying a therapy, e.g., administering a composition of hydrogel capsules encapsulating cells (e.g., as described herein), prior to the onset of a disease, disorder, or condition to preclude the physical manifestation of said disease, disorder, or condition. In some embodiments, "prevention," "prevent," and "preventing" require that signs or symptoms of the disease, disorder, or condition have not yet developed or have not yet been observed. In some embodiments, treatment comprises prevention and in other embodiments it does not.

A "replacement therapy" or "replacement protein" is a therapeutic protein or functional fragment thereof that replaces or augments a protein that is diminished, present in insufficient quantity, altered (e.g., mutated) or lacking in a subject having a disease or condition related to the diminished, altered or lacking protein. Examples are certain blood clotting factors in certain blood clotting disorders or certain lysosomal enzymes in certain lysosomal storage diseases. In an embodiment, a replacement therapy or replacement protein provides the function of an endogenous protein. In an embodiment, a or replacement therapy or replacement protein has the same amino acid sequence of a naturally occurring variant, e.g., a wild type allele or an allele not associated with a disorder, of the replaced protein. In an embodiment, or replacement therapy or a replacement protein differs in amino acid sequence from a naturally occurring variant, e.g., a wild type allele or an allele not associated with a disorder, e.g., the allele carried by a subject, at no more than about 1, 2, 3, 4, 5, 10, 15 or 20% of the amino acid residues.

"RPE cell" as used herein refers to a cell having one or more of the following characteristics: a) it comprises a retinal pigment epithelial cell (RPE) (e.g., cultured using the ARPE-19 cell line (ATCC® CRL-2302™)) or a cell derived therefrom, including a cell derived from a primary cell culture of RPE cells, a cell isolated directly (without long term culturing, e.g., less than 5 or 10 passages or rounds of cell division since isolation) from naturally occurring RPE cells, e.g., from a human or other mammal, a cell derived from a transformed, an immortalized, or a long term (e.g., more than 5 or 10 passages or rounds of cell division) RPE cell culture; b) a cell that has been obtained from a less differentiated cell, e.g., a cell developed, programmed, or reprogrammed (e.g., in vitro) into an RPE cell or a cell that is, except for any genetic engineering, substantially similar to one or more of a naturally occurring RPE cell or a cell from a primary or long term culture of RPE cells (e.g., such an active cell can be derived from an IPS cell); or c) a cell that has one or more of the following properties: i) it expresses one or more of the biomarkers CRALBP, RPE-65, RLBP, BEST1, or αB-crystallin; ii) it does not express one or more of the biomarkers CRALBP, RPE-65, RLBP, BEST1, or αB-crystallin; iii) it is naturally found in the retina and forms a monolayer above the choroidal blood vessels in the Bruch's membrane; or iv) it is responsible for epithelial transport, light absorption, secretion, and immune modulation in the retina. In an embodiment, an RPE described herein is engineered, e.g., to have a new property, e.g., the cell is engineered to express a therapeutic protein. In other embodiments, an RPE cell is not engineered.

"Spherical hydrogel capsule" as used herein, means a capsule having a curved surface that forms a sphere (e.g., a completely round ball) or sphere-like shape. Spheres and sphere-like objects can be mathematically defined by rotation of circles, ellipses, or a combination around each of the three perpendicular axes, a, b, and c. For a sphere, the three axes are the same length. Generally, a sphere-like shape is an ellipsoid (for its averaged surface) with semi-principal axes within 10%, or 5%, or 2.5% of each other. The diameter of a sphere or sphere-like shape is the average diameter, such as the average of the semi-principal axes.

"Subject" as used herein refers to a human or non-human animal. In an embodiment, the subject is a human (i.e., a male or female, e.g., of any age group, a pediatric subject (e.g., infant, child, adolescent) or adult subject (e.g., young adult, middle-aged adult, or senior adult)). In an embodiment, the subject is a non-human animal, for example, a mammal (e.g., a primate (e.g., a cynomolgus monkey or a rhesus monkey)). In an embodiment, the subject is a commercially relevant mammal (e.g., a cattle, pig, horse, sheep, goat, cat, or dog) or a bird (e.g., a commercially relevant bird such as a chicken, duck, goose, or turkey). In certain embodiments, the animal is a mammal. The animal may be a male or female and at any stage of development. A non-human animal may be a transgenic animal.

"Treatment," "treat," and "treating" as used herein refers to one or more of reducing, reversing, alleviating, delaying the onset of, or inhibiting the progress of one or more of a symptom, manifestation, or underlying cause, of a disease, disorder, or condition. In an embodiment, treating comprises reducing, reversing, alleviating, delaying the onset of, or inhibiting the progress of a symptom of a disease, disorder, or condition. In an embodiment, treating comprises reducing, reversing, alleviating, delaying the onset of, or inhibiting the progress of a manifestation of a disease, disorder, or condition. In an embodiment, treating comprises reducing, reversing, alleviating, reducing, or delaying the onset of, an underlying cause of a disease, disorder, or condition. In some embodiments, "treatment," "treat," and "treating" require that signs or symptoms of the disease, disorder, or condition have developed or have been observed. In other embodiments, treatment may be administered in the absence of signs or symptoms of the disease or condition, e.g., in preventive treatment. For example, treatment may be administered to a susceptible individual prior to the onset of symptoms (e.g., considering a history of symptoms and/or in light of genetic or other susceptibility factors). Treatment may also be continued after symptoms have resolved, for example, to delay or prevent recurrence. In some embodiments, treatment comprises prevention and in other embodiments it does not.

Selected Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

The abbreviations used herein have their conventional meaning within the chemical and biological arts. The chemical structures and formulae set forth herein are constructed according to the standard rules of chemical valency known in the chemical arts.

When a range of values is listed, it is intended to encompass each value and sub-range within the range. For example, "$C_1$-$C_6$ alkyl" is intended to encompass, $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl.

As used herein, "alkyl" refers to a radical of a straight-chain or branched saturated hydrocarbon group having from 1 to 24 carbon atoms ("$C_1$-$C_{24}$ alkyl"). In some embodiments, an alkyl group has 1 to 12 carbon atoms ("$C_1$-$C_{12}$ alkyl"), 1 to 8 carbon atoms ("$C_1$-$C_8$ alkyl"), 1 to 6 carbon atoms ("$C_1$-$C_6$ alkyl"), 1 to 5 carbon atoms ("$C_1$-$C_5$ alkyl"), 1 to 4 carbon atoms ("$C_1$-$C_4$alkyl"), 1 to 3 carbon atoms ("$C_1$-$C_3$ alkyl"), 1 to 2 carbon atoms ("$C_1$-$C_2$ alkyl"), or 1 carbon atom ("$C_1$ alkyl"). In some embodiments, an alkyl group has 2 to 6 carbon atoms ("$C_2$-$C_6$alkyl"). Examples of $C_1$-$C_6$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Each instance of an alkyl group may be independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent.

As used herein, "alkenyl" refers to a radical of a straight-chain or branched hydrocarbon group having from 2 to 24 carbon atoms, one or more carbon-carbon double bonds, and no triple bonds ("$C_2$-$C_{24}$ alkenyl"). In some embodiments, an alkenyl group has 2 to 10 carbon atoms ("$C_2$-$C_{10}$ alkenyl"), 2 to 8 carbon atoms ("$C_2$-$C_8$ alkenyl"), 2 to 6 carbon atoms ("$C_2$-$C_6$ alkenyl"), 2 to 5 carbon atoms ("$C_2$-$C_5$ alkenyl"), 2 to 4 carbon atoms ("$C_2$-$C_4$ alkenyl"), 2 to 3 carbon atoms ("$C_2$-$C_3$ alkenyl"), or 2 carbon atoms ("$C_2$ alkenyl"). The one or more carbon-carbon double bonds can be internal (such as in 2-butenyl) or terminal (such as in 1-butenyl). Examples of $C_2$-$C_4$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_2$-$C_6$ alkenyl groups include the aforementioned $C_{2-4}$ alkenyl groups as well as pentenyl ($C_5$), pentadienyl ($C_5$), hexenyl ($C_6$), and the like. Each instance of an alkenyl group may be independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent.

As used herein, the term "alkynyl" refers to a radical of a straight-chain or branched hydrocarbon group having from 2 to 24 carbon atoms, one or more carbon-carbon triple bonds ("$C_2$-$C_{24}$ alkenyl"). In some embodiments, an alkynyl group has 2 to 10 carbon atoms ("$C_2$-$C_{10}$ alkynyl"), 2 to 8 carbon atoms ("$C_2$-$C_8$ alkynyl"), 2 to 6 carbon atoms ("$C_2$-$C_6$ alkynyl"), 2 to 5 carbon atoms ("$C_2$-$C_5$ alkynyl"), 2 to 4 carbon atoms ("$C_2$-$C_4$ alkynyl"), 2 to 3 carbon atoms ("$C_2$-$C_3$ alkynyl"), or 2 carbon atoms ("$C_2$ alkynyl"). The one or more carbon-carbon triple bonds can be internal (such as in 2-butynyl) or terminal (such as in 1-butynyl). Examples of $C_2$-$C_4$ alkynyl groups include ethynyl ($C_2$), 1-propynyl ($C_3$), 2-propynyl ($C_3$), 1-butynyl ($C_4$), 2-butynyl ($C_4$), and the like. Each instance of an alkynyl group may be independently optionally substituted, i.e., unsubstituted (an "unsubstituted alkynyl") or substituted (a "substituted alkynyl") with one or more substituents e.g., for instance from 1 to 5 substituents, 1 to 3 substituents, or 1 substituent.

As used herein, the term "heteroalkyl," refers to a non-cyclic stable straight or branched alkyl chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any position of the heteroalkyl group. Exemplary heteroalkyl groups include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S($O)_2$—$CH_3$, —CH=CH—O—$CH_3$, —Si($CH_3)_3$, —$CH_2$—CH=N—O$CH_3$, —CH=CH—N($CH_3$)—$CH_3$, —O—$CH_3$, and —O—$CH_2$—$CH_3$. Up to two or three heteroatoms may be consecutive, such as, for example, —$CH_2$—NH—O$CH_3$ and —$CH_2$—O—Si($CH_3)_3$. Where "heteroalkyl" is recited, followed by recitations of specific heteroalkyl groups, such as —$CH_2$O, —$NR^CR^D$, or the like, it will be understood that the terms heteroalkyl and —$CH_2$O or —$NR^CR^D$ are not redundant or mutually exclusive. Rather, the specific heteroalkyl groups are recited to add clarity. Thus, the term "heteroalkyl" should not be interpreted herein as excluding specific heteroalkyl groups, such as —$CH_2$O, —$NR^CR^D$, or the like.

The terms "alkylene," "alkenylene," "alkynylene," or "heteroalkylene," alone or as part of another substituent, mean, unless otherwise stated, a divalent radical derived from an alkyl, alkenyl, alkynyl, or heteroalkyl, respectively. An alkylene, alkenylene, alkynylene, or heteroalkylene group may be described as, e.g., a $C_1$-$C_6$-membered alkylene, $C_1$-$C_6$-membered alkenylene, $C_1$-$C_6$-membered alkynylene, or $C_1$-$C_6$-membered heteroalkylene, wherein the term "membered" refers to the non-hydrogen atoms within the moiety. In the case of heteroalkylene groups, heteroatoms can also occupy either or both chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$C(O)_2R'$— may represent both —$C(O)_2R'$— and —R'C$(O)_2$—.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_6$-$C_{14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). An aryl group may be described as, e.g., a $C_6$-$C_{10}$-membered aryl, wherein the term "membered" refers to the non-hydrogen ring atoms within the moiety. Aryl groups include phenyl, naphthyl, indenyl, and tetrahydronaphthyl. Each instance of an aryl group may be independently optionally substituted, i.e., unsubstituted (an "unsubstituted aryl") or substituted (a "substituted aryl") with one or more substituents.

As used herein, "heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). A heteroaryl group may be described as, e.g., a 6-10-membered heteroaryl, wherein the term "membered" refers to the non-hydrogen ring atoms within the moiety.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Each instance of a heteroaryl group may be independently optionally substituted, i.e., unsubstituted (an "unsubstituted heteroaryl") or substituted (a "substituted heteroaryl") with one or more substituents.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Other exemplary heteroaryl groups include heme and heme derivatives.

As used herein, the terms "arylene" and "heteroarylene," alone or as part of another substituent, mean a divalent radical derived from an aryl and heteroaryl, respectively.

As used herein, "cycloalkyl" refers to a radical of a non-aromatic cyclic hydrocarbon group having from 3 to 10 ring carbon atoms ("$C_3$-$C_{10}$ cycloalkyl") and zero heteroatoms in the non-aromatic ring system. In some embodiments, a cycloalkyl group has 3 to 8 ring carbon atoms ("$C_3$-$C_8$cycloalkyl"), 3 to 6 ring carbon atoms ("$C_3$-$C_6$ cycloalkyl"), or 5 to 10 ring carbon atoms ("$C_5$-$C_{10}$ cycloalkyl"). A cycloalkyl group may be described as, e.g., a $C_4$-$C_7$-membered cycloalkyl, wherein the term "membered" refers to the non-hydrogen ring atoms within the moiety. Exemplary $C_3$-$C_6$ cycloalkyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl (C), and the like. Exemplary $C_3$-$C_5$ cycloalkyl groups include, without limitation, the aforementioned $C_3$-$C_6$ cycloalkyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), cubanyl ($C_8$), bicyclo[1.1.1]pentanyl ($C_5$), bicyclo[2.2.2]octanyl ($C_8$), bicyclo[2.1.1]hexanyl ($C_6$), bicyclo[3.1.1]heptanyl ($C_7$), and the like. Exemplary $C_3$-$C_{10}$ cycloalkyl groups include, without limitation, the aforementioned $C_3$-$C_8$ cycloalkyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the cycloalkyl group is either monocyclic ("monocyclic cycloalkyl") or contain a fused, bridged or spiro ring system such as a bicyclic system ("bicyclic cycloalkyl") and can be saturated or can be partially unsaturated. "Cycloalkyl" also includes ring systems wherein the cycloalkyl ring, as defined above, is fused with one or more aryl groups wherein the point of attachment is on the cycloalkyl ring, and in such instances, the number of carbons continue to designate the number of carbons in the cycloalkyl ring system. Each instance of a cycloalkyl group may be independently optionally substituted, i.e., unsubstituted (an "unsubstituted cycloalkyl") or substituted (a "substituted cycloalkyl") with one or more substituents.

"Heterocyclyl" as used herein refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more cycloalkyl groups wherein the point of attachment is either on the cycloalkyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. A heterocyclyl group may be described as, e.g., a 3-7-membered heterocyclyl, wherein the term "membered" refers to the non-hydrogen ring atoms, i.e., carbon, nitrogen, oxygen, sulfur, boron, phosphorus, and silicon, within the moiety. Each instance of heterocyclyl may be independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, piperazinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl or thiomorpholinyl-1,1-dioxide. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Amino" as used herein refers to the radical —$NR^{70}R^{71}$, wherein $R^{70}$ and $R^{71}$ are each independently hydrogen, $C_1$-$C_8$ alkyl, $C_3$-$C_{10}$ cycloalkyl, $C_4$-$C_{10}$ heterocyclyl, $C_6$-$C_{10}$ aryl, and $C_5$-$C_{10}$ heteroaryl. In some embodiments, amino refers to $NH_2$.

As used herein, "cyano" refers to the radical —CN.

As used herein, "halo" or "halogen," independently or as part of another substituent, mean, unless otherwise stated, a fluorine (F), chlorine (Cl), bromine (Br), or iodine (I) atom.

As used herein, "hydroxy" refers to the radical —OH.

Alkyl, alkenyl, alkynyl, heteroalkyl, cycloalkyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" cycloalkyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, such as any of the substituents described herein that result in the formation of a stable compound. The present invention contemplates any and all such combinations to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Two or more substituents may optionally be joined to form aryl, heteroaryl, cycloalkyl, or heterocyclyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Afibrotic compounds (e.g., compounds of Formula (I)) described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high-pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E.L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

As used herein, a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 99% by weight, more than 99.5% by weight, or more than 99.9% by weight, of the enantiomer. In certain embodiments, the weights are based upon total weight of all enantiomers or stereoisomers of the compound.

Afibrotic compounds (e.g., compounds of Formula (I)) described herein may also comprise one or more isotopic substitutions. For example, H may be in any isotopic form, including $^1$H, $^2$H (D or deuterium), and $^3$H (T or tritium); C may be in any isotopic form, including $^{12}$C, $^{13}$C, and $^{14}$C; O may be in any isotopic form, including $^{16}$O and $^{18}$O; and the like.

The term "pharmaceutically acceptable salt" is meant to include salts of the active compounds that are prepared with relatively nontoxic acids or bases, depending on the particular substituents found on the compounds described herein. When compounds used in the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds used in the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, e.g., Berge et al, *Journal of Pharmaceutical Science* 66: 1-19 (1977)). Certain specific compounds used in the present disclosure contain both basic and acidic functionalities that allow the compounds to be converted into either base or acid addition salts. These salts may be prepared by methods known to those skilled in the art. Other pharmaceutically acceptable carriers known to those of skill in the art are suitable for use in the present disclosure.

In addition to salt forms, the present disclosure may employ afibrotic compounds in a prodrug form. Prodrugs are those compounds that readily undergo chemical changes under physiological conditions to provide the afibrotic compounds useful in the present invention. Additionally, prodrugs can be converted to useful afibrotic compounds by chemical or biochemical methods in an ex vivo environment.

Certain afibrotic compounds useful in the present disclosure can exist in unsolvated forms as well as solvated forms, including hydrated forms. In general, the solvated forms are equivalent to unsolvated forms and are encompassed within the scope of the present invention. Certain afibrotic compounds useful in the present disclosure may exist in multiple crystalline or amorphous forms. In general, all physical forms are equivalent for the uses contemplated by the present disclosure and are intended to be within the scope of the present disclosure.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula R.x H$_2$O, wherein R is the compound and wherein x is a number greater than 0.

The term "tautomer" as used herein refers to compounds that are interchangeable forms of a compound structure, and that vary in the displacement of hydrogen atoms and electrons. Thus, two structures may be in equilibrium through the movement of J electrons and an atom (usually H). For example, enols and ketones are tautomers because they are rapidly interconverted by treatment with either acid or base. Tautomeric forms may be relevant to the attainment of the optimal chemical reactivity and biological activity of a compound of interest.

Preparing Hydrogel Capsule Compositions

Described herein are processes comprising contacting a plurality of droplets of an afibrotic hydrogel-forming polymer solution with an aqueous cross-linking solution that comprises a process additive (e.g., a hydrophilic, non-ionic surfactant). The droplets can be formed using any technique known in the art, e.g., as described in Vegas, A., et al., *Nature Medicine* 22(3):306-311 (2016).

Briefly, in performing a process described herein, a volume of hydrogel-forming polymer solution may be loaded into a syringe, e.g., a syringe that is then capped with a blunt tipped needle. The syringe may then be placed into a syringe pump oriented vertically above a vessel containing an aqueous cross-linking solution which comprises a cross-linking agent, a buffer, an osmolarity-adjusting agent, and a process additive (e.g., a hydrophilic, non-ionic surfactant). A high voltage power generator may then be connected to the needle. The syringe pump and power generator can then be used to extrude the polymer solution (optionally containing a suspension of cells) through the needle attached to the syringe with settings determined to achieve a desired droplet rate of polymer solution into a cross-linking solution. The skilled artisan may readily determine various combinations of needle lumen sizes, voltage range, flow rate, droplet rate and drop distance to create hydrogel capsule compositions in which 90%, 95% or more of the capsules are spherical and within 10% of the target size. After exhausting the volume of polymer solution, the droplets are allowed to cross-link in the cross-linking solution for several minutes, e.g., about five minutes.

Exemplary process parameters for preparing a composition of millicapsules (e.g., 1.5 mm diameter millicapsules) include the following. The polymer solution may be extruded through a needle (e.g., an 18 gauge needle) disposed above the surface of the cross-linking solution at a distance sufficient to provide a drop distance from the needle tip to the solution surface. In an embodiment, the distance between the needle tip to the solution surface is between 1 to 5 cm. In an embodiment, the flow rate of the polymer solution through the needle is between 0.05 mL/min to 5 mL/min, or 0.05 mL/min to 2.5 mL/min, or 0.05 mL/min to about 1 mL/min, or 0.05 mL/min to 0.5 mL/min, or 0.1 mL/min to 0.5 mL/min. In an embodiment, the flow rate of the polymer solution through the needle is about 0.05 mL/min, 0.1 mL/min, 0.15 mL/min, 0.2 mL/min, 0.25 mL/min, 0.3 mL/min, 0.35 mL/min, 0.4 mL/min, 0.45 mL/min, or 0.5 mL/min. In an embodiment, the voltage of the instrument is between 1 kV to 20 kV, or 1 to 15 kV, or 1 kV to 10 kV, or 5 kV to 10 kV. The voltage may be adjusted until a desired droplet rate is reached. In an embodiment, the droplet rate of the instrument is between 1 droplet/10 seconds to 50 droplets/10 seconds, or 1 droplet/10 seconds to 25 droplets/10 seconds.

In an embodiment, the number of non-capsule debris on the surface of the cross-linking solution is determined. Hydrogel capsules that have fallen to the bottom of the cross-linking vessel may then be collected, e.g., by transferring cross-linking solution containing the hydrogel capsules to a separate container, leaving behind any non-capsular debris on the solution surface in the original cross-linking vessel. The removed hydrogel capsules may then be allowed to settle, the cross-linking solution can be removed, and the capsules may then be washed one or more times with a buffer (e.g., a HEPES buffer). In an embodiment, one or more aliquots of the resulting hydrogel capsule composition is inspected by microscopy to assess the quality of the composition, e.g., the number of capsule defects and satellite capsules.

Agents useful as the process additive in the present invention include non-ionic surfactants, and exemplary surfactants are listed in Table 1 below.

TABLE 1

Non-ionic surfactants useful as a process additive in cross-linking solution

| Brand or Generic Name | Commercial Supplier | Approximate Average Molecular Weight (g/mole) | Hydrophilicity HLB[a] |
|---|---|---|---|
| Tween ® 20[b] | Millipore Sigma | 1228 | 16.7 |
| Tween ® 80[c] | Millipore Sigma | 1310 | 15 |
| Triton™ X-100[d] | Millipore Sigma | 625 | 13.4 |
| IGEPAL ® CA-630[e] | Millipore Sigma | 603 | 13 |
| poloxamer 188[f] | Millipore Sigma | 8400 | >24 |
| poloxamer 407[g] | Millipore Sigma | 12,500 | 18-23 |

[a]hydrophilic-lipophilic balance
[b]Chemical names and synonyms: polyethylene glycol sorbitan monolaurate, polyoxyethylene (20) sorbitan monolaurate, polysorbate 20, polyoxyethylene 20 sorbitan monododecanoate
[c]Chemical names and synonyms: polyethylene glycol sorbitan monooleate, polyoxyethylene (20) sorbitan monooleate, polysorbate 80, (x)-sorbitan mono-9-octadecenoate poly(oxy-1,2-ethanediyl)
[d]Chemical names and synonyms: 4-(1,1,3,3-Tetramethylbutyl)phenyl-polyethylene glycol, t-octylphenoxypolyethoxyethanol, polyethylene glycol tert-octylphenyl ether; octylphenol ethoxylate, octylphenol ethylene oxide condensate
[e]Chemical names and synonyms: octylphenoxypolyethoxyethanol, octylphenoxy poly(ethyleneoxy)ethanol, branched
[f]Chemical name: Poly(ethylene glycol)-block-poly(propylene glycol)-block-poly(ethylene glycol)
[g]Chemical name: Poly(ethylene glycol)-block-poly(propylene glycol)-block-poly(ethylene glycol)

In an embodiment, the process additive comprises more than one surfactant, e.g., more than one hydrophilic surfactant. In some embodiments, the process additive does not contain Tween® 20 (polysorbate 20) or Triton™ X-100. In an embodiment, the process additive is IGEPAL® CA-630 (polyethylene glycol sorbitan monooleate). In an embodiment, the process additive is poloxamer 188.

In an embodiment, the process additive is poloxamer 188, which is present in the hydrogel capsule composition in a detectable amount after the wash steps. Poloxamer 188 may be detected by any technique known in the art, e.g., by partially or completely dissolving the capsules in an aliquot of the composition by sodium sulfate precipitation and analyzing the supernatant by LC/MS.

Reduction in the surface tension of the cross-linking solution may be assessed by any method known in the art, for example, through the use of a contact angle goniometer or a tensiometer, e.g., via the du Nouy ring method (see, e.g., Davarci et al (2017) *Food Hydrocolloids* 62:119-127).

Compositions of Sfibrotic Hydrogel-Forming Polymer Solutions

In some embodiments, the hydrogel-forming polymer solution comprises an afibrotic polymer. In some embodiments, the afibrotic polymer comprises a compound of Formula (I):

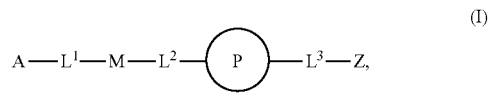

or a salt thereof, wherein:

A is alkyl, alkenyl, alkynyl, heteroalkyl, cycloalkyl, heterocyclyl, aryl, heteroaryl, —O—, —C(O)O—, —C(O)—, —OC(O)—, —N($R^C$)—, —N($R^C$)C(O)—, —C(O)N($R^C$)—, —N($R^C$)C(O)($C_1$-$C_6$-alkylene)-, —N($R^C$)C(O)($C_1$-$C_6$-alkenylene)-, —N($R^C$)N($R^D$)—, —NCN—, —C(=N($R^C$)($R^D$))O—, —S—, —S(O)$_x$—, —OS(O)$_x$—, —N($R^C$)S(O)$_x$—, —S(O)$_x$N($R^C$)—, —P($R^F$)$_y$—, —Si($OR^A$)$_2$—, —Si($R^G$)($OR^A$)—, —B($OR^A$)—, or a metal, each of which is optionally linked to an attachment group (e.g., an attachment group described herein) and is optionally substituted by one or more $R^1$;

each of $L^1$ and $L^3$ is independently a bond, alkyl, or heteroalkyl, wherein each alkyl and heteroalkyl is optionally substituted by one or more $R^2$.

$L^2$ is a bond;

M is absent, alkyl, heteroalkyl, cycloalkyl, heterocyclyl, aryl, or heteroaryl, each of which is optionally substituted by one or more $R^3$;

P is absent, cycloalkyl, heterocycyl, or heteroaryl, each of which is optionally substituted by one or more $R^4$.

Z is hydrogen, alkyl, alkenyl, alkynyl, heteroalkyl, —$OR^A$, —C(O)$R^A$, —C(O)$OR^A$, —C(O)N($R^C$)($R^D$), —N($R^C$)C(O)$R^A$, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted by one or more $R^5$;

each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted with one or more $R^6$.

or $R^C$ and $R^D$, taken together with the nitrogen atom to which they are attached, form a ring (e.g., a 5-7 membered ring), optionally substituted with one or more $R^6$;

each $R^1$, $R^2$, $R^3$, $R^4$, $R^5$, and $R^6$ is independently alkyl, alkenyl, alkynyl, heteroalkyl, halogen, cyano, azido, oxo, —$OR^{A1}$, —C(O)$OR^{A1}$, —C(O)$R^{B1}$, —OC(O)$R^{B1}$, —N($R^{C1}$)($R^{D1}$), —N($R^{C1}$)C(O)$R^{B1}$, —C(O)N($R^{C1}$), $SR^{E1}$, S(O)$_xR^{E1}$, —OS(O)$_xR^{E1}$, —N($R^{C1}$)S(O)$_xR^{E1}$, —S(O)$_x$N($R^{C1}$)($R^{D1}$), —P($R^{F1}$)$_y$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$;

each $R^{A1}$, $R^{B1}$, $R^{C1}$, $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$;

each $R^7$ is independently alkyl, alkenyl, alkynyl, heteroalkyl, halogen, cyano, oxo, hydroxyl, cycloalkyl, or heterocyclyl;

x is 1 or 2; and y is 2, 3, or 4.

In some embodiments, the compound of Formula (I) is a compound of Formula (I-a):

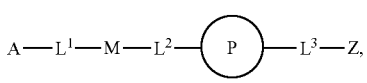

(I-a)

or a salt thereof, wherein:

A is alkyl, alkenyl, alkynyl, heteroalkyl, cycloalkyl, heterocyclyl, aryl, heteroaryl, —O—, —C(O)O—, —C(O)—, —OC(O)—, —N($R^C$)—, —N($R^C$)C(O)—, —C(O)N($R^C$)—, —N($R^C$)N($R^D$)—, —NCN—, —C(=N($R^C$)($R^D$))O—, —S—, —S(O)$_x$—, —OS(O)$_x$—, —N($R^C$)S(O)$_x$—, —S(O)$_x$N($R^C$)—, —P($R^F$)$_y$—, —Si(O$R^A$)$_2$—, —Si($R^G$)(O$R^A$)—, —B(O$R^A$)—, or a metal, each of which is optionally linked to an attachment group (e.g., an attachment group described herein) and optionally substituted by one or more $R^1$;

each of $L^1$ and $L^3$ is independently a bond, alkyl, or heteroalkyl, wherein each alkyl and heteroalkyl is optionally substituted by one or more $R^2$.

$L^2$ is a bond;

M is alkyl, heteroalkyl, cycloalkyl, heterocyclyl, aryl, or heteroaryl, each of which is optionally substituted by one or more $R^3$;

P is heteroaryl optionally substituted by one or more $R^4$.

Z is alkyl, alkenyl, alkynyl, heteroalkyl, cycloalkyl, heterocyclyl, aryl, or heteroaryl, each of which is optionally substituted by one or more $R^5$;

each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted with one or more $R^6$.

or $R^C$ and $R^D$, taken together with the nitrogen atom to which they are attached, form a ring (e.g., a 5-7 membered ring), optionally substituted with one or more $R^6$.

each $R^1$, $R^2$, $R^3$, $R^4$, $R^5$, and $R^6$ is independently alkyl, alkenyl, alkynyl, heteroalkyl, halogen, cyano, azido, oxo, —O$R^{A1}$, —C(O)O$R^{A1}$, —C(O)$R^{B1}$, —OC(O)$R^{B1}$, —N($R^{C1}$)($R^{D1}$), —N($R^{C1}$)C(O)$R^{B1}$, —C(O)N($R^{C1}$), S$R^{E1}$, S(O)$_x R^{E1}$, —OS(O)$_x R^{E1}$, —N($R^{C1}$)S(O)$_x R^{E1}$, —S(O)$_x$N($R^{C1}$)($R^{D1}$), —P($R^{F1}$)$_y$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$;

each $R^{A1}$, $R^{B1}$, $R^{C1}$, $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$;

each $R^7$ is independently alkyl, alkenyl, alkynyl, heteroalkyl, halogen, cyano, oxo, hydroxyl, cycloalkyl, or heterocyclyl;

x is 1 or 2; and y is 2, 3, or 4.

In some embodiments, for Formulas (I) and (I-a), A is alkyl, alkenyl, alkynyl, heteroalkyl, cycloalkyl, heterocyclyl, aryl, heteroaryl, —O—, —C(O)O—, —C(O)—, —OC(O)—, —N($R^C$)C(O)—, —N($R^C$)C(O)($C_1$-$C_6$-alkylene)-, —N($R^C$)C(O)($C_1$-$C_6$-alkenylene)-, or —N($R^C$)—. In some embodiments, A is alkyl, alkenyl, alkynyl, heteroalkyl, cycloalkyl, heterocyclyl, aryl, heteroaryl, —O—, —C(O)O—, —C(O)—, —OC(O)—, or —N($R^C$)—. In some embodiments, A is alkyl, alkenyl, alkynyl, heteroalkyl, —O—, —C(O)O—, —C(O)—, —OC(O)—, or —N($R^C$)—. In some embodiments, A is alkyl, —O—, —C(O)O—, —C(O)—, —OC(O), or —N($R^C$)—. In some embodiments, A is —N($R^C$)C(O)—, —N($R^C$)C(O)($C_1$-$C_6$-alkylene)-, or —N($R^C$)C(O)($C_1$-$C_6$-alkenylene)-. In some embodiments, A is —N($R^C$)—. In some embodiments, A is —N($R^C$)—, and $R^C$ an $R^D$ is independently hydrogen or alkyl. In some embodiments, A is —NH—. In some embodiments, A is —N($R^C$)C(O)($C_1$-$C_6$-alkylene)-, wherein alkylene is substituted with $R^4$. In some embodiments, A is —N($R^C$)C(O)($C_1$-$C_6$-alkylene)-, and $R^4$ is alkyl (e.g., methyl). In some embodiments, A is —NHC(O)C(CH$_3$)$_2$—. In some embodiments, A is —N($R^C$)C(O)(methylene)-, and $R^4$ is alkyl (e.g., methyl). In some embodiments, A is —NHC(O)CH(CH$_3$)—. In some embodiments, A is —NHC(O)C(CH$_3$)—.

In some embodiments, for Formulas (I) and (I-a), $L^1$ is a bond, alkyl, or heteroalkyl. In some embodiments, $L^1$ is a bond or alkyl. In some embodiments, $L^1$ is a bond. In some embodiments, $L^1$ is alkyl. In some embodiments, $L^1$ is $C_1$-$C_6$ alkyl. In some embodiments, $L^1$ is —CH$_2$—, —CH(CH$_3$)—, —CH$_2$CH$_2$CH$_2$, or —CH$_2$CH$_2$—. In some embodiments, $L^1$ is —CH$_2$— or —CH$_2$CH$_2$—.

In some embodiments, for Formulas (I) and (I-a), $L^3$ is a bond, alkyl, or heteroalkyl. In some embodiments, $L^3$ is a bond. In some embodiments, $L^3$ is alkyl. In some embodiments, $L^3$ is $C_1$-$C_{12}$ alkyl. In some embodiments, $L^3$ is $C_1$-$C_6$ alkyl. In some embodiments, $L^3$ is —CH$_2$—. In some embodiments, $L^3$ is heteroalkyl. In some embodiments, $L^3$ is $C_1$-$C_{12}$ heteroalkyl, optionally substituted with one or more $R^2$ (e.g., oxo). In some embodiments, $L^3$ is $C_1$-$C_6$ heteroalkyl, optionally substituted with one or more $R^2$ (e.g., oxo). In some embodiments, $L^3$ is —C(O)OCH$_2$—, —CH$_2$(OCH$_2$CH$_2$)$_2$—, —CH$_2$(OCH$_2$CH$_2$)$_3$—, CH$_2$CH$_2$O—, or —CH$_2$O—. In some embodiments, $L^3$ is —CH$_2$O—.

In some embodiments, for Formulas (I) and (I-a), M is absent, alkyl, heteroalkyl, aryl, or heteroaryl. In some embodiments, M is heteroalkyl, aryl, or heteroaryl. In some embodiments, M is absent. In some embodiments, M is alkyl (e.g., $C_1$-$C_6$ alkyl). In some embodiments, M is —CH$_2$—. In some embodiments, M is heteroalkyl (e.g., $C_1$-$C_6$ heteroalkyl). In some embodiments, M is (—OCH$_2$CH$_2$-)z, wherein z is an integer selected from 1 to 10. In some embodiments, z is an integer selected from 1 to 5. In some embodiments, M is —OCH$_2$CH$_2$—, (—OCH$_2$CH$_2$-)$_2$, (—OCH$_2$CH$_2$-)$_3$, (—OCH$_2$CH$_2$-)$_4$, or (—OCH$_2$CH$_2$-)$_5$. In some embodiments, M is —OCH$_2$CH$_2$—, (—OCH$_2$CH$_2$-)$_2$, (—OCH$_2$CH$_2$-)$_3$, or (—OCH$_2$CH$_2$-)$_4$. In some embodiments, M is (—OCH$_2$CH$_2$-)$_3$. In some embodiments, M is aryl. In some embodiments, M is phenyl. In some embodiments, M is unsubstituted phenyl. In some embodiments, M is

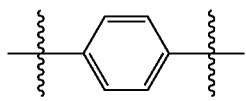

In some embodiments, M is phenyl substituted with $R^7$ (e.g., 1 $R^7$). In some embodiments, M is

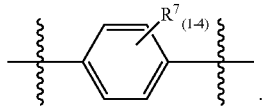

In some embodiments, $R^7$ is $CF_3$.

In some embodiments, for Formulas (I) and (I-a), P is absent, heterocyclyl, or heteroaryl. In some embodiments, P is absent. In some embodiments, for Formulas (I) and (I-a), P is a tricyclic, bicyclic, or monocyclic heteroaryl. In some embodiments, P is a monocyclic heteroaryl. In some embodiments, P is a nitrogen-containing heteroaryl. In some embodiments, P is a monocyclic, nitrogen-containing heteroaryl. In some embodiments, P is a 5-membered heteroaryl. In some embodiments, P is a 5-membered nitrogen-containing heteroaryl. In some embodiments, P is tetrazolyl, imidazolyl, pyrazolyl, or triazolyl, pyrrolyl, oxazolyl, or thiazolyl. In some embodiments, P is tetrazolyl, imidazolyl, pyrazolyl, or triazolyl, or pyrrolyl. In some embodiments, P is imidazolyl. In some embodiments, P is

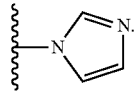

In some embodiments, P is triazolyl. In some embodiments, P is 1,2,3-triazolyl. In some embodiments, P is

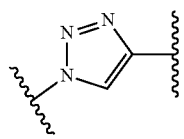

In some embodiments, P is heterocyclyl. In some embodiments, P is a 5-membered heterocyclyl or a 6-membered heterocyclyl. In some embodiments, P is imidazolidinonyl. In some embodiments, P is

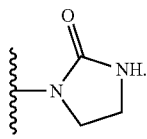 [SMILES: *N1CCNC1=O]

In some embodiments, P is thiomorpholinyl-1,1-dioxidyl. In some embodiments, P is

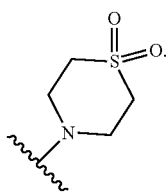 [SMILES: *N1CCS(=O)(=O)CC1]

In some embodiments, for Formulas (I) and (I-a), Z is alkyl, heteroalkyl, cycloalkyl, heterocyclyl, aryl, or heteroaryl. In some embodiments, Z is heterocyclyl. In some embodiments, Z is monocyclic or bicyclic heterocyclyl. In some embodiments, Z is an oxygen-containing heterocyclyl. In some embodiments, Z is a 4-membered heterocyclyl, 5-membered heterocyclyl, or 6-membered heterocyclyl. In some embodiments, Z is a 6-membered heterocyclyl. In some embodiments, Z is a 6-membered oxygen-containing heterocyclyl. In some embodiments, Z is tetrahydropyranyl. In some embodiments, Z is

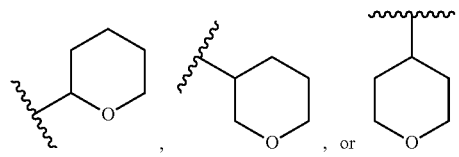

In some embodiments, Z is a 4-membered oxygen-containing heterocyclyl. In some embodiments, Z is O

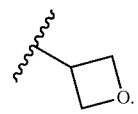 [SMILES: *C1COC1]

In some embodiments, Z is a bicyclic oxygen-containing heterocyclyl. In some embodiments, Z is phthalic anhydridyl. In some embodiments, Z is a sulfur-containing heterocyclyl. In some embodiments, Z is a 6-membered sulfur-containing heterocyclyl. In some embodiments, Z is a 6-membered heterocyclyl containing a nitrogen atom and a sulfur atom. In some embodiments, Z is thiomorpholinyl-1,1-dioxidyl. In some embodiments, Z is

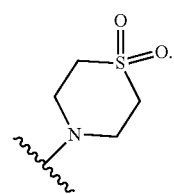 [SMILES: *N1CCS(=O)(=O)CC1]

In some embodiments, Z is a nitrogen-containing heterocyclyl. In some embodiments, Z is a 6-membered nitrogen-containing heterocyclyl. In some embodiments, Z is

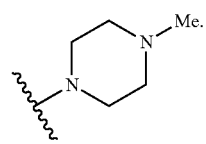 [SMILES: *N1CCN(C)CC1]

In some embodiments, Z is a bicyclic heterocyclyl. In some embodiments, Z is a bicyclic nitrogen-containing heterocyclyl, optionally substituted with one or more $R^5$. In some embodiments, Z is 2-oxa-7-azaspiro[3.5]nonanyl. In some embodiments, Z is

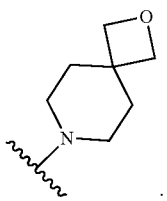 [SMILES: *N1CCC2(CC1)COC2]

In some embodiments, Z is 1-oxa-3,8-diazaspiro[4.5]decan-2-one. In some embodiments, Z is

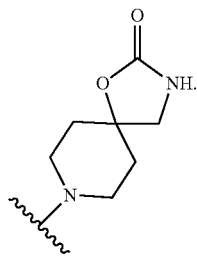 [SMILES: *N1CCC2(CC1)CNC(=O)O2]

In some embodiments, for Formulas (I) and (I-a), Z is aryl. In some embodiments, Z is monocyclic aryl. In some embodiments, Z is phenyl. In some embodiments, Z is monosubstituted phenyl (e.g., with 1 $R^5$). In some embodiments, Z is monosubstituted phenyl, wherein the 1 $R^5$ is a nitrogen-containing group. In some embodiments, Z is monosubstituted phenyl, wherein the 1 $R^5$ is $NH_2$. In some embodiments, Z is monosubstituted phenyl, wherein the 1 $R^5$ is an oxygen-containing group. In some embodiments, Z is monosubstituted phenyl, wherein the 1 $R^5$ is an oxygen-containing heteroalkyl. In some embodiments, Z is monosubstituted phenyl, wherein the 1 $R^5$ is $OCH_3$. In some embodiments, Z is monosubstituted phenyl, wherein the 1 $R^5$ is in the ortho position. In some embodiments, Z is monosubstituted phenyl, wherein the 1 $R^5$ is in the meta position. In some embodiments, Z is monosubstituted phenyl, wherein the 1 $R^5$ is in the para position.

In some embodiments, for Formulas (I) and (I-a), Z is alkyl. In some embodiments, Z is $C_1$-$C_{12}$ alkyl. In some embodiments, Z is $C_1$-$C_{10}$ alkyl. In some embodiments, Z is $C_1$-$C_8$ alkyl. In some embodiments, Z is $C_1$-$C_8$ alkyl substituted with 1-5 $R^5$. In some embodiments, Z is $C_1$-$C_8$ alkyl substituted with 1 $R^5$. In some embodiments, Z is $C_1$-$C_8$ alkyl substituted with 1 $R^5$, wherein $R^5$ is alkyl, heteroalkyl, halogen, oxo, —$OR^{A1}$, —$C(O)OR^{A1}$, —$C(O)R^{B1}$, —$OC(O)R^{B1}$, or —$N(R^{C1})(R^{D1})$. In some embodiments, Z is $C_1$-$C_8$ alkyl substituted with 1 $R^5$, wherein $R^5$ is —$OR^{A1}$ or —$C(O)OR^{A1}$. In some embodiments, Z is $C_1$-$C_8$ alkyl substituted with 1 $R^5$, wherein $R^5$ is —$OR^{A1}$ or —$C(O)OH$. In some embodiments, Z is —$CH_3$.

In some embodiments, for Formulas (I) and (I-a), Z is heteroalkyl. In some embodiments, Z is $C_1$-$C_{12}$ heteroalkyl. In some embodiments, Z is $C_1$-$C_{10}$ heteroalkyl. In some embodiments, Z is $C_1$-$C_8$ heteroalkyl. In some embodiments, Z is $C_1$-$C_6$ heteroalkyl. In some embodiments, Z is a nitrogen-containing heteroalkyl optionally substituted with one or more $R^5$. In some embodiments, Z is a nitrogen and sulfur-containing heteroalkyl substituted with 1-5 $R^5$. In some embodiments, Z is N-methyl-2-(methylsulfonyl)ethan-1-aminyl.

In some embodiments, Z is —$OR^A$ or —$C(O)OR^A$. In some embodiments, Z is —$OR^A$ (e.g., —OH or —$OCH_3$). In some embodiments, Z is —$OCH_3$. In some embodiments, Z is —$C(O)OR^A$ (e.g., —C(O)OH).

In some embodiments, Z is hydrogen.

In some embodiments, $L^2$ is a bond and P and $L^3$ are independently absent. In some embodiments, $L^2$ is a bond, P is heteroaryl, $L^3$ is a bond, and Z is hydrogen. In some embodiments, P is heteroaryl, $L^3$ is heteroalkyl, and Z is alkyl.

In some embodiments, the compound of Formula (I) is a compound of Formula (II):

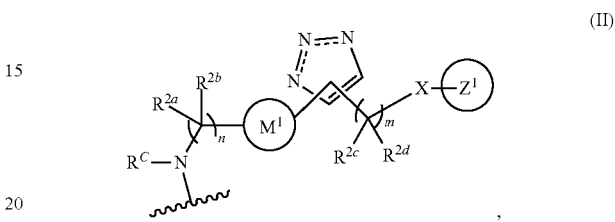

(II)

or a salt thereof, wherein Ring $M^1$ is cycloalkyl, heterocyclyl, aryl, or heteroaryl, each of which is optionally substituted with 1-5 $R^3$; Ring $Z^1$ is cycloalkyl, heterocyclyl, aryl or heteroaryl, optionally substituted with 1-5 $R^5$; each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl, or each of $R^{2a}$ and $R^{2b}$ or $R^{2c}$ and $R^{2d}$ is taken together to form an oxo group; X is absent, $N(R^{10})(R^{11})$, O, or S; $R^C$ is hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$; each $R^3$, $R^5$, and $R^6$ is independently alkyl, alkenyl, alkynyl, heteroalkyl, halogen, cyano, azido, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, $SR^{E1}$, cycloalkyl, heterocyclyl, aryl, or heteroaryl; each of $R^{10}$ and $R^{11}$ is independently hydrogen, alkyl, alkenyl, alkynyl, heteroalkyl, —$C(O)OR^{A1}$, —$C(O)R^{B1}$, —$OC(O)R^{B1}$, —$C(O)N(R^{C1})$ cycloalkyl, heterocyclyl, aryl, or heteroaryl; each $R^{A1}$, $R^{B1}$, $R^{C1}$, $R^{D1}$, and $R^{E1}$ is independently hydrogen, alkyl, alkenyl, alkynyl, heteroalkyl, cycloalkyl, heterocyclyl, aryl, heteroaryl, wherein each of alkyl, alkenyl, alkynyl, heteroalkyl, cycloalkyl, heterocyclyl, aryl, heteroaryl is optionally substituted with 1-6 $R^7$; each $R^7$ is independently alkyl, alkenyl, alkynyl, heteroalkyl, halogen, cyano, oxo, hydroxyl, cycloalkyl, or heterocyclyl; each m and n is independently 1, 2, 3, 4, 5, or 6; and "⌇" refers to a connection to an attachment group or a polymer described herein.

In some embodiments, the compound of Formula (II) is a compound of Formula (II-a):

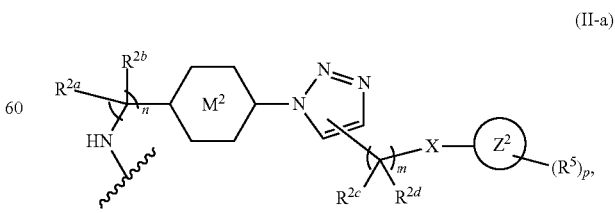

(II-a)

or a salt thereof, wherein Ring $M^2$ is aryl or heteroaryl optionally substituted with one or more $R^3$; Ring $Z^2$ is cycloalkyl, heterocyclyl, aryl, or heteroaryl; each of $R^{2a}$, $R^{2b}$, $R^{2c}$, and $R^{2d}$ is independently hydrogen, alkyl, or heteroalkyl, or each of $R^{2a}$ and $R^{2b}$ or $R^{2c}$ and $R^{2d}$ is taken together to form an oxo group; X is absent, O, or S; each $R^3$ and $R^5$ is independently alkyl, heteroalkyl, halogen, oxo, —$OR^{A1}$, —$C(O)OR^{A1}$, or —$C(O)R^{B1}$; or two $R^5$ are taken together to form a 5-6 membered ring fused to Ring $Z^2$; each $R^{A1}$ and $R^{B1}$ is independently hydrogen, alkyl, or heteroalkyl; m and n are each independently 1, 2, 3, 4, 5, or 6; p is 0, 1, 2, 3, 4, 5, or 6; and " ⌇ " refers to a connection to an attachment group or a polymer described herein.

In some embodiments, the compound of Formula (II-a) is a compound of Formula (II-b):

(II-b)

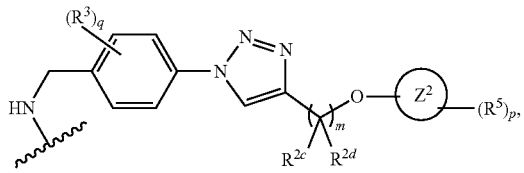

or a salt thereof, wherein Ring $Z^2$ is cycloalkyl, heterocyclyl, aryl or heteroaryl; each $R^3$ and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; each of p and q is independently 0, 1, 2, 3, 4, 5, or 6; and " ⌇ " refers to a connection to an attachment group or a polymer described herein.

In some embodiments, the compound of Formula (II-a) is a compound of Formula (II-c):

(II-c)

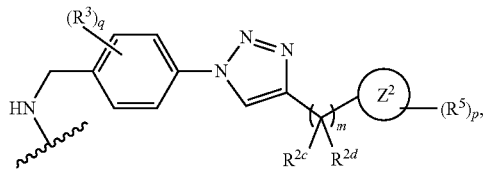

or a salt thereof, wherein Ring $Z^2$ is cycloalkyl, heterocyclyl, aryl or heteroaryl; each of $R^{2c}$ and $R^{2d}$ is independently hydrogen, alkyl, or heteroalkyl, or each of $R^{2c}$ and $R^{2d}$ is taken together to form an oxo group; each $R^3$ and $R^5$ is independently alkyl, heteroalkyl, halogen, oxo, —$OR^A$, —$C(O)OR^{A1}$, or —$C(O)R^{B1}$; each $R^{A1}$ and $R^{B1}$ is independently hydrogen, alkyl, or heteroalkyl; m is 1, 2, 3, 4, 5, or 6; each of p and q is independently 0, 1, 2, 3, 4, 5, or 6; and " ⌇ " refers to a connection to an attachment group or a polymer described herein.

In some embodiments, the compound of Formula (II-a) is a compound of Formula (II-d):

(II-d)

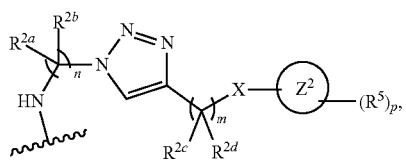

or a salt thereof, wherein Ring $Z^2$ is cycloalkyl, heterocyclyl, aryl or heteroaryl; X is absent, O, or S; each of $R^{2a}$, $R^{2b}$, $R^{2c}$, and $R^{2d}$ is independently hydrogen, alkyl, or heteroalkyl, or each of $R^{2a}$ and $R^{2b}$ or $R^{2c}$ and $R^{2d}$ is taken together to form an oxo group; each $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; each of m and n is independently 1, 2, 3, 4, 5, or 6; p is 0, 1, 2, 3, 4, 5, or 6; and " ⌇ " refers to a connection to an attachment group or a polymer described herein.

In some embodiments, the compound of Formula (I) is a compound of Formula (III):

(III)

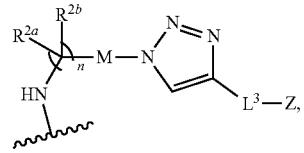

or a salt thereof, wherein M is a alkyl or aryl, each of which is optionally substituted with one or more $R^3$; $L^3$ is alkyl or heteroalkyl optionally substituted with one or more $R^2$; Z is alkyl, heteroalkyl, cycloalkyl, heterocyclyl, aryl, or heteroaryl, each of which is optionally substituted with one or more $R^5$; each of $R^{2a}$ and $R^{2b}$ is independently hydrogen, alkyl, or heteroalkyl, or $R^{2a}$ and $R^{2b}$ is taken together to form an oxo group; each $R^2$, $R^3$, and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; n is independently 1, 2, 3, 4, 5, or 6; and " ⌇ " refers to a connection to an attachment group or a polymer described herein.

In some embodiments, the compound of Formula (III) is a compound of Formula (III-a):

(III-a)

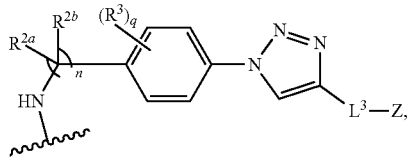

or a salt thereof, wherein $L^3$ is alkyl or heteroalkyl, each of which is optionally substituted with one or more $R^2$; Z is alkyl or heteroalkyl, each of which is optionally substituted with one or more $R^5$; each of $R^{2a}$ and $R^{2b}$ is independently hydrogen, alkyl, or heteroalkyl, or $R^{2a}$ and $R^{2b}$ is taken together to form an oxo group; each $R^2$, $R^3$, and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; n is independently 1, 2, 3, 4, 5, or 6; and " ⌇ " refers to a connection to an attachment group or a polymer described herein.

In some embodiments, the compound of Formula (I) is a compound of Formula (IV):

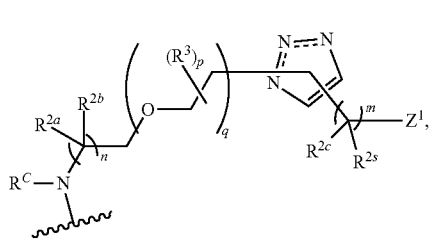

(IV)

or a salt thereof, wherein Z is alkyl, alkenyl, alkynyl, heteroalkyl, cycloalkyl, heterocyclyl, aryl, or heteroaryl, each of which is optionally substituted with 1-5 $R^5$; each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl; or $R^{2a}$ and $R^{2b}$ or $R^{2c}$ and $R^{2d}$ are taken together to form an oxo group; $R^C$ is hydrogen, alkyl, alkenyl, wherein each of alkyl and alkenyl is optionally substituted with 1-6 $R^6$; each of $R^3$, $R^5$, and $R^6$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; m and n are each independently 1, 2, 3, 4, 5, or 6; q is an integer from 0 to 25; and "〰" refers to a connection to an attachment group or a polymer described herein.

In some embodiments, the compound of Formula (IV) is a compound of Formula (IV-a):

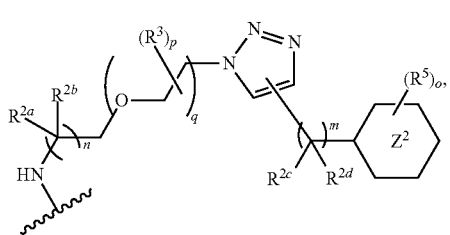

(IV-a)

or a salt thereof, wherein Ring $Z^2$ is cycloalkyl, heterocyclyl, aryl, or heteroaryl; each of $R^{2a}$, $R^{2b}$, $R^{2c}$, and $R^{2d}$ is independently hydrogen, alkyl, heteroalkyl, halo; or $R^{2a}$ and $R^{2b}$ or $R^{2c}$ and $R^{2d}$ are taken together to form an oxo group; each of $R^3$ and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; m and n are each independently 1, 2, 3, 4, 5, or 6; o and p are each independently 0, 1, 2, 3, 4, or 5; q is an integer from 0 to 25; and "〰" refers to a connection to an attachment group or a polymer described herein.

In some embodiments, the compound of Formula (IV-a) is a compound of Formula (IV-b):

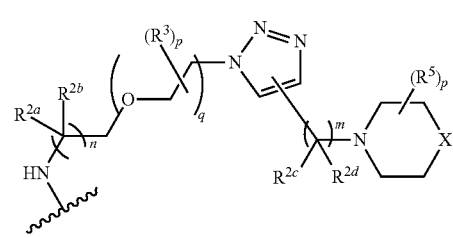

(IV-b)

or a salt thereof, wherein X is C(R')(R"), N(R'), or $S(O)_x$; each of R' and R" is independently hydrogen, alkyl, halogen, or cycloalkyl; each of $R^{2a}$, $R^{2b}$, $R^{2c}$, and $R^{2d}$ is independently hydrogen, alkyl, heteroalkyl, or halo; or $R^{2a}$ and $R^{2b}$ or $R^{2c}$ and $R^{2d}$ are taken together to form an oxo group; each of $R^3$ and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; m and n are each independently 1, 2, 3, 4, 5, or 6; p is 0, 1, 2, 3, 4, or 5; q is an integer from 0 to 25; x is 0, 1, or 2; and "〰" refers to a connection to an attachment group or a polymer described herein.

In some embodiments, the afibrotic compound is a compound of Formula (I). In some embodiments, $L^2$ is a bond and P and $L^3$ are independently absent. In some embodiments, $L^2$ is a bond, P is heteroaryl, $L^3$ is a bond, and Z is hydrogen. In some embodiments, P is heteroaryl, $L^3$ is heteroalkyl, and Z is alkyl. In some embodiments, $L^2$ is a bond and P and $L^3$ are independently absent. In some embodiments, $L^2$ is a bond, P is heteroaryl, $L^3$ is a bond, and Z is hydrogen. In some embodiments, $L^2$ is a bond, P is heteroaryl, $L^3$ is heteroalkyl, and Z is alkyl.

In some embodiments, the afibrotic compound is a compound of Formula (II-b). In some embodiments of Formula (II-b), each of $R^{2c}$ and $R^{2d}$ is independently hydrogen, m is 1, q is 0, p is 0, and Z is heterocyclyl (e.g., an oxygen-containing heterocyclyl). In some embodiments, the compound of Formula (II-b) is Compound 100.

In some embodiments, the afibrotic compound is a compound of Formula (II-c). In some embodiments of Formula (II-c), each of $R^{2c}$ and $R^{2d}$ is independently hydrogen, m is 1, p is 1, q is 0, $R^5$ is —$CH_3$, and Z is heterocyclyl (e.g., a nitrogen-containing heterocyclyl). In some embodiments, the compound of Formula (II-c) is Compound 113.

In some embodiments, the afibrotic compound is a compound of Formula (II-d). In some embodiments of Formula (II-d), each of $R^{2a}$, $R^{2b}$, $R^{2c}$, and $R^{2d}$ is independently hydrogen, each of m and n is independently 1, X is O, p is 0, and Z is heterocyclyl (e.g., an oxygen-containing heterocyclyl). In some embodiments, the compound of Formula (II-d) is Compound 110 or Compound 114.

In some embodiments, the afibrotic compound is a compound of Formula (III-a). In some embodiments of Formula (III-a), each of $R^{2a}$ and $R^{2b}$ is independently hydrogen, n is 1, q is 0, $L_3$ is —$CH_2(OCH_2CH_2)_2$—, and Z is —$OCH_3$. In some embodiments, the compound of Formula (III-a) is Compound 112.

In some embodiments, the afibrotic compound is a compound of Formula (IV-a). In some embodiments of Formula (IV-a), each of each of $R^{2a}$, $R^{2b}$, $R^{2c}$, and $R^{2d}$ is independently hydrogen, each of m and n is independently 1, p is 0, q is 3, o is 0 or 1, $R^5$, if present, is —$NH_2$, and Z is aryl or heterocyclyl (e.g., a nitrogen-containing heterocyclyl). In some embodiments, the compound of Formula (IV-a) is Compound 101 or Compound 102.

In any and all embodiments, "⁓" refers to a connection to a hydrogel-forming polymer (e.g., alginate or other polymer described herein). The connection represented by "⁓" may refer to direct attachment to the polymer or may refer to linkage to the polymer through an attachment group. An "attachment group," as described herein, refers to a moiety for linkage of a compound of Formula (I) to a polymer, and may comprise any attachment chemistry known in the art. A listing of exemplary attachment groups is outlined in *Bioconjugate Techniques* (3$^{rd}$ ed, Greg T. Hermanson, Waltham, Mass.: Elsevier, Inc, 2013), which is incorporated herein by reference in its entirety. In some embodiments, an attachment group comprises alkyl, alkenyl, alkynyl, heteroalkyl, cycloalkyl, heterocyclyl, aryl, heteroaryl, —C(O)—, —OC(O)—, —N(R$^C$)—, —N(R$^C$)C(O)—, —C(O)N(R$^C$)—, —N(R$^C$)N(R$^D$)—, —NCN—, —C(=N(R$^C$)(R$^D$))O—, —S—, —S(O)$_x$—, —OS(O)$_x$—, —N(R$^C$)S(O)$_x$—, —S(O)$_x$N(R$^C$)—, —P(R$^F$)$_y$—, —Si(OR$^A$)$_2$—, —Si(R$^G$)(OR$^A$)—, —B(OR$^A$)—, or a metal, wherein each of R$^A$, R$^C$, R$^D$, R$^F$, R$^G$, x and y is independently as described herein. In some embodiments, an attachment group comprises an amine, ketone, ester, amide, alkyl, alkenyl, alkynyl, or thiol. In some embodiments, an attachment group is a cross-linker. In some embodiments, the attachment group is —C(O)(C$_1$-C$_6$-alkylene)-, wherein alkylene is substituted with R$^4$, and R$^4$ is as described herein. In some embodiments, the attachment group is —C(O)(C$_1$-C$_6$-alkylene)-, wherein alkylene is substituted with 1-2 alkyl groups (e.g., 1-2 methyl groups). In some embodiments, the attachment group is —C(O)C(CH$_3$)$_2$—. In some embodiments, the attachment group is —C(O)(methylene)-, wherein alkylene is substituted with 1-2 alkyl groups (e.g., 1-2 methyl groups). In some embodiments, the attachment group is —C(O)CH(CH$_3$)—. In some embodiments, the attachment group is —C(O)C(CH$_3$)—.

In some embodiments, the afibrotic compound (e.g., a compound of Formula (I)) is not a compound disclosed in WO2012/112982, WO2012/167223, WO2014/153126, WO2016/019391, WO 2017/075630, US2012-0213708, US 2016-0030359 or US 2016-0030360.

In some embodiments, the afibrotic polymer comprises a compound shown in Table 2, or a pharmaceutically acceptable salt thereof.

TABLE 2

Exemplary compounds for preparing afibrotic polymers

| Compound No. | Structure |
|---|---|
| 100 | 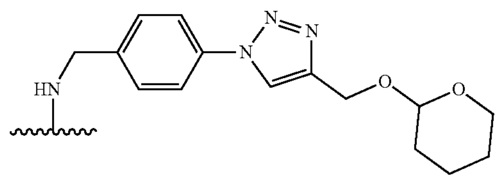 [SMILES: *NCc1ccc(-n2cc(COC3CCCCO3)nn2)cc1] |
| 101 | 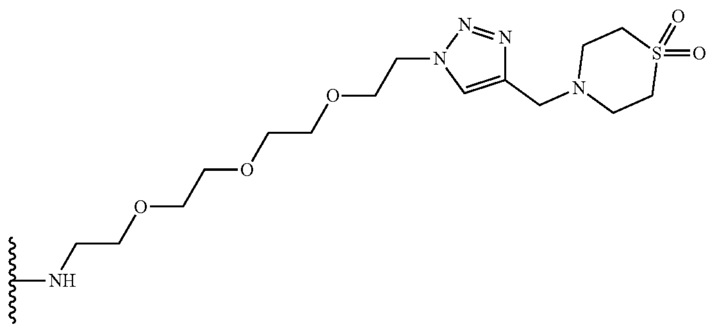 [SMILES: *NCCOCCOCCOCCn1cc(CN2CCS(=O)(=O)CC2)nn1] |
| 102 | 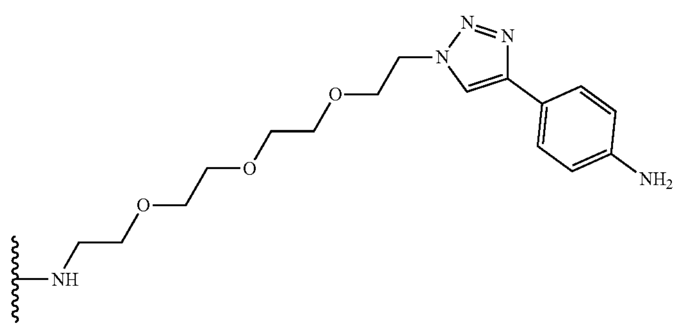 [SMILES: *NCCOCCOCCOCCn1cc(-c2ccc(N)cc2)nn1] |
| 103 | 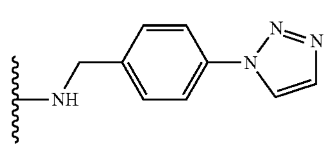 [SMILES: *NCc1ccc(-n2ccnn2)cc1] |

TABLE 2-continued
Exemplary compounds for preparing afibrotic polymers
| Compound No. | Structure |
|---|---|
| 104 | 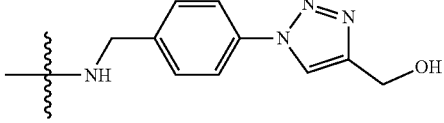 |
| 105 | 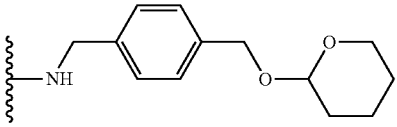 |
| 106 | 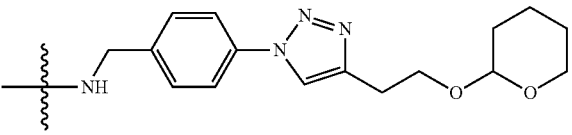 [SMILES: *NCc1ccc(-n2cc(CCOC3CCCCO3)nn2)cc1] |
| 107 | 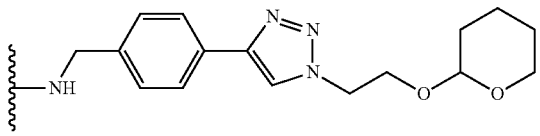 [SMILES: *NCc1ccc(-c2cn(CCOC3CCCCO3)nn2)cc1] |
| 108 | 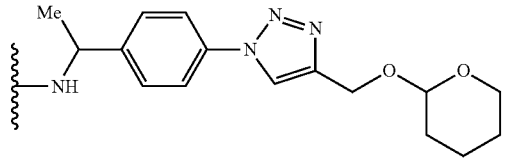 [SMILES: *NC(C)c1ccc(-n2cc(COC3CCCCO3)nn2)cc1] |
| 109 | 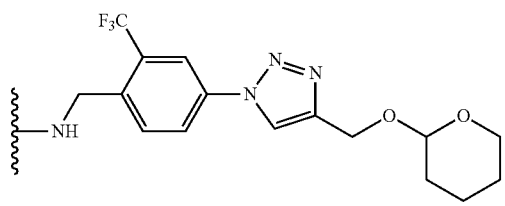 [SMILES: *NCc1ccc(-n2cc(COC3CCCCO3)nn2)cc1C(F)(F)F] |
| 110 | 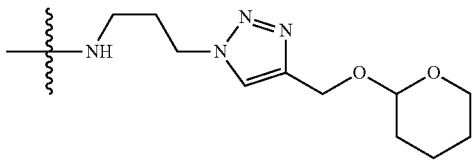 [SMILES: *NCCCn1cc(COC2CCCCO2)nn1] |
| 111 | 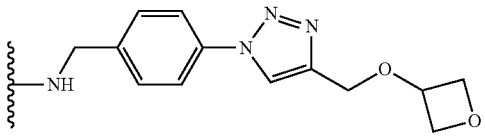 [SMILES: *NCc1ccc(-n2cc(COC3COC3)nn2)cc1] |
| 112 | 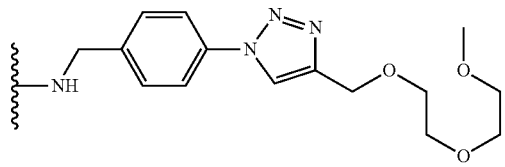 [SMILES: *NCc1ccc(-n2cc(COCCOCCOC)nn2)cc1] |

TABLE 2-continued

Exemplary compounds for preparing afibrotic polymers

| Compound No. | Structure |
|---|---|
| 113 | 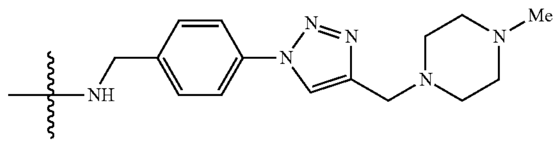 [SMILES: *NCc1ccc(-n2cc(CN3CCN(C)CC3)nn2)cc1] |
| 114 | 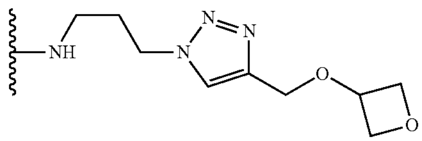 [SMILES: *NCCCn1cc(COC2COC2)nn1] |
| 115 | 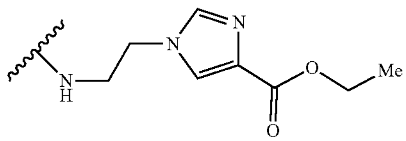 [SMILES: *NCCn1cnc(C(=O)OCC)c1] |
| 116 | 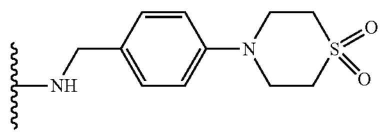 [SMILES: *NCc1ccc(N2CCS(=O)(=O)CC2)cc1] |
| 117 | 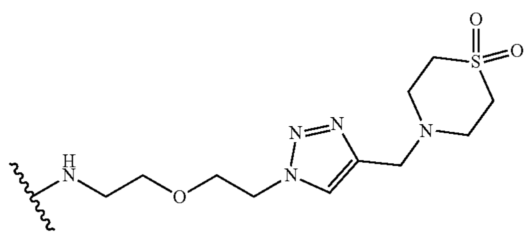 [SMILES: *NCCOCCn1cc(CN2CCS(=O)(=O)CC2)nn1] |
| 118 | 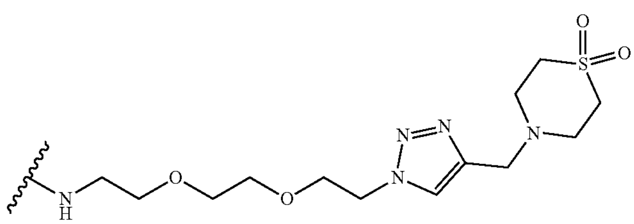 [SMILES: *NCCOCCOCCn1cc(CN2CCS(=O)(=O)CC2)nn1] |
| 119 | 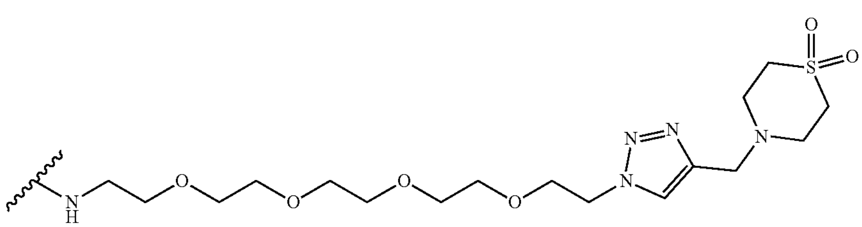 [SMILES: *NCCOCCOCCOCCOCCn1cc(CN2CCS(=O)(=O)CC2)nn1] |
| 120 | 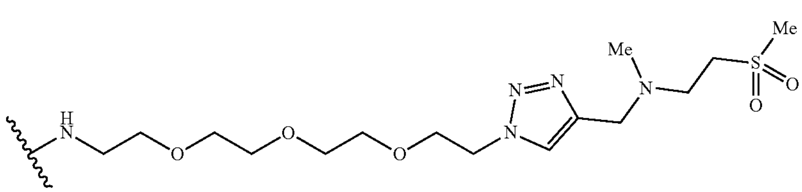 [SMILES: *NCCOCCOCCOCCn1cc(CN(C)CCS(C)(=O)=O)nn1] |

TABLE 2-continued

Exemplary compounds for preparing afibrotic polymers

| Compound No. | Structure |
|---|---|
| 121 | 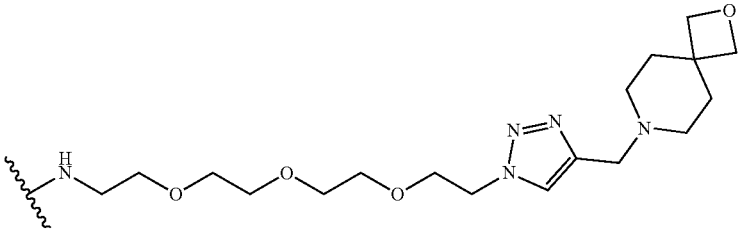 [SMILES: *NCCOCCOCCOCCn1cc(CN2CCC3(CC2)COC3)nn1] |

In some embodiments, the afibrotic compound is a compound of Formula (I) (e.g., Formulas (I-a), (II), (II-b), (II-c), (II-d), (III), (III-a), (IV), (IV-a), or (IV-b)), or a pharmaceutically acceptable salt thereof, and is selected from:

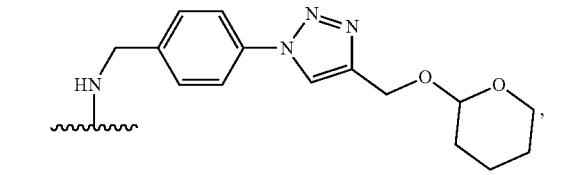

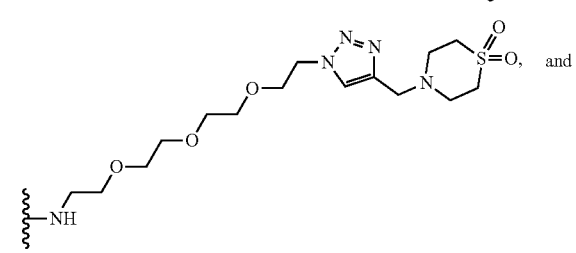

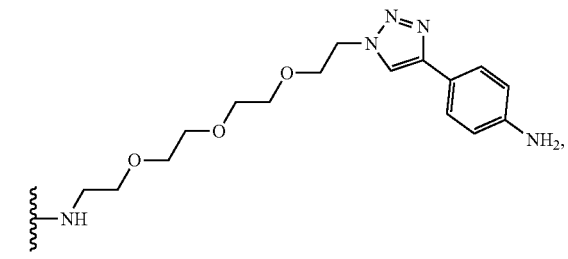

or a pharmaceutically acceptable salt thereof.

In some embodiments, the afibrotic polymer comprises the compound of

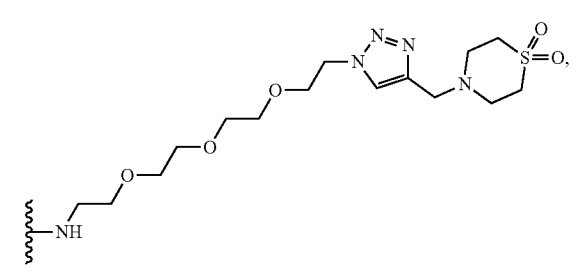

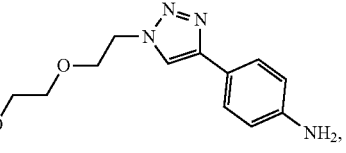

or a pharmaceutically acceptable salt of either compound.

Preparation of Afibrotic Hydrogel-Forming Polymer Solutions

The afibrotic hydrogel-forming polymer solution may be prepared using a wide variety of hydrogel-forming polymers known in the art, e.g., as described in WO 2017/075630. In some embodiments, the polymer is an alginate, e.g., a polysaccharide comprising β-D-mannuronic acid (M) and α-L-guluronic acid (G) linked together, in which an afibrotic compound is covalently attached to some or all the monomers in the alginate, e.g., as described in WO 2017/075631. In some embodiments, the alginate comprises a mixture of monomers chemically modified with different species of afibrotic compounds, e.g., different compounds of Formula I (e.g., Formulas (Formulas (I-a), (II), (II-b), (II-c), (II-d), (III), (III-a), (IV), (IV-a), or (IV-b)). In some embodiments, afibrotic hydrogel-forming polymer solution comprises a mixture of an afibrotic alginate and at least one unmodified hydrogel-forming polymer, which may be a different type of polymer or an alginate with a different molecular weight, e.g., as described in WO 2017/075631.

When alginate is used as the hydrogel-forming polymer, it can be chemically modified with the afibrotic compound(s) using any suitable method known in the art. For example, the alginate carboxylic acid moiety can be activated for coupling to one or more amine-functionalized compounds to achieve an alginate modified with an afibrotic compound of interest, e.g., a compound of Formula (I). The alginate polymer may be dissolved in water (30 mL/gram polymer) and treated with 2-chloro-4,6-dimethoxy-1,3,5-triazine (0.5 eq) and N-methylmorpholine (1 eq). To this mixture is added a solution of the compound of interest in acetonitrile (0.3M). The reaction is warmed to 55° C. for 16 h, then cooled to room temperature and gently concentrated via rotary evaporation, then the residue may be dissolved, e.g., in water. The mixture may then be filtered, e.g., through a bed of cyano-modified silica gel (Silicycle) and the filter cake washed with water. The resulting solution may then be dialyzed (10,000 MWCO membrane) against water for 24 hours, e.g., replacing the water twice. The resulting solution can be concentrated, e.g., via lyophilization, to afford the desired chemically modified alginate.

Hydrogel Capsules Encapsulating Cells

The process of the present invention can be used to encapsulate a wide variety of different human cell types in afibrotic hydrogel capsules, including epithelial cells, endothelial cells, fibroblast cells, mesenchymal stem cells, keratinocyte cells, cells derived from epithelial cells, endothelial cells, fibroblast cells, mesenchymal stem cells or keratinocyte cells, cells derived from induced pluripotent stem cells (iPSC)), and islet cells (e.g., as defined herein). Exemplary cell types include the cell types recited in WO 2017/075631. In an embodiment, a plurality of the cells to be encapsulated are added to the hydrogel-forming polymer solution as a cell suspension. The cells in the suspension may take the form of single cells (e.g., from a monolayer cell culture), or provided in another form, e.g., disposed on a microcarrier (e.g., a bead or matrix) or as a three-dimensional aggregate of cells (e.g., a cell cluster or spheroid). The cell suspension can comprise multiple cell clusters (e.g., as spheroids) or microcarriers.

In some embodiments, the encapsulated cells have been engineered to produce a therapeutic agent for the prevention or treatment of a disease, disorder, or condition described, e.g., in WO 2017/075631. The therapeutic agent may be any biological substance, such as a nucleic acid (e.g., a nucleotide, DNA, or RNA), a polypeptide, a lipid, a sugar (e.g., a monosaccharide, disaccharide, oligosaccharide, or polysaccharide), or a small molecule. Exemplary therapeutic agents include the agents listed in WO 2017/075631.

In some embodiments, the therapeutic agent is a peptide or polypeptide (e.g., a protein), such as a hormone, enzyme, cytokine (e.g., a pro-inflammatory cytokine or an anti-inflammatory cytokine), growth factor, clotting factor, or lipoprotein. A peptide or polypeptide (e.g., a protein, e.g., a hormone, growth factor, clotting factor or coagulation factor, antibody molecule, enzyme, cytokine, cytokine receptor, or a chimeric protein including cytokines or a cytokine receptor) produced by an engineered cell can have a naturally occurring amino acid sequence, or may contain a variant of the naturally occurring sequence. The variant can be a naturally occurring or non-naturally occurring amino acid substitution, mutation, deletion or addition relative to the reference naturally occurring sequence. The naturally occurring amino acid sequence may be a polymorphic variant. The naturally occurring amino acid sequence can be a human or a non-human amino acid sequence. In some embodiments, the naturally occurring amino acid sequence or naturally occurring variant thereof is a human sequence. In addition, a peptide or polypeptide (e.g., a protein) for use with the present invention may be modified in some way, e.g., via chemical or enzymatic modification (e.g., glycosylation, phosphorylation). In some embodiments, the peptide has about 2, 3, 4, 5, 6, 7, 8, 9, 10, 12, 14, 16, 18, 20, 25, 30, 35, 40, 45, or 50 amino acids. In some embodiments, the protein has an average molecular weight of 5 kD, 10 kD, 25 kD, 50 kD, 100 kD, 150 kD, 200 kD, 250 kD, 500 kD, or more.

In some embodiments, the protein is a hormone. Exemplary hormones include anti-diuretic hormone (ADH), oxytocin, growth hormone (GH), prolactin, growth hormone-releasing hormone (GHRH), thyroid stimulating hormone (TSH), thyrotropin-release hormone (TRH), adrenocorticotropic hormone (ACTH), follicle-stimulating hormone (FSH), luteinizing hormone (LH), luteinizing hormone-releasing hormone (LHRH), thyroxine, calcitonin, parathyroid hormone, aldosterone, cortisol, epinephrine, glucagon, insulin, estrogen, progesterone, and testosterone. In some embodiments, the protein is insulin (e.g., insulin A-chain, insulin B-chain, or proinsulin). In some embodiments, the protein is a growth hormone, such as human growth hormone (hGH), recombinant human growth hormone (rhGH), bovine growth hormone, methione-human growth hormone, des-phenylalanine human growth hormone, and porcine growth hormone.

In some embodiments, the protein is a growth factor, e.g., vascular endothelial growth factor (VEGF), nerve growth factor (NGF), platelet-derived growth factor (PDGF), fibroblast growth factor (FGF), epidermal growth factor (EGF), transforming growth factor (TGF), and insulin-like growth factor-I and -II (IGF-I and IGF-II).

In some embodiments, the protein is a clotting factor or a coagulation factor, e.g., a blood clotting factor or a blood coagulation factor. In some embodiments, the protein is a protein involved in coagulation, i.e., the process by which blood is converted from a liquid to solid or gel. Exemplary clotting factors and coagulation factors include Factor I (e.g., fibrinogen), Factor II (e.g., prothrombin), Factor III (e.g., tissue factor), Factor V (e.g., proaccelerin, labile factor), Factor VI, Factor VII (e.g., stable factor, proconvertin), Factor VIII (e.g., antihemophilic factor A), Factor VIIIC, Factor IX (e.g., antihemophilic factor B), Factor X (e.g., Stuart-Prower factor), Factor XI (e.g., plasma thromboplastin antecedent), Factor XII (e.g., Hagerman factor), Factor XIII (e.g., fibrin-stabilizing factor), von Willebrand factor, prekallikrein, heparin cofactor II, high molecular weight kininogen (e.g., Fitzgerald factor), antithrombin III, and fibronectin. In some embodiments, the protein is an anti-clotting factor, such as Protein C.

In some embodiments, the protein is an antibody molecule. As used herein, the term "antibody molecule" refers to a protein, e.g., an immunoglobulin chain or fragment thereof, comprising at least one immunoglobulin variable domain sequence. The term "antibody molecule" includes, for example, a monoclonal antibody (including a full-length antibody which has an immunoglobulin Fc region). In an embodiment, an antibody molecule comprises a full-length antibody, or a full-length immunoglobulin chain. In an embodiment, an antibody molecule comprises an antigen binding or functional fragment of a full-length antibody, or a full-length immunoglobulin chain. In an embodiment, an antibody molecule is a monospecific antibody molecule and binds a single epitope, e.g., a monospecific antibody molecule having a plurality of immunoglobulin variable domain sequences, each of which binds the same epitope. In an embodiment, an antibody molecule is a multispecific antibody molecule, e.g., it comprises a plurality of immunoglobulin variable domains sequences, wherein a first immunoglobulin variable domain sequence of the plurality has binding specificity for a first epitope and a second immunoglobulin variable domain sequence of the plurality has binding specificity for a second epitope. In an embodiment, the first and second epitopes are on the same antigen, e.g., the same protein (or subunit of a multimeric protein). In an embodiment, a multispecific antibody molecule comprises a third, fourth or fifth immunoglobulin variable domain. In an embodiment, a multispecific antibody molecule is a bispecific antibody molecule, a trispecific antibody molecule, or tetraspecific antibody molecule.

Various types of antibody molecules may be produced by the encapsulated engineered cells, including whole immunoglobulins of any class, fragments thereof, and synthetic proteins containing at least the antigen binding variable domain of an antibody. The antibody molecule can be an antibody, e.g., an IgG antibody, such as $IgG_1$, $IgG_2$, $IgG_3$, or $IgG_4$. An antibody molecule can be in the form of an antigen binding fragment including a Fab fragment, $F(ab')_2$ fragment, a single chain variable region, and the like. Antibodies can be polyclonal or monoclonal (mAb). Monoclonal antibodies may include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they specifically bind the target antigen and/or exhibit the desired biological activity. In some embodiments, the antibody molecule is a single-domain antibody (e.g., a nanobody). The described antibodies can also be modified by recombinant means, for example by deletions, additions or substitutions of amino acids, to increase efficacy of the antibody in mediating the desired function. Exemplary antibodies include anti-beta-galactosidase, anti-collagen, anti-CD14, anti-CD20, anti-CD40, anti-HER2, anti-IL-1, anti-IL-4, anti-IL6, anti-IL-13, anti-IL17, anti-IL18, anti-IL-23, anti-IL-28, anti-IL-29, anti-IL-33, anti-EGFR, anti-VEGF, anti-CDF, anti-flagellin, anti-IFN-α, anti-IFN-β, anti-IFN-γ, anti-mannose receptor, anti-VEGF, anti-TLR1, anti-TLR2, anti-TLR3, anti-TLR4, anti-TLR5, anti-TLR6, anti-TLR9, anti-PDF, anti-PD1, anti-PDL-1, or anti-nerve growth factor antibody. In some embodiments, the antibody is an anti-nerve growth factor antibody (e.g., fulranumab, fasinumab, tanezumab).

In some embodiments, the protein is a cytokine or a cytokine receptor, or a chimeric protein including cytokines or their receptors, including, for example tumor necrosis factor alpha and beta, their receptors and their derivatives, renin; lipoproteins; colchicine; corticotrophin; vasopressin; somatostatin; lypressin; pancreozymin; leuprolide; alpha-1-antitrypsin; atrial natriuretic factor; lung surfactant; a plasminogen activator other than a tissue-type plasminogen activator (t-PA), for example a urokinase; bombesin; thrombin; enkephalinase; RANTES (regulated on activation normally T-cell expressed and secreted); human macrophage inflammatory protein (MIP-1-alpha); a serum albumin such as human serum albumin; mullerian-inhibiting substance; relaxin A-chain; relaxin B-chain; prorelaxin; mouse gonadotropin-associated peptide; chorionic gonadotropin; a microbial protein, such as beta-lactamase; DNase; inhibin; activin; receptors for hormones or growth factors; integrin; protein A or D; rheumatoid factors; platelet-derived growth factor (PDGF); epidermal growth factor (EGF); transforming growth factor (TGF) such as TGF-α and TGF-β, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; an interferon such as interferon-alpha (e.g., interferon.alpha.2A), -beta, -gamma, -lambda and consensus interferon; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; transport proteins; homing receptors; addressins; fertility inhibitors such as the prostaglandins; fertility promoters; regulatory proteins; antibodies (including fragments thereof) and chimeric proteins, such as immunoadhesins; precursors, derivatives, prodrugs and analogues of these compounds, and pharmaceutically acceptable salts of these compounds, or their precursors, derivatives, prodrugs and analogues. Suitable proteins or peptides may be native or recombinant and include, e.g., fusion proteins.

Examples of a polypeptide (e.g., a protein) produced by hydrogel capsule encapsulated cells also include CCL1, CCL2 (MCP-1), CCL3 (MIP-1α), CCL4 (MIP-1β), CCL5 (RANTES), CCL6, CCL7, CCL8, CCL9 (CCL10), CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CXCL1 (KC), CXCL2 (SDF1a), CXCL3, CXCL4, CXCL5, CXCL6, CXCL7, CXCL8 (IL8), CXCL9, CXCL10, CXCL11, CXCL12, CXCL13, CXCL14, CXCL15, CXCL16, CXCL17, CX3CL1, XCL1, XCL2, TNFA, TNFB (LTA), TNFC (LTB), TNFSF4, TNFSF5 (CD40LG), TNFSF6, TNFSF7, TNFSF8, TNFSF9, TNFSF10, TNFSF11, TNFSF13B, EDA, IL2, IL15, IL4, IL13, IL7, IL9, IL21, IL3, IL5, IL6, IL11, IL27, IL30, IL31, OSM, LIF, CNTF, CTF1, IL12a, IL12b, IL23, IL27, IL35, IL14, IL16, IL32, IL34, IL10, IL22, IL19, IL20, IL24, IL26, IL29, IFNL1, IFNL2, IFNL3, IL28, IFNA1, IFNA2, IFNA4, IFNA5, IFNA6, IFNA7, IFNA8, IFNA10, IFNA13, IFNA14, IFNA16, IFNA17, IFNA21, IFNB1, IFNK, IFNW1, IFNG, IL1A (IL1F1), IL1B (IL1F2), IL1Ra (IL1F3), IL1F5 (IL36RN), IL1F6 (IL36A), IL1F7 (IL37), IL1F8 (IL36B), IL1F9 (IL36G), IL1F10 (IL38), IL33 (IL1F1), IL18 (IL1G), IL17, KITLG, IL25 (IL17E), CSF1 (M-CSF), CSF2 (GM-CSF), CSF3 (G-CSF), SPP1, TGFB1, TGFB2, TGFB3, CCL3L1, CCL3L2, CCL3L3, CCL4L1, CCL4L2, IL17B, IL17C, IL17D, IL17F, AIMP1 (SCYE1), MIF, Areg, BC096441, Bmp1, Bmp10, Bmp15, Bmp2, Bmp3, Bmp4, Bmp5, Bmp6, Bmp7, Bmp8a, Bmp8b, C1qtnf4, Ccl21a, Ccl27a, Cd70, Cer1, Cklf, Clcf1, Cmtm2a, Cmtm2b, Cmtm3, Cmtm4, Cmtm5, Cmtm6, Cmtm7, Cmtm8, Crlf1, Ctf2, Ebi3, Edn1, Fam3b, Fasl, Fgf2, Flt3l, Gdf10, Gdf11, Gdf15, Gdf2, Gdf3, Gdf5, Gdf6, Gdf7, Gdf9, Gm12597, Gm13271, Gm13275, Gm13276, Gm13280, Gm13283, Gm2564, Gpi1, Grem1, Grem2, Grn, Hmgb1, Ifna11, Ifna12, Ifna9, Ifnab, Ifne, Il17a, Il23a, Il25, Il31, Iltifb, Inhba, Lefty1, Lefty2, Mstn, Nampt, Ndp, Nodal, Pf4, Pglyrp1, Prl7d1, Scg2, Scgb3a1, Slurp1, Spp1, Thpo, Tnfsf10, Tnfsf11, Tnfsf12, Tnfsf13, Tnfsf13b, Tnfsf14, Tnfsf15, Tnfsf18, Tnfsf4, Tnfsf8, Tnfsf9, Tslp, Vegfa, Wnt1, Wnt2, Wnt5a, Wnt7a, Xcl1, epinephrine, melatonin, triiodothyronine, a prostaglandin, a leukotriene, prostacyclin, thromboxane, islet amyloid polypeptide, mullerian inhibiting factor or hormone, adiponectin, corticotropin, angiotensin, vasopressin, arginine vasopressin, atriopeptin, brain natriuretic peptide, calcitonin, cholecystokinin, cortistatin, enkephalin, endothelin, erythropoietin, follicle-stimulating hormone, galanin, gastric inhibitory polypeptide, gastrin, ghrelin, glucagon, glucagon-like peptide-1, gonadotropin-releasing hormone, hepcidin, human chorionic gonadotropin, human placental lactogen, inhibin, somatomedin, leptin, lipotropin, melanocyte stimulating hormone, motilin, orexin, oxytocin, pancreatic polypeptide, pituitary adenylate cyclase-activating peptide, relaxin, renin, secretin, somatostatin, thrombopoietin, thyrotropin, thyrotropin-releasing hormone, vasoactive intestinal peptide, androgen, alpha-glucosidase (also known as acid maltase), glycogen phosphorylase, glycogen debrancher enzyme, phosphofructokinase, phosphoglycerate kinase, phosphoglycerate mutase, lactate dehydrogenase, carnitine palmityl transferase, carnitine, and myoadenylate deaminase.

In some embodiments, the protein is a replacement therapy or a replacement protein. In some embodiments, the replacement therapy or replacement protein is a clotting factor or a coagulation factor, e.g., Factor VIII (e.g., comprises a naturally occurring human Factor VIII amino acid sequence or a variant thereof) or Factor IX (e.g., comprises a naturally occurring human Factor IX amino acid sequence or a variant thereof).

In some embodiments, the cell is engineered to express a human Factor VIII protein, e.g., a recombinant Factor VIII. In some embodiments, the recombinant Factor VIII is a B-domain-deleted recombinant Factor VIII (FVIII-BDD). In some embodiments, the engineered cell is derived from a human RPE cell line and comprises an exogenous nucleic acid sequence which encodes the FVIII-BDD amino acid sequence shown in FIG. 9 (SEQ ID NO:1).

In some embodiments, the cell is engineered to express a Factor IX, e.g., a wild-type human Factor IX (FIX), such as that shown in FIG. 10 (SEQ ID NO:2) or a polymorphic variant thereof (e.g., alanine substituted for threonine at amino acid position 148 of SEQ ID NO:2). In some embodiments, the cell is engineered to express a gain-in-function (GIF) variant of a wild-type FIX protein (FIX-GIF), wherein the GIF variant has higher specific activity than the corresponding wild-type FIX. In some embodiments, the engineered cell is derived from a human RPE cell line and comprises an exogenous nucleic acid sequence which encodes SEQ ID NO:2, except for having an amino acid substituted for arginine at a position corresponding to amino acid position 338 of SEQ ID NO:2. In some embodiments, the substituting amino acid at a position corresponding to amino acid position 338 of SEQ ID NO:2 is alanine, asparagine, aspartic acid, cysteine, glutamic acid, glutamine, histidine, leucine, lysine, or tyrosine. In some embodiments, the substituting amino acid at a position corresponding to amino acid position 338 of SEQ ID NO:2 is leucine (R338L), and the resulting gain-in-function variant is also known as FIX-Padua.

In some embodiments, the replacement therapy or replacement protein is an enzyme, e.g., alpha-galactosidase, alpha-L-iduronidase (IDUA), or N-sulfoglucosamine sulfohydrolase (SGSH). In some embodiments, the replacement therapy or replacement protein is an enzyme, e.g., an alpha-galactosidase A (e.g., comprises a naturally-occurring human alpha-galactosidase A amino acid sequence or a variant thereof). In some embodiments, the replacement therapy or replacement protein is a cytokine or an antibody.

In some embodiments, the therapeutic agent is a sugar, e.g., monosaccharide, disaccharide, oligosaccharide, or polysaccharide. In some embodiments, a sugar comprises a triose, tetrose, pentose, hexose, or heptose moiety. In some embodiments, the sugar comprises a linear monosaccharide or a cyclized monosaccharide. In some embodiments, the sugar comprises a glucose, galactose, fructose, rhamnose, mannose, arabinose, glucosamine, galactosamine, sialic acid, mannosamine, glucuronic acid, galactosuronic acid, mannuronic acid, or guluronic acid moiety. In some embodiments, the sugar is attached to a protein (e.g., an N-linked glycan or an O-linked glycan). Exemplary sugars include glucose, galactose, fructose, mannose, rhamnose, sucrose, ribose, xylose, sialic acid, maltose, amylose, inulin, a fructooligosaccharide, galactooligosaccharide, a mannan, a lectin, a pectin, a starch, cellulose, heparin, hyaluronic acid, chitin, amylopectin, or glycogen. In some embodiments, the therapeutic agent is a sugar alcohol.

In some embodiments, the therapeutic agent is a lipid. A lipid may be hydrophobic or amphiphilic, and may form a tertiary structure such as a liposome, vesicle, or membrane or insert into a liposome, vesicle, or membrane. A lipid may comprise a fatty acid, glycerolipid, glycerophospholipid, sterol lipid, prenol lipid, sphingolipid, saccharolipid, polyketide, or sphingolipid. Examples of lipids produced by the encapsulated cells include anandamide, docosahexaenoic acid, aprostaglandin, a leukotriene, a thromboxane, an eicosanoid, a triglyceride, a cannabinoid, phosphatidylcholine, phosphatidylethanolamine, a phosphatidylinositol, a phosohatidic acid, a ceramide, a sphingomyelin, a cerebroside, a ganglioside, estrogen, androsterone, testosterone, cholesterol, a carotenoid, a quinone, a hydroquinone, or a ubiquinone.

In some embodiments, the therapeutic agent is a small molecule. A small molecule may include a natural product produced by a cell. In some embodiments, the small molecule has poor availability or does not comply with the Lipinski rule of five (a set of guidelines used to estimate whether a small molecule will likely be an orally active drug in a human; see, e.g., Lipinski, C. A. et al (2001) *Adv Drug Deliv* 46:2-36). Exemplary small molecule natural products include an anti-bacterial drug (e.g., carumonam, daptomycin, fidaxomicin, fosfomycin, ispamicin, micronomicin sulfate, miocamycin, mupiocin, netilmicin sulfate, teicoplanin, thienamycin, rifamycin, erythromycin, vancomycin), an anti-parasitic drug (e.g., artemisinin, ivermectin), an anti-cancer drug (e.g., doxorubicin, aclarubicin, aminolaevulinic acid, arglabin, omacetaxine mepesuccinate, paclitaxel, pentostatin, peplomycin, romidepsin, trabectdin, actinomycin D, bleomycin, chromomycin A, daunorubicin, leucovorin, neocarzinostatin, streptozocin, trabectedin, vinblastine, vincristine), anti-diabetic drug (e.g., voglibose), a central nervous system drug (e.g., L-dopa, galantamine, zicontide), a statin (e.g., mevastatin), an anti-fungal drug (e.g., fumagillin, cyclosporin), 1-deoxynojirimycin, and theophylline, sterols (cholesterol, estrogen, testerone). Additional small molecule natural products are described in Newman, D. J. and Cragg, M. (2016) *J Nat Prod* 79:629-661 and Butler, M. S. et al (2014) *Nat Prod Rep* 31:1612-1661, which are incorporated herein by reference in their entirety.

In some embodiments, the encapsulated cells are engineered to synthesize a non-protein or non-peptide small molecule. For example, in an embodiment an engineered cell can produce a statin (e.g., taurostatin, pravastatin, fluvastatin, or atorvastatin).

In some embodiments, the therapeutic agent is an antigen (e.g., a viral antigen, a bacterial antigen, a fungal antigen, a plant antigen, an environmental antigen, or a tumor antigen). An antigen is recognized by those skilled in the art as being immunostimulatory, i.e., capable of stimulating an immune response or providing effective immunity to the organism or molecule from which it derives. An antigen may be a nucleic acid, peptide, protein, sugar, lipid, or a combination thereof.

The encapsulated cells may produce a single therapeutic agent or a plurality of therapeutic agents. The plurality of therapeutic agents may be related or may form a complex. In some embodiments, the therapeutic agent secreted or released from an encapsulated cell is in an active form. In some embodiments, the therapeutic agent is secreted or released from an encapsulated cell in an inactive form, e.g., as a prodrug. In the latter instance, the therapeutic agent may be activated by a downstream agent, such as an enzyme.

ENUMERATED EXEMPLARY EMBODIMENTS

1. A process for preparing a hydrogel capsule composition from a polymer solution which comprises at least one afibrotic hydrogel-forming polymer and optionally an unmodified hydrogel-forming polymer, the process comprising contacting a plurality of droplets of the polymer solution with an aqueous cross-linking solution for a period of time sufficient to produce hydrogel capsules, wherein the cross-linking solution comprises a cross-linking agent, a buffer, an osmolarity-adjusting agent and a process additive, wherein the process additive is an amphiphilic compound or a surfactant or reduces the surface tension of the cross-linking solution.

2. The process of embodiment 1, wherein at least 95% of the hydrogel capsules in the capsule composition are spherical capsules.

3. The process of embodiment 1 or 2, wherein the process additive is a surfactant.

4. The process of embodiment 3, wherein the surfactant is a non-ionic surfactant.

5. The process of embodiment 4, wherein the surfactant is a polysorbate-type surfactant, a copolymer of polyoxyethylene (POE) and polyoxypropylene (PPO), or a polyethylene oxide-polypropylene oxide-polyethylene oxide (PEO-PPO-PEO) triblock copolymer.

6. The process of embodiment 5, wherein the surfactant is a polyethylene oxide-polypropylene oxide-polyethylene oxide (PEO-PPO-PEO) triblock copolymer and has a hydrophilic-lipophilic balance (HLB) of at least 18 or at least 24.

7. The process of embodiment 6, wherein the surfactant has an HLB of at least 24 and an average molecular weight of 7680 g/mole to 9510 g/mole.

8. The process of any one of embodiments 1 to 7, wherein the process additive is selected from the group consisting of: polysorbate 20, polysorbate 80, poloxamer 188, poloxamer 407, 4-(1,1,3,3-Tetramethylbutyl)phenyl-polyethylene glycol and octylphenoxypolyethoxyethanol.

9. The process of embodiment 8, wherein the process additive is poloxamer 188.

10. The process of any one of embodiments 3 to 9, wherein the surfactant is present in the cross-linking solution at a concentration of at least about 0.001%.

11. The process of embodiment 10, wherein the concentration of the surfactant is 0.001% to about 0.1%, about 0.005% to about 0.05%, about 0.005% to about 0.01%, or about 0.01% to about 0.05%.

12. The process of any one of the above embodiments, wherein the cross-linking agent comprises divalent cations of a single type or a mixture of different types.

13. The process of embodiment 12, wherein the cross-linking agent comprises one or more of $Ba^{2+}$, $Ca^{2+}$ and $Sr^{2+}$.

14. The process of embodiment 13, wherein the cross-linking agent is selected from the group consisting of:
   a. $BaCl_2$ at a concentration of 1 mM to 100 mM or 7.5 mM to 20 mM;
   b. $CaCl_2$) at a concentration of 50 mM to 100 mM;
   c. $SrCl_2$ at a concentration of 37.5 mM to 100 mM;
   d. a mixture of $BaCl_2$ at a concentration of 5 mM to 20 mM and $CaCl_2$) at a concentration of 37.5 mM to 12.5 mM; and
   e. a mixture of $BaCl_2$ at a concentration of 5 mM to 20 mM and $SrCl_2$ at a concentration of 37.5 mM to 12.5 mM.

15. The process of any one of the above embodiments, wherein the buffer comprises 4-(2-hydroxyethyl)-1-piperazineethanesulfonic acid) (HEPES).

16. The process of any one of the above embodiments, wherein the osmolarity-adjusting agent comprises mannitol at a concentration of 0.1 M to 0.3 M.

17. The process of any of the above embodiments, wherein the cross-linking agent is not $SrCl_2$.

18. The process of any one of the above embodiments, wherein the cross-linking agent is $BaCl_2$.

19. The process of any one of the above embodiments, wherein the cross-linking solution comprises 25 mM HEPES buffer, 20 mM $BaCl_2$, 0.2 M mannitol and 0.01% poloxamer 188.

20. The process of any one of embodiments 1 to 16, wherein the cross-linking agent is $SrCl_2$ and the process additive is a surfactant at a concentration of about 0.01%, wherein the surfactant is polysorbate 80.

21. The process embodiment 20, wherein the cross-linking solution comprises 50 mM strontium chloride hexahydrate, 0.165 M mannitol, 25 mM HEPES and 0.01% of polysorbate 80.

22. The process of any one of the above embodiments, wherein the polymer solution comprises both of the afibrotic hydrogel-forming polymer and the unmodified hydrogel-forming polymer.

23. The process of any one of the above embodiments, wherein the afibrotic hydrogel-forming polymer comprises a compound of any of Formula (I), Formula (I-a), Formula (II), Formula (II-a), Formula (II-b), Formula (II-c), Formula (II-d), Formula (III), Formula (III-a), Formula (IV), Formula (IV-a), Formula (IV-b), each as defined herein, or a salt of any of said compounds.

24. The process of any one of the above embodiments, wherein the afibrotic hydrogel-forming polymer comprises an alginate.

25. The process of any one of the above embodiments, wherein the unmodified polymer comprises an alginate.

26. The process of embodiment 24 or 25, wherein the viscosity of the polymer solution is 21.3 cP to 925.5 cP.

27. The process of any one of the above embodiments, wherein the afibrotic hydrogel-forming polymer is chemically modified with one or more of the Compounds shown in Table 2.

28. The process of any one of the above embodiments, wherein the afibrotic hydrogel-forming polymer does not comprise Compound 100 shown in Table 2.

29. The process of any one of the above embodiments, wherein the afibrotic hydrogel-forming polymer is chemically modified with Compound 112, Compound 113 or Compound 114 shown in Table 2.

30. The process of any one of the above embodiments, wherein the afibrotic hydrogel-forming polymer is chemically modified with Compound 114 shown in Table 2.

31. The process of any one of the above embodiments, wherein the process additive is not polysorbate 20.

32. The process of any one of the above embodiments, wherein the polymer solution further comprises a cell suspension comprising a plurality of cells.

33. The process of embodiment 32, wherein the cell suspension comprises single cells, one or more spheroids, or cells bound to one or more microcarriers.

34. The process of embodiment 32 or 33, wherein the cell suspension comprises single cells and the concentration of single cells in the polymer solution is at least about 20 million cells/mL, or the cell suspension comprises spheroids, and the concentration of single cells in the polymer solution is at least about 40 million cells/mL.

35. The process of any one of embodiments 32 to 34, wherein the cells are epithelial cells, endothelial cells, fibroblast cells, mesenchymal stem cells, keratinocyte cells, induced pluripotent stem cells (iPSCs) or the cells are derived from epithelial cells, endothelial cells, fibroblast cells, mesenchymal stem cells, keratinocyte cells or iPSCs.

36. The process of any one of embodiments 32 to 35, wherein the cells are derived from RPE cells (e.g., derived from ARPE-19) cells.

37. The process of embodiment 36, wherein the concentration of single cells in the polymer solution is at least any of 30, 40, 50, 75 or 100 million cells/ml.

38. The process of any one of embodiments 32 to 37, wherein the cells are not islet cells.

39. The process of any one of the above embodiments, wherein each of the droplets in the plurality has an approximately equal volume that is selected to produce a hydrogel millicapsule.

40. The process of any one of the above embodiments, wherein the process additive reduces the surface tension of the cross-linking solution.

41. The process of embodiment 40, wherein the process additive reduces the surface tension of the cross-linking solution by about 1%, about 2.5%, about 5%, about 7.5%, about 10%, about 15%, about 20%, about 25%, about 30%, about 35%, about 40%, about 45%, about 50%, about 55%, about 60%, about 70%, about 75%, or more.

42. The process of embodiment 40, wherein the process additive reduces the surface tension of the cross-linking solution between about 1-10%, about 1-25%, about 5-50%, about 5-25%, about 5-10%, about 10-50%, or about 10-25%.

43. The process of any one of the above embodiments, wherein the process further comprises separating the hydrogel capsules from the cross-linking solution and washing the separated hydrogel capsules one or more times with a buffered aqueous solution.

44. A composition produced by the process of any of the above embodiments.

45. The composition of embodiment 44, which comprises a population of hydrogel capsules having one or more of the following characteristics:
   a. less than 10%, less than 5%, less than 2% or less than 1% of the capsules in the population have a capsule defect;
   b. at least 95%, at least 98% or at least 99% of the capsules in the composition are spherical capsules having a diameter that is within about 20%, 15% or 15% of the desired size;
   c. comprises at least 220 spherical hydrogel capsules per mL;
   d. at least 98% of the hydrogel capsules in the population are spherical capsules and at least about 90% of the spherical capsules contain at least 2,500, 5,000, 7,500, 10,000 cells, at least 20,000 cells, at least 25,000 cells, at least 30,000 cells, at least 35,000 cells or at least 40,000 cells; and
   e. all the spherical capsules in the population have a smooth surface.

46. The composition of embodiment 44 or 45, which comprises a detectable amount of the process additive.

47. A composition comprising spherical hydrogel capsules encapsulating cells, wherein the hydrogel capsules comprise an afibrotic polymer in the hydrogel and at least 95%, 97% or at least 99% of the capsules are spherical and each of the spherical capsules contains at least 2,500, 5,000, 7,500, or 10,000 cells (e.g., engineered RPE cells).

48. The composition of any one of embodiments 44 to 47, wherein all the capsules in the composition comprise a smooth surface.

49. The composition of embodiment 47 or 48, which comprises a surfactant, wherein molecules of the surfactant are disposed on or within surfaces of hydrogel capsules.

50. The composition of embodiment 49, wherein the surfactant is poloxamer 188.

51. The composition of any one of embodiments 44 to 48, wherein the hydrogel is cross-linked with barium chloride.

52. The composition of embodiment 49, wherein the hydrogel is cross-linked with strontium chloride and the surfactant is polysorbate 80.

53. The composition of any one of embodiments 44-52, wherein the afibrotic polymer is chemically modified with one or more of the Compounds shown in Table 2.

54. The composition of embodiment 53, wherein the afibrotic polymer is chemically modified with Compound 114 shown in Table 2.

55. The composition of embodiment 53, wherein the Compound is not Compound 100 shown in Table 2.

56. The composition of embodiment 53, wherein the afibrotic polymer is chemically modified with Compound 112 or Compound 113 shown in Table 2.

57. The composition of any one of embodiments 44-56, wherein the surfactant is not polysorbate 20.

EXAMPLES

Example 1: Synthesis of Exemplary Afibrotic Compounds

Described herein are synthetic protocols for exemplary afibrotic compounds used to modify a polymer described herein. Note the compound numbers refer to the precursors of the compounds in Table 2 (e.g., as the compounds in Table 2 are shown linked to a polymer described herein).

Huisgen Cycloaddition to Afford 1,4-Substituted Triazoles

The copper-catalyzed Huisgen [3+2] cycloaddition was used to prepare triazole-based compounds and compositions thereof. The scope and typical protocols have been the subject of many reviews (e.g., Meldal, M. and Tornoe, C. W. *Chem. Rev.* (2008) 108:2952-3015; Hein, J. E. and Fokin, V. V. *Chem. Soc. Rev.* (2010) 39(4):1302-1315; both of which are incorporated herein by reference).

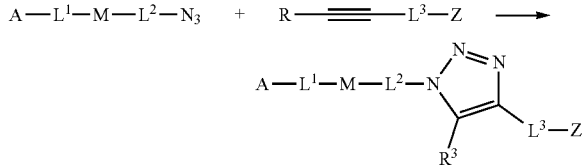

In the example shown above, the azide is the reactive moiety in the fragment containing the connective element A, while the alkyne is the reactive component of the pendant group Z. As depicted below, these functional handles can be exchanged to produce a structurally related triazole product. The preparation of these alternatives is similar, and do not require special considerations.

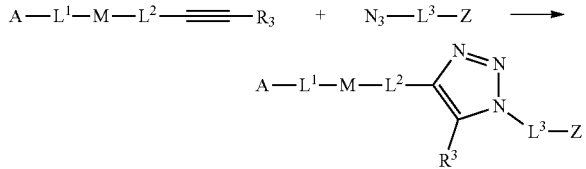

A typical Huisgen cycloaddition procedure starting with an iodide is outlined below. In some instances, iodides are transformed into azides during the course of the reaction for safety.

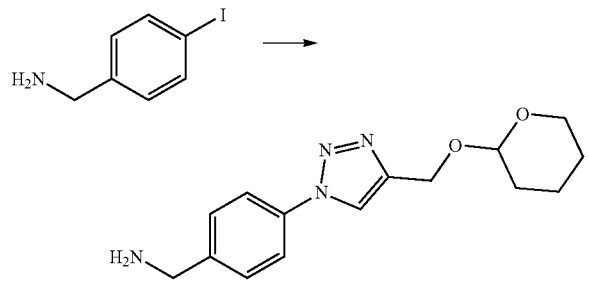

A solution of sodium azide (1.1 eq), sodium ascorbate, (0.1 eq) trans-N,N'-dimethylcyclohexane-1,2-diamine (0.25 eq), copper (I) iodide in methanol (1.0 M, limiting reagent) was degassed with bubbling nitrogen and treated with the acetylene (1 eq) and the aryl iodide (1.2 eq). This mixture was stirred at room temperature for 5 minutes, then warmed to 55° C. for 16 h. The reaction was then cooled to room temperature, filtered through a funnel, and the filter cake washed with methanol. The combined filtrates were concentrated and purified via flash chromatography on silica gel (120 g silica, gradient of 0 to 40% (3% aqueous ammonium hydroxide, 22% methanol, remainder dichloromethane) in dichloromethane to afford the desired target material.

A typical Huisgen cycloaddition procedure starting with an azide is outlined below.

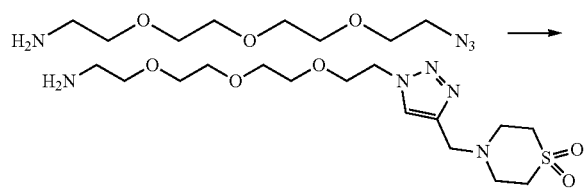

A solution of tris[(1-benzyl-1H-1,2,3-triazol-4-yl)methyl] amine (0.2 eq), triethylamine (0.5 eq), copper (I) iodide (0.06 eq) in methanol (0.4 M, limiting reagent) was treated with the acetylene (1.0 eq) and cooled to 0° C. The reaction was allowed to warm to room temperature over 30 minutes, then heated to 55° C. for 16 h. The reaction was cooled to room temperature, concentrated, and purified with HPLC (C18 column, gradient of 0 to 100% (3% aqueous ammonium hydroxide, 22% methanol remainder dichloromethane) in dichloromethane to afford the desired target material.

Huisgen Cycloaddition to Afford 1,5-Substituted Triazoles

The Huisgen [3+2] cycloaddition was also performed with ruthenium catalysts to obtain 1,5-disubstituted products preferentially (e.g., as described in Zhang et al, *J. Am. Chem. Soc.*, 2005, 127, 15998-15999; Boren et al, *J. Am. Chem. Soc.*, 2008, 130, 8923-8930, each of which is incorporated herein by reference in its entirety).

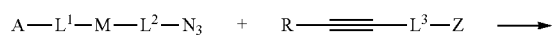

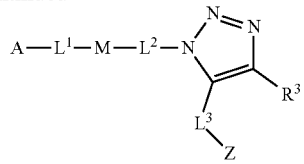

As described previously, the azide and alkyne groups may be exchanged to form similar triazoles as depicted below.

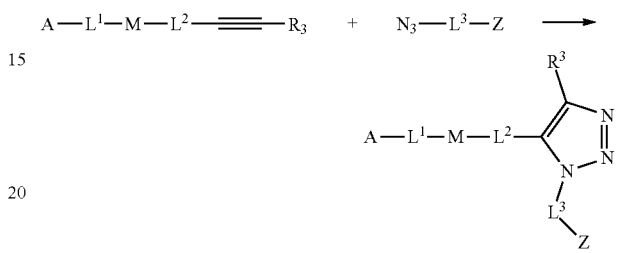

A typical procedure is described as follows: a solution of the alkyne (1 eq) and the azide (1 eq) in dioxane (0.8M) were added dropwise to a solution of pentamethylcyclo-pentadienylbis(triphenylphosphine) ruthenium(II) chloride (0.02 eq) in dioxane (0.16M). The vial was purged with nitrogen, sealed and the mixture heated to 60° C. for 12 h. The resulting mixture was concentrated and purified via flash chromatography on silica gel to afford the requisite compound.

General Protocol A for 1,3-Dipolar Cycloaddition

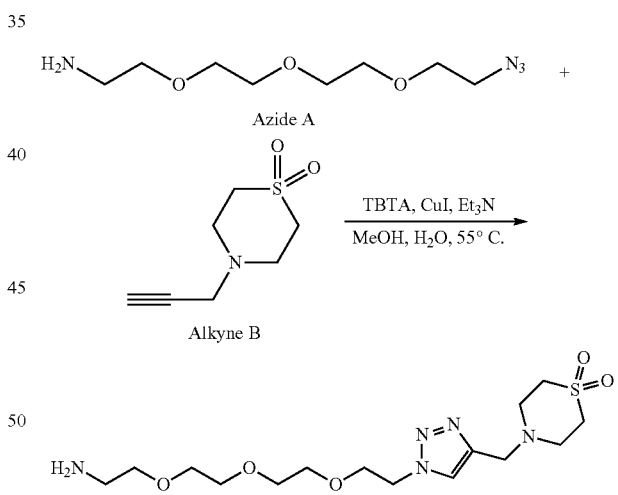

To a solution of dimethyl-(2-methylsulfonylethyl)-prop-2-ynyl-ammonium (Alkyne B, 6.3 g, 28.86 mmol, 1 eq), TBTA (3.83 g, 7.22 mmol, 0.25 eq), copper iodide (550 mg, 2.89 mmol, 0.1 eq), and triethylamine (TEA, 1.01 mL, 7.22 mmol, 0.25 eq) in methanol (50 mL) and water (12 mL) were purged with a stream of nitrogen for 5 minutes and cooled with an ice bath. 2-[2-[2-(2-azidoethoxy)ethoxy] ethoxy]ethanamine (Azide A, 5.0 g, 28.86 mmol, 1 eq) was added and the mixture was stirred at room temperature for 5 minutes and then heated to 55° C. overnight. The reaction mixture was cooled to room temperature and filtered. The solvent was removed under reduced pressure and the residue was purified over silica gel to afford 4-((1-(2-(2-(2-(2- aminoethoxy)ethoxy)ethoxy)ethyl)-1H-1,2,3-triazol-4-yl)methyl)thiomorpholine 1,1-dioxide (Compound 101, 8.0 g, 71%) as an oil. MS ESI [M+H]⁺=392.2

A similar procedure was used to prepare the following compounds:

| Compound Number | M⁺ + H Observed or 1H NMR Data |
| --- | --- |
| 110 | 241.2 |
| 107 | 303.2 |
| 117 | 304.1 |
| 119 | 436.2 |
| 118 | 348.2 |
| 120 | 394.2 |
| 121 | 406.2 (M⁺ +Na) |
| 114 | 213.1 |

General Protocol B for 1,3-Dipolar Cycloaddition

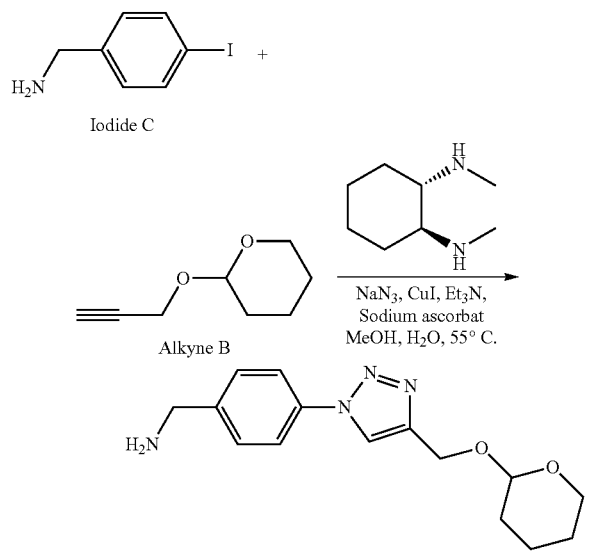

A mixture of (4-iodophenyl)methanamine (Iodide C, 5.0 g, 18.55 mmol, 1.0 eq), (1S,2S)—N1,N2-dimethylcyclohexane-1,2-diamine (0.59 mL, 3.71 mmol, 0.2 eq), sodium ascorbate (368 mg, 1.86 mmol, 0.1 eq), copper iodide (530 mg, 2.78 mmol, 0.15 eq), sodium azide (2.41 g, 37.1 mmol, 2.0 eq), Et₃N (3.11 mL, 22.26 mmol, 1.2 eq) and 2-(prop-2-yn-1-yloxy)tetrahydro-2H-pyran (Alkyne B, 2.6 g, 18.55 mmol, 1.0 eq) in methanol (50 mL) and water (12 mL) were purged with nitrogen for 5 minutes and heated to 55° C. overnight. The reaction mixture was cooled to room temperature and filtered. The solvent was removed under reduced pressure and the residue was purified over silica gel to afford (4-(4-(((tetrahydro-2H-pyran-2-yl)oxy)methyl)-1H-1,2,3-triazol-1-yl)phenyl)methanamine (Compound 100, 3.54 g, 66%) as a solid. MS ESI [M+H]⁺=289.2.

A similar procedure was used to prepare the following compounds:

| Compound Number | M⁺ + H Observed |
| --- | --- |
| 111 | 261.1 |
| 108 | 303.2 |
| 106 | 303.2 |
| 109 | 357.1 |
| 113 | 287.2 |
| 112 | 307.2 |

Synthesis of Compound 105

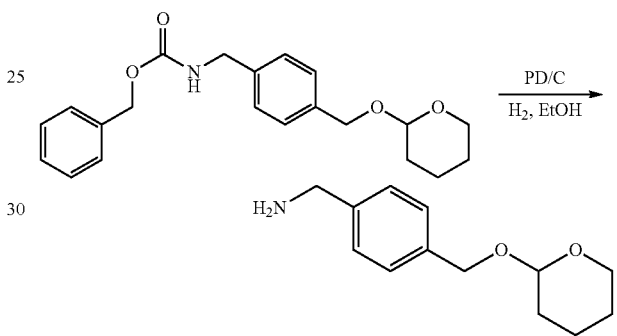

(4-(((tetrahydro-2H-pyran-2-yl)oxy)methyl)benzyl)carbamate (1.5 g, 4.2 mmol, 1 eq) and palladium on carbon (160 mg, 10 wt. %) in EtOH were placed in a flask and briefly evacuated, and then hydrogen was added via a balloon and the mixture was stirred for 1 hour at room temperature. The solvent was removed under reduced pressure and the crude product was purified over silica gel to afford (4-(((tetrahydro-2H-pyran-2-yl)oxy)methyl)-phenyl)methanamine (Compound 105, 890 mg, 95%) as a colorless oil. MS ESI [M+H]⁺=460.2.

General Protocol for Deprotection (General Procedure D)

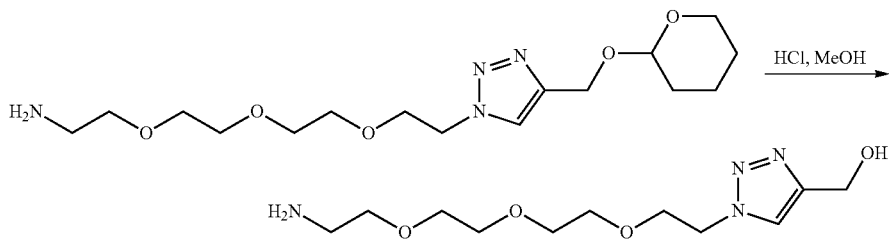

2-(2-(2-(2-(4-(((tetrahydro-2H-pyran-2-yl)oxy)methyl)-1H-1,2,3-triazol-1-yl)ethoxy)ethoxy)ethan-1-amine (1.9 g, 5.3 mmol) was dissolved in HCl (1N in MeOH, 10 mL) and stirred for 90 minutes at room temperature. The solvent was removed under reduced pressure and the residue was purified on silica gel to afford (1-(2-(2-(2-(2-aminoethoxy)ethoxy)ethoxy)ethyl)-1H-1,2,3-triazol-4-yl)methanol (462 mg, 32%) as a colorless oil. MS ESI [M+Na]$^+$=297.2.

A similar procedure was used to prepare the following compounds:

| Compound Number | M$^+$ + H Observed |
|---|---|
| 107 | 205.1 |
| 104 | 273.1 |

Example 2: Preparation of Afibrotic Polymers

A polymeric material may be chemically modified with an afibrotic compound (e.g., a compound of Formula (I) or a salt thereof) prior to formation of hydrogel capsules. Synthetic protocols of exemplary afibrotic compounds are outlined in Example 1. These compounds, or others, may be used to chemically modify any polymeric material. For example, in the case of alginate, the alginate carboxylic acid was activated for coupling to one or more amine-functionalized compounds to achieve an alginate modified with an afibrotic compound, e.g., a compound of Formula (I). The alginate polymer was dissolved in water (30 mL/gram polymer) and treated with 2-chloro-4,6-dimethoxy-1,3,5-triazine (0.5 eq) and N-methylmorpholine (1 eq). To this mixture, a solution of the compound of interest was added in acetonitrile (0.3M). The reaction was warmed to 55° C. for 16 h, then cooled to room temperature and gently concentrated via rotary evaporation. The residue was then dissolved in water. The mixture was filtered through a bed of cyano-modified silica gel (Silicycle) and the filter cake was washed with water. The resulting solution was then dialyzed (10,000 MWCO membrane) against water for 24 hours, replacing the water twice. The resulting solution was concentrated via lyophilization to afford the desired afibrotic alginate.

Example 3: Preparation of Afibrotic Alginate Solutions

An afibrotic alginate (SLG20 alginate (NovaMatrix, Sandvika, Norway, cat. #4202006) chemically modified with Compound 101 in Table 2) was initially dissolved at 5% weight to volume in 0.9% saline and then blended with 3% weight to volume of PRONOVA™ SLG100 (FMC) (also dissolved in 0.9% saline) at a volume ratio of 70% afibrotic alginate to 30% SLG100 or 90% afibrotic alginate to 10% SLG100.

Example 4: Preparation of Cross-Linking Solutions

Crosslinking solutions used in Examples 5 through 11 contained 25 mM HEPES buffer, 20 mM BaCl$_2$, 0.2M mannitol and 0 to 0.01% of a surfactant listed in Table 1 above.

Crosslinking solutions used in Example 12 contained 50 mM strontium chloride hexahydrate, 0.165 M mannitol, 25 mM HEPES and with or without one of the surfactants listed in Table 1 above.

Example 5: Preparation and Quality Evaluation of Hydrogel Capsule Compositions Compositions containing microcapsules (about 300 micrometers in diameter) or millicapsules (about 1.5 millimeters in diameter)) were prepared in a sterile biosafety cabinet as described in Vegas, A., et al., Nature Medicine 22(3):306-311 (2016).

Briefly, a desired volume of a sterile afibrotic alginate solution with or without a suspension of cells (e.g., ARPE-19 cells) was loaded into a syringe and capped with a 30-gauge or 18-gauge blunt tipped needle (SAI Infusion Technologies). When included, the cell suspension was made up of single cells or spheroids. The size of the needle was selected based on the target capsule size: the 30-gauge needle was used to form droplets for the microcapsules and the 18-gauge needle was used to form droplets for the millicapsules. The syringe was placed into a syringe pump oriented vertically above a dish containing the crosslinking buffer. A high voltage power generator was connected to the needle and grounded to the biosafety cabinet.

The syringe pump and power generator were turned on to extrude the alginate solution through the needle using settings pre-determined to achieve a desired droplet rate of alginate solution into cross-linking solution containing no surfactant or a surfactant. After extrusion of the entire volume of the alginate solution, the capsules were cross-linked for five minutes.

Any non-capsular debris on the crosslinking bath surface was counted. Capsules that had fallen to the bottom of the crosslinking vessel were collected by pipetting, leaving any non-capsular debris on the surface behind. After the capsules settled, the crosslinking buffer was removed, and capsules were washed with a HEPES wash buffer (NaCl 15.428 g, KCl 0.70 g, MgCl$_2$*6H$_2$O 0.488 g, 50 ml of HEPES (1 M) buffer solution (Gibco, Life Technologies, California, USA) in 2 L of DiH$_2$O). This wash step was repeated for a total of four washes.

An aliquot of the resulting composition that contained at least 400 capsules was transferred to a well plate and the entire aliquot examined by optical microscopy for quality by counting the number of spherical capsules, capsules with a capsule defect and satellite capsules. In addition, whether the capsules had a smooth or rough surface was noted. Capsule compositions of acceptable quality were stored as follows: microcapsule compositions (empty capsules) were stored at 4° C.; millicapsule compositions (capsules encapsulating cells) were stored in culture medium at 37° C.

Example 6. Properties of Microcapsule Compositions Prepared by Cross-Linking Afibrotic Alginate Hydrogel Droplets in Presence or Absence of Tween® 20

Figure 2:
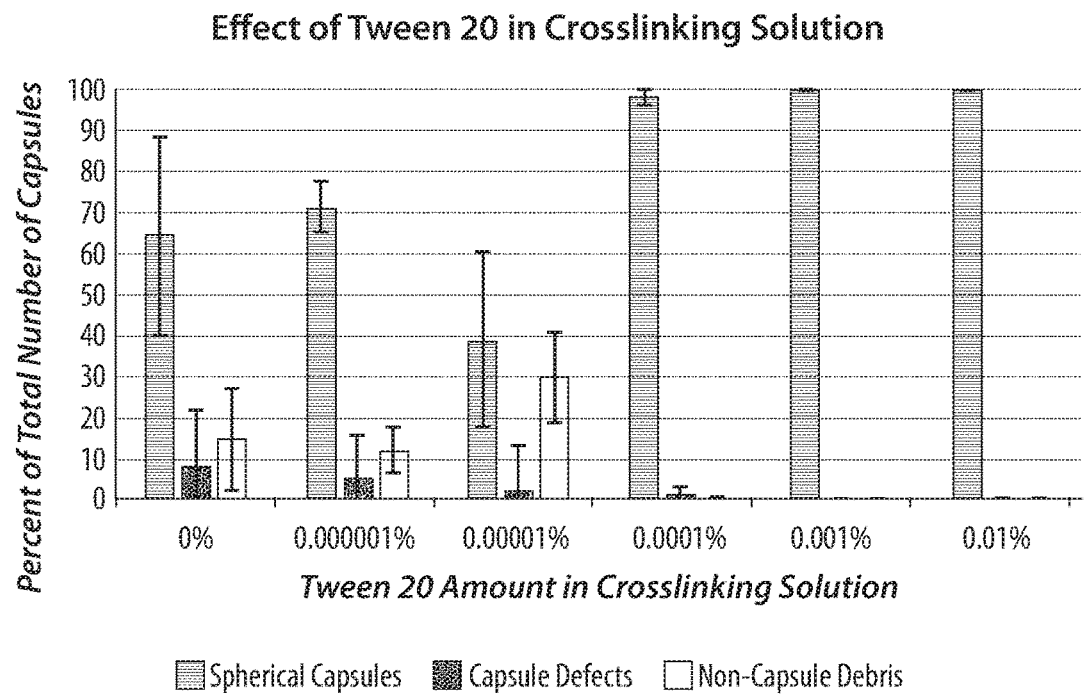
FIG. 2 is a bar graph that illustrates the effect of various concentrations of Tween® 20 in the barium chloride cross-linking solution on the quality of a composition comprising empty alginate hydrogel microcapsules (target size of 300 micrometer (m)) as assessed by the percent of the capsules that are spherical with no observed defects (Spherical Capsules (blue bars)), or with observed defects (Capsule defects (red bars) and Non-capsule debris (grey bars)).

Microcapsule compositions were prepared by extruding droplets of a 70:30 mixture of afibrotic alginate:unmodified alginate into cross-linking solutions with no Tween®20 or with increasing concentrations of Tween 20: 0.000001%, 0.00001%, 0.0001%, 0.001% and 0.01%. The different capsule compositions were examined for quality and the results are shown in FIG. 2.

The inclusion of 0.0001% to 0.01% Tween 20 in the crosslinking solution significantly improved the quality of the microcapsule composition in a dose-dependent manner as compared to the control composition prepared without Tween 20. For compositions prepared using either 0.001% or 0.01% Tween 20 in the cross-linking solution, greater than 99% of the capsules in compositions were spherical microcapsules of the target size and there was no non-capsular debris in the cross-linking bath.

To confirm that Tween 20 did not have a deleterious effect on fibrosis, microcapsules made with and without 0.01%

Figure 3:
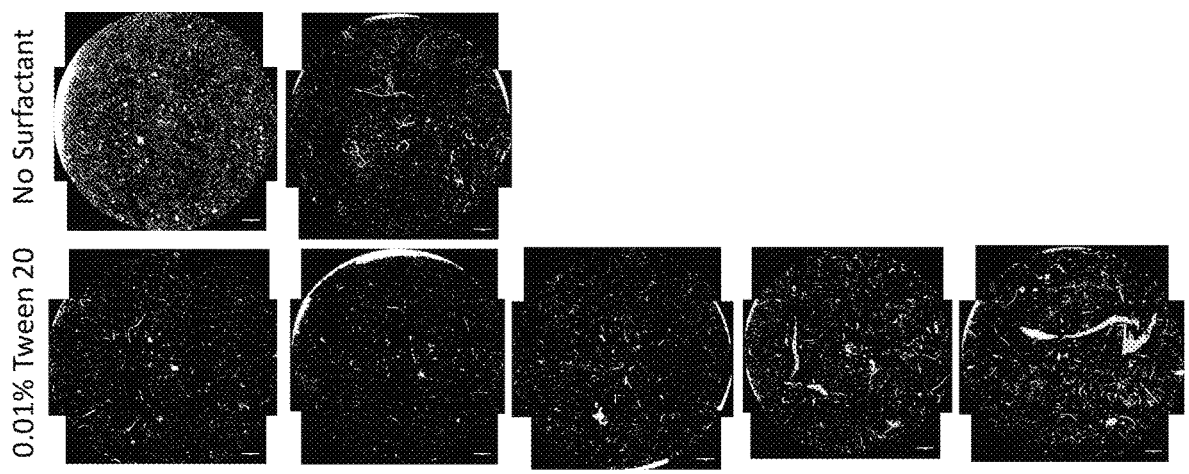
FIG. 3 shows dark field images of empty alginate hydrogel microcapsules (300 micrometer (μm)) prepared without (top panel) or with 0.01% Tween® 20 (bottom panel) in the barium chloride cross-linking solution that were retrieved 14 days after intraperitoneal implant into C57/BL6 mice.

Tween 20 in the cross-linking solution were implanted IP into C57/BL6 mice and retrieved after two weeks. The level of fibrosis was assessed using darkfield imaging as shown in FIG. 3, wherein fibrosis is represented by bright spots on a dark background. As shown, the presence of Tween 20 did not increase the level of fibrosis on the microcapsules.

After 2 weeks implantation in C57/BL6 mice, the capsules with and without Tween 20 had similar morphology and both lacked fibrosis. Therefore, the use of low concentrations of Tween 20 in the crosslinking buffer improves the quality of afibrotic alginate capsule compositions without affecting the afibrotic properties of the capsules.

Example 7. Effect of Tween 20 in Cross-Linking Solution on the Viability of Encapsulated ARPE-19 Cells in Millicapsules Prepared from Afibrotic Alginate Hydrogel Solution To assess the effects of Tween 20 on viability of encapsulated ARPE-19 cells, two experiments were performed using ARPE-19 cells provided as spheroids or single cells.

In the first experiment, millicapsule compositions were prepared by extruding droplets of an afibrotic alginate solution (70:30 afibrotic alginate:unmodified alginate) with a suspension of ARPE-19 spheroids at a loading concentration of 2 million cells/ml into cross-linking solutions with no Tween 20 or with increasing concentrations of Tween 20: 0.0001%, 0.001% and 0.01%.

In the second experiment, millicapsule compositions were prepared by extruding droplets of an afibrotic alginate solution (70:30 afibrotic alginate:unmodified alginate) with a suspension of ARPE-19 single cells at one of three different loading concentrations into cross-linking solutions with 0.01% Tween 20.

Figure 4:
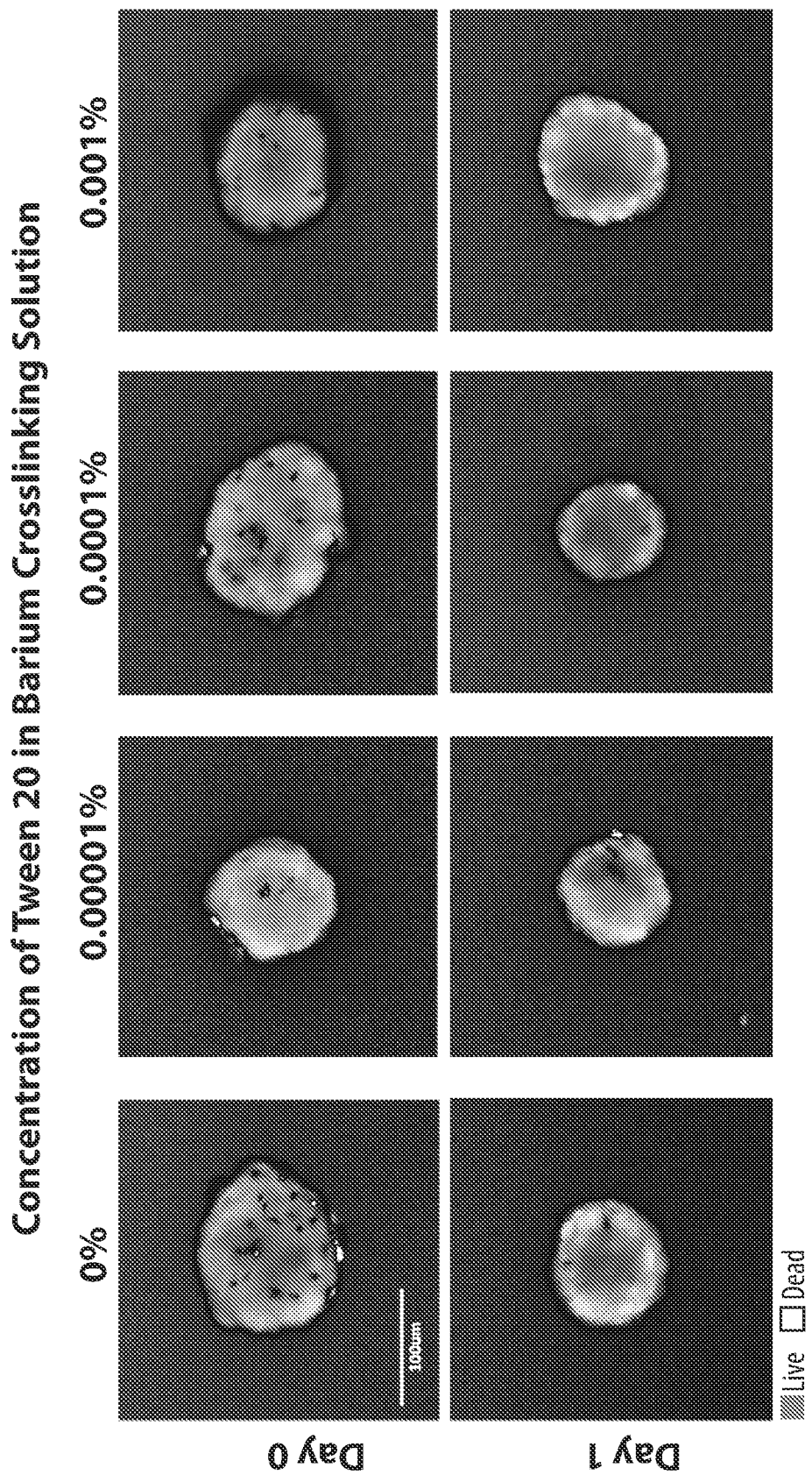
FIG. 4 shows fluorescent images of ARPE-19 cells in representative encapsulated spheroids taken at day 0 or day 1 after preparing a composition of alginate hydrogel millicapsules (about 1.5 mm in diameter) encapsulating ARPE-19 spheroids with or without the indicated concentration of Tween® 20 in the barium chloride crosslinking solution, with live cells identified by green fluorescence (light gray) and dead cells identified by red fluorescence (dark gray).
Figure 5:
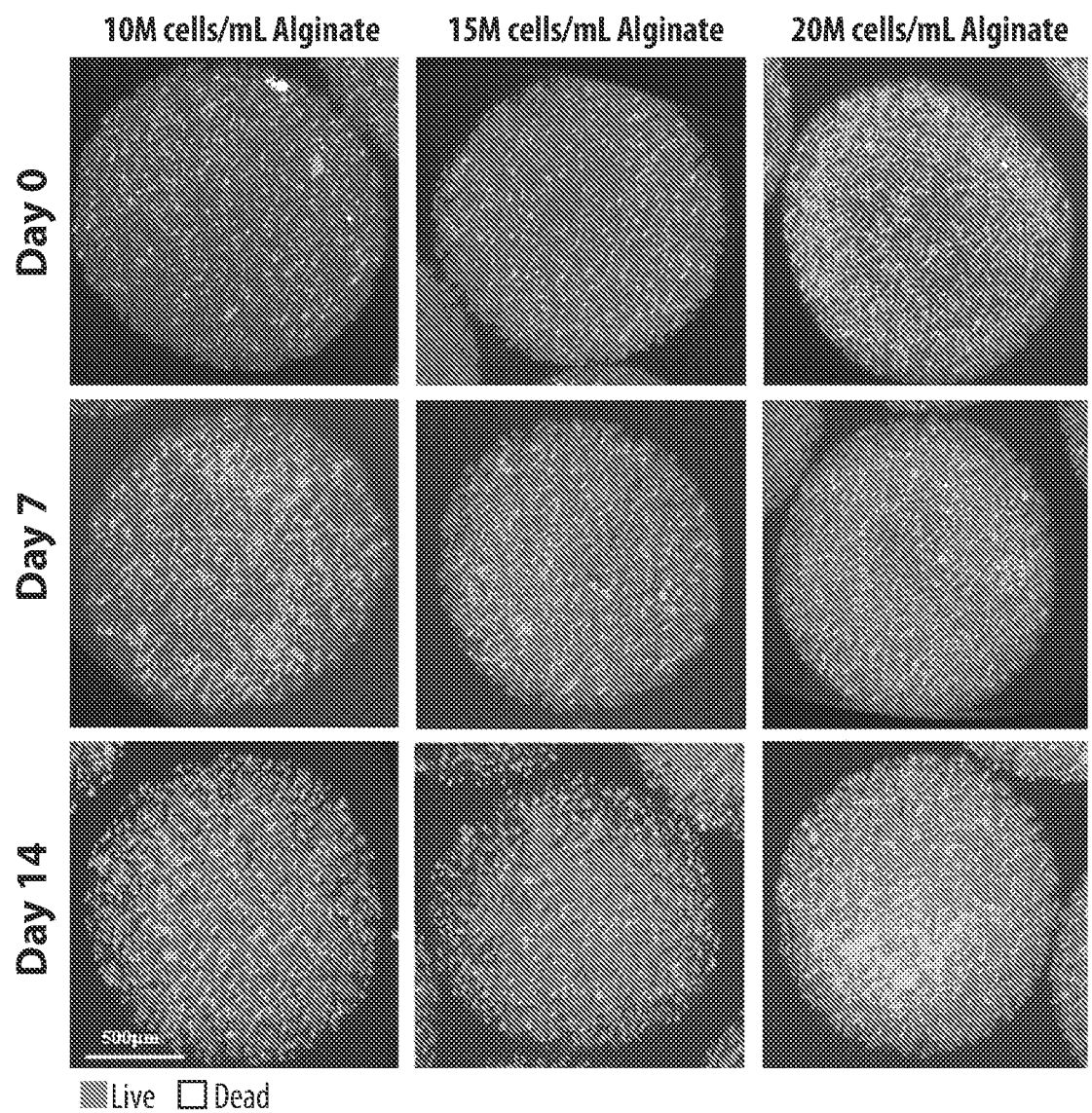
FIG. 5 shows fluorescent images of encapsulated single ARPE-19 cells in representative alginate hydrogel capsules taken at 0, 7 or 14 days after preparing a composition of alginate hydrogel millicapsules (about 1.5 mm in diameter) using an afibrotic alginate solution containing ARPE-19 cells at a concentration of 10, 15 or 20 million (M) cells/mL and 0.01% Tween® 20 in the barium chloride cross-linking solution, with live cells identified by green fluorescence (light gray) and dead cells identified by red fluorescence (dark gray).
Figure 6:
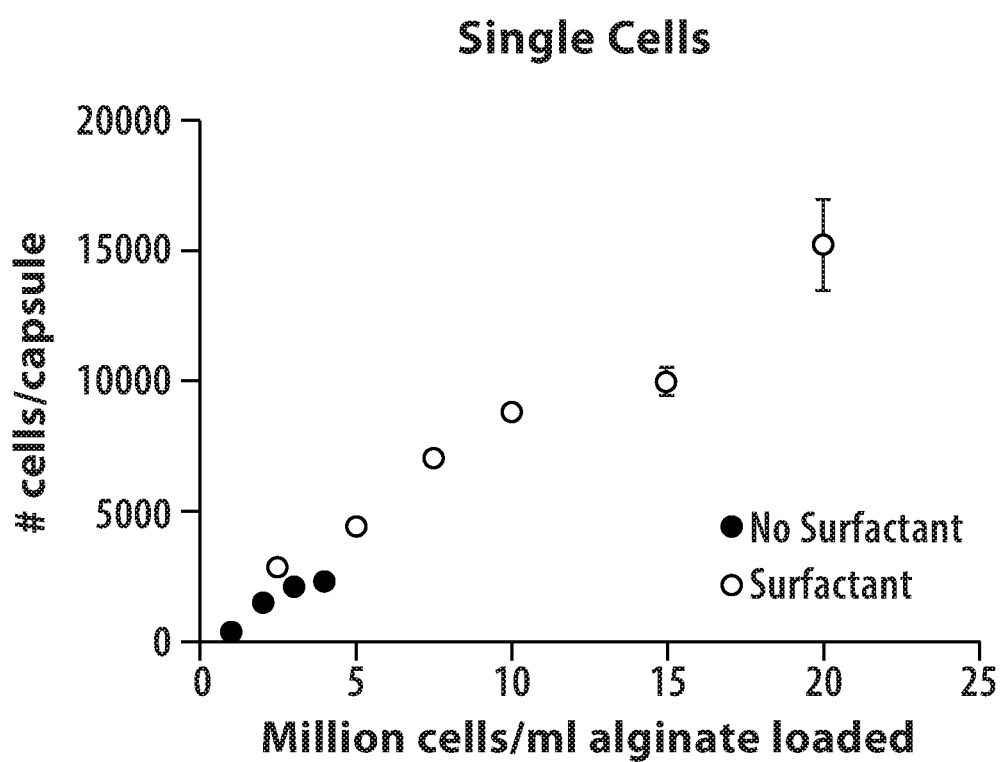
FIG. 6 is a graph showing the number of single RPE cells present per capsule (y-axis) in alginate hydrogel millicapsules (about 1.5 mm in diameter) prepared from alginate mixtures containing increasing concentrations of cells (x-axis) in the absence (black circles) or presence (grey circles) of Tween® 20 in the barium chloride crosslinking buffer.

The resulting millicapsule compositions encapsulating cells were stored at 37 C in culture medium and the viability of the encapsulated cells was evaluated at Day 0 and Day 1 following encapsulation of ARPE-19 spheroids or at Day 0, 7 and 14 following encapsulation of ARPE-19 single cells. Cell viability was assessed using live/dead staining. Briefly, capsules were incubated with 20 um calcein AM and 10 um ethidium homodimer-1 in medium for 30 minutes at 37 C. Staining solution was removed and replaced with fresh medium and stained capsules were imaged immediately using a fluorescence microscope. Representative images of encapsulated spheroids and single cells are shown in FIG. 4 and FIG. 5, respectively.

ARPE19 cell viability was not impacted by the presence of Tween 20 in the crosslinking bath for encapsulated spheroids or single cells. Even at the highest single cell loading of 20 M cells/mL alginate solution, there was no apparent necrotic core in the center of the capsule and high cell viability was maintained for at least 14 days of culture.

Example 8. Effect of Tween 20 in Cross-Linking Solution on Cell-Loading Capacity of Millicapsules Prepared from Afibrotic Alginate Hydrogel Solutions To determine the effect of Tween 20 on cell loading, suspensions of single ARPE-19 cells were encapsulated with and without the presence of 0.01% Tween 20 in the cross-linking solution.

Millicapsule compositions were prepared by extruding droplets of an afibrotic alginate solution (70:30 afibrotic alginate:unmodified alginate) with a suspension of ARPE-19 single cells at 1, 2, 3, 4, 5, 7.5, 10, 15 and 20 million cells/ml alginate into cross-linking solutions with no Tween® 20 or 0.01% Tween® 20. The resulting cell loading was determined by CellTiter Glo the day of encapsulation.

For encapsulation without Tween 20, non-capsule debris was observed at 3 and 4 million cells/ml alginate; above 4 million cells/ml no spherical capsules were formed, and all alginate formed non-capsule debris. With 0.01% Tween 20 in the cross-linking solution, at all cell concentrations tested up to 20 million cells/ml, no non-capsule debris was observed and spherical capsules were formed. The cell loading was increased from 2300 cells/capsule without Tween 20 to 7000 cells/capsule with Tween 20 in the cross-linking solution. Thus, the presence of Tween 20 in the cross-linking solution increases the cell loading achievable per capsule while preventing the formation of non-capsule debris.

Example 9. Comparison of Different Hydrophilic Surfactants in the Cross-Linking Solution An unexpected consequence of cross-linking droplets of afibrotic alginate solution in the presence of Tween 20 was the formation of capsules with a rough capsule surface instead of capsules with smooth surfaces formed in the absence of Tween® 20. Thus, several experiments were performed using microcapsule and millicapsule compositions prepared with various surfactants in the cross-linking solution.

Figure 7:
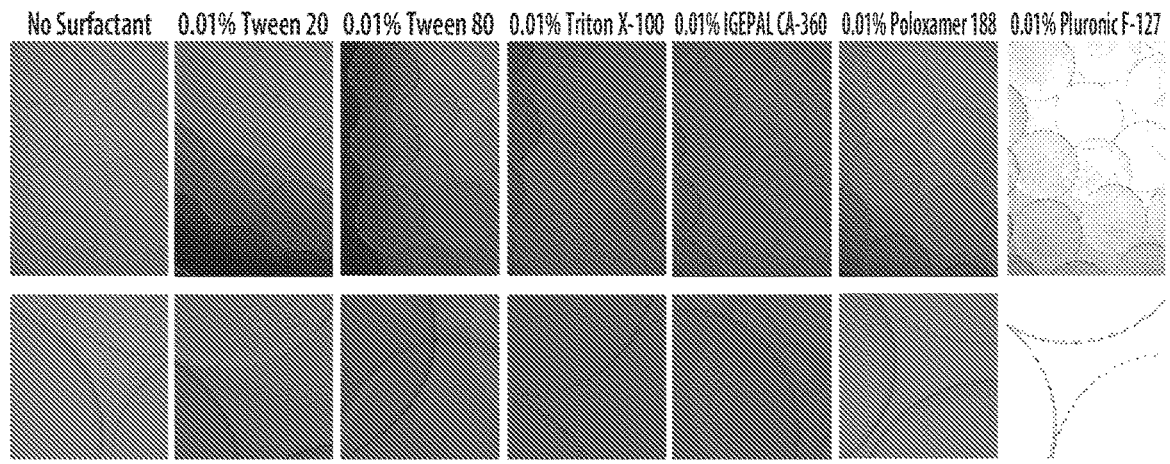
FIG. 7 shows bright field images of empty alginate hydrogel microcapsules (300 micrometer (μm)) made without or with different surfactants in the barium chloride crosslinking bath, with the top panel showing a representative image of several capsules and the bottom panel showing enlarged images of the surfaces of several capsules.

In a first experiment, microcapsule compositions were prepared by extruding droplets of a 70:30 mixture of afibrotic alginate:unmodified alginate into cross-linking solutions with no surfactant or with 0.01% of one of the following surfactants: Tween 20, Tween 80, Triton X-100, IGEPAL CA-630, Poloxamer 188 or Poloxamer 407. Aliquots of the resulting capsule compositions were viewed using optical microscopy to assess characteristics of capsule surfaces. Representative images are shown in FIG. 7. Microcapsules cross-linked in the absence of a surfactant had smooth surfaces, as expected. Surprisingly, out of the six surfactants tested, only the cross-linking solution containing poloxamer 188 generated capsules with comparably smooth surfaces.

In a second experiment, millicapsule compositions were prepared by extruding droplets of an afibrotic alginate solution (70:30 afibrotic alginate:unmodified alginate) with or without 50 million ARPE-19 single cells per ml into cross-linking solutions containing no surfactant or 0.01% of one of the six surfactants. Aliquots of the resulting capsule compositions were examined for various quality properties and the results are shown in Table 3 below.

TABLE 3

Effects of using hydrophilic, non-ionic surfactants in cross-linking solution on capsule compositions prepared from a medium viscosity (240 cP) afibrotic alginate solution[b]

| | Characteristics of Capsule Composition | | | | |
|---|---|---|---|---|---|
| Surfactant[a] | Non-Capsule Debris | Capsule Defects | Satellite Capsules | Smooth Surface[c] | Cell Loading Capacity[d] |
| None | >50% | 5% | 2% | Yes | Low |
| Tween 20 | 0% | 0% | >23% | No | Moderate |
| Tween 80 | 0% | 0% | >23% | No | High |
| Triton X-100 | 0% | 0% | >23% | No | Moderate |
| IGEPAL CA-630 | 0% | 0% | >23% | No | High |

TABLE 3-continued

Effects of using hydrophilic, non-ionic surfactants in cross-linking solution on capsule compositions prepared from a medium viscosity (240 cP) afibrotic alginate solution[b]

| Surfactant[a] | Non-Capsule Debris | Capsule Defects | Satellite Capsules | Smooth Surface[c] | Cell Loading Capacity[d] |
|---|---|---|---|---|---|
| poloxamer 188 | 0% | 0.50% | 0% | Yes | High |
| poloxamer 407 | 0% | 0% | >23% | No | High |

[a]See Table 1 for description of surfactants
[b]70:30 mixture of low molecular weight alginate (SLG100) modified with Compound No. 101 and unmodified high molecular weight alginate (SLG100)
[c]Based on visual inspection under optical microscope at 2x, 4x and 10x magnification
[d]Defined as the ability to make spherical capsules with a smooth surface and no non-capsule debris using a cell loading of 50 million ARPE-19 cells/ml alginate solution.

The presence of non-capsule debris and capsules with defects were essentially eliminated by use of any of the six surfactants in the cross-linking buffer and the capsules had higher loading capacities than capsules generated without a surfactant. Similar results were obtained when millicapsules were prepared from a low viscosity afibrotic alginate solution (90:10 afibrotic alginate:unmodified alginate) (data not shown).

Notably, all but the poloxamer 188 capsule compositions prepared with a surfactant in the cross-linking solution contained a larger number of satellite capsules than the cross-linking solution with no surfactant. Thus, although removal of satellite capsules from a capsule composition can be readily accomplished, it appears that the use of poloxamer 188 as the process additive in the cross-linking solution may eliminate the need for such a step.

Example 10. Effect of Cell Loading Concentration on Morphology of Millicapsules Crosslinked in the Presence of Poloxamer 188

Figure 8:
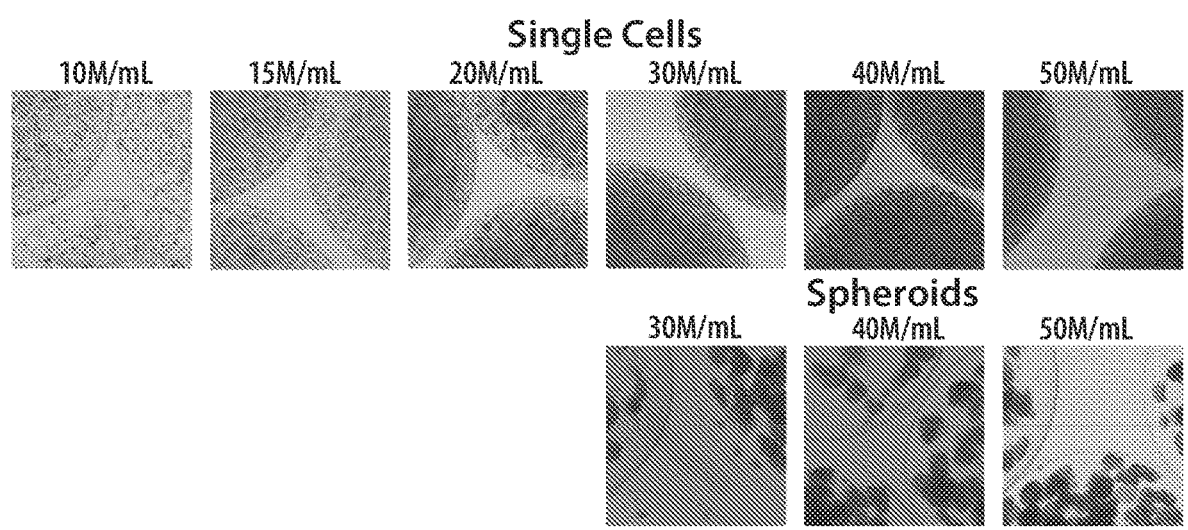
FIG. 8 shows bright field images of alginate hydrogel millicapsules (about 1.5 mm in diameter) encapsulating RPE single cells (top panel) or RPE spheroids (bottom panel) prepared by cross-linking droplets of an alginate mixture containing the indicated concentration of RPE cells in the barium chloride cross-linking solution containing 0.01% poloxamer 188.

Compositions of millicapsules encapsulating single ARPE-19 cells or ARPE-19 spheroids were prepared by extruding droplets of a medium viscosity afibrotic alginate solution (70:30 afibrotic alginate:unmodified alginate) with various cell loading concentrations into cross-linking solutions containing 0.01% of poloxamer 188. Six loading concentrations of 10 million to 50 million cells/mL were used for encapsulating single cells, and three loading concentrations from 30 million to 50 million cells/ml were used for encapsulating spheroids. Aliquots of the resulting capsule compositions were examined by optical microscopy to assess the morphology of the millicapsules, and representative images are shown in FIG. 8.

The results of this experiment showed that cell loading concentrations as high as 50 million cells/mL alginate solution (as single cells or as spheroids) had minimal impact on capsule morphology when the millicapsules were cross-linked in the presence of 0.01% poloxamer 188. In contrast, the morphology of millicapsules cross-linked without a surfactant is significantly impacted at cell-loading concentrations greater than about 5 million cells/mL alginate solution (data not shown). Thus, use of poloxamer 188 in the cross-linking solution can allow at least a 10-fold increase in the number of encapsulated cells.

Other experiments using the same medium-viscosity afibrotic alginate solution, a cell-loading concentration of 20 million single ARPE-19 cells/mL alginate solution and 0.01% poloxamer in the cross-linking solution demonstrated that millicapsule compositions encapsulating single ARPE-19 cells can be prepared in which at least about 95% of the capsules in the composition are spherical capsules having an average number of at least about 12,000 cells per capsule (data not shown).

Another set of experiments using the same medium-viscosity afibrotic alginate solution, a cell-loading concentration of 40 million cells/mL alginate solution and 0.01% poloxamer in the cross-linking solution demonstrated that millicapsule compositions encapsulating ARPE-19 spheroids can be prepared in which at least about 95% of the capsules in the composition are spherical capsules having an average number of at least about 8,200 cells per capsule (data not shown).

Example 11: Effect of Surfactant on Capsule Strength Ex Vivo

Compositions of hydrogel millicapsules of about 1.5 mm in diameter were prepared by extruding droplets of the medium viscosity afibrotic alginate solution described in Example 3 into a cross-linking solution with no poloxamer 188 or with poloxamer 188 at a concentration of 0.0001%, 0.001% or 0.01%. Aliquots of the different capsule compositions were implanted IP into C57/BL6 mice and were retrieved after 1 month.

Upon retrieval, capsules were examined for integrity and mechanical strength was measured by determining initial fracture with a texture analyzer. All capsules showed similar integrity (data not shown) and all capsule compositions had similar initial fracture values, regardless of the presence or absence of poloxamer 188 (FIG. 11).

Figure 12:
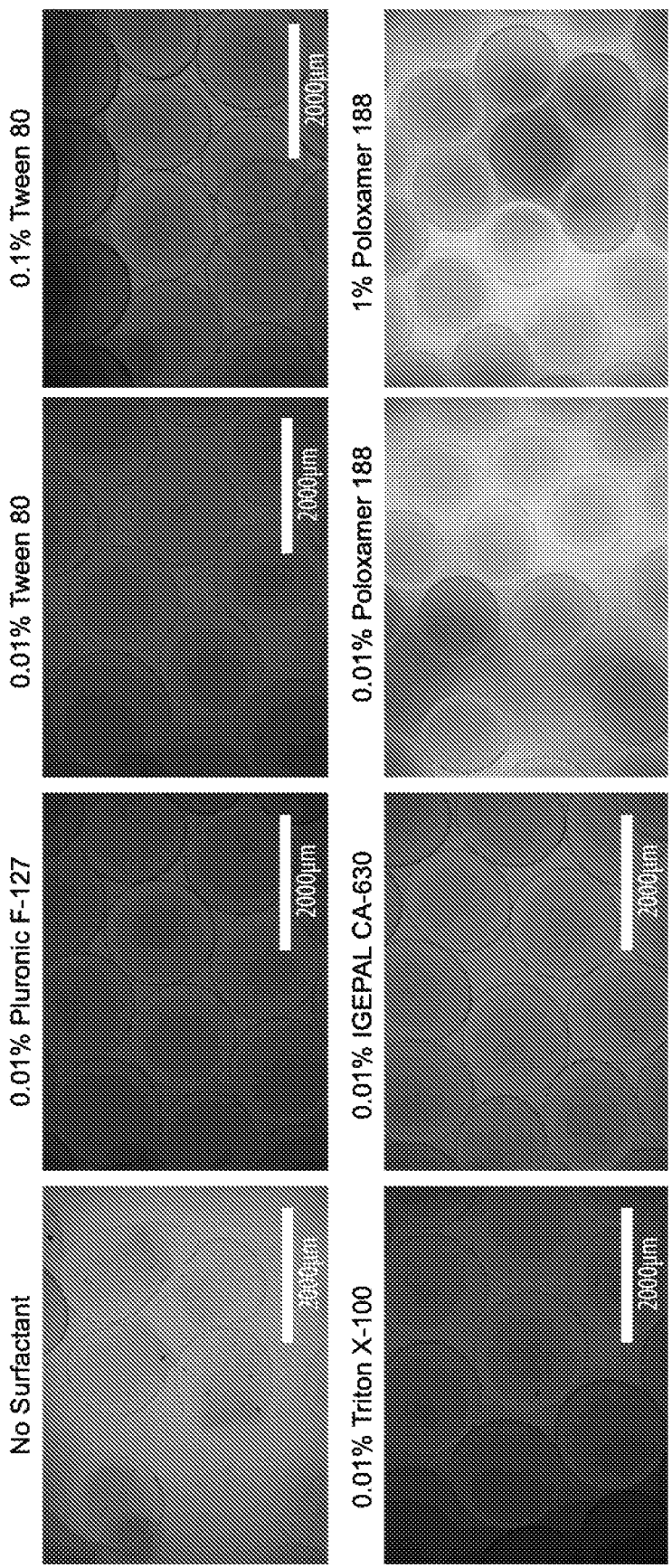
FIG. 12 shows bright field images of empty alginate hydrogel millicapsules (about 1.5 mm in diameter) made without or with different surfactants in the strontium chloride cross-linking solution.

Example 12: Effect of Various Surfactants on Strontium-Crosslinked Hydrogel Capsules Compositions of empty two-compartment hydrogel millicapsules of about 1.5 mm diameter were prepared as follows. An electrostatic droplet generator was set up as follows: an UltraVolt HV-Rack-2-250-00411 was connected to the top and bottom of a coaxial needle (inner lumen of 22G, outer lumen of 18G, Ramd-Hart Instrument Co., Succasunna, N.J., USA). The inner lumen was attached to a first 5-ml Luer-lock syringe (BD, NJ, USA), which was connected to a syringe pump (Pump 11 Pico Plus, Harvard Apparatus, Holliston, Mass., USA) that was oriented vertically. The outer lumen was connected via a luer coupling to a second 5-ml Luer-lock syringe which was connected to a second syringe pump (Pump 11 Pico Plus) that was oriented horizontally. The medium viscosity alginate solution described in Example 3 was placed in each of the syringes. The single droplets containing polymer solution from both syringes were extruded through both lumens of the coaxial needle into a glass dish containing the strontium chloride cross-linking solution described in Example 3 with no surfactant or with one of the following surfactants: 0.01% Pluronic F-127 (poloxamer 407), 0.01% IGEPAL CA-630, 0.01% Triton X-100, 0.01% Tween 80, 0.1% Tween 80, 0.01% poloxamer 188, and 1% poloxamer 188. The different hydrogel capsule compositions were examined for morphology and representative images are shown in FIG. 12.

The morphology of the strontium cross-linked capsules was optimal in the presence of 0.01% Tween 80, where uniform, smooth, spherical capsules were formed. An increased concentration of Tween 80 (0.1%) appeared to degrade the morphology, resulting in rough edges on the capsules. Hydrogel capsules prepared with 0.01% poloxamer 188 in the crosslinking bath, which is optimal for barium crosslinked capsules, were non-spherical with significant surface roughness. However, capsule morphology improved when poloxamer 188 was included in the strontium cross-linking solution at 1%.

EQUIVALENTS AND SCOPE

This application refers to various issued patents, published patent applications, journal articles, and other publications, all of which are incorporated herein by reference in their entirety. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, Figures, or Examples but rather is as set forth in the appended claims. Those of ordinary skill in the art will appreciate that various changes and modifications to this description may be made without departing from the spirit or scope of the present invention, as defined in the following claims.

The invention claimed is:

1. A process for preparing a hydrogel capsule composition from an alginate polymer solution,
   wherein the alginate polymer solution comprises an afibrotic hydrogel-forming alginate polymer and an unmodified hydrogel-forming alginate polymer,
   wherein the process comprises contacting a plurality of droplets of the alginate polymer solution with an aqueous cross-linking solution for a period of time sufficient to produce hydrogel capsules,
   wherein the cross-linking solution comprises a cross-linking agent comprising a divalent cation, a buffer, an osmolarity-adjusting agent and a surfactant,
   wherein the surfactant is a poly (ethylene oxide)-poly (propylene oxide)-poly (ethylene oxide) PEO-PPO-PEO) triblock copolymer; and
   wherein the alginate polymer solution further comprises a cell suspension comprising a plurality of cells.

2. The process of claim 1, wherein the surfactant reduces the surface tension of the cross-linking solution by about 1%, or more.

3. The process of claim 1, wherein at least 95% of the hydrogel capsules prepared are spherical capsules.

4. The process of claim 1, wherein the surfactant is selected from the group consisting of: poloxamer 188, and poloxamer 407.

5. The process of claim 1, wherein the cross-linking agent is selected from the group consisting of:
   a) $BaCl_2$ at a concentration of 1 mM to 100 mM;
   b) $CaCl_2$ at a concentration of 50 mM to 100 mM;
   c) $SrCl_2$ at a concentration of 37.5 mM to 100 mM;
   d) a mixture of $BaCl_2$ at a concentration of 5 mM to 20 mM and $CaCl_2$ at a concentration of 37.5 mM to 12.5 mM; and
   e) a mixture of $BaCl_2$ at a concentration of 5 mM to 20 mM and $SrCl_2$ at a concentration of 37.5 mM to 12.5 mM.

6. The process of claim 5, wherein the surfactant is poloxamer 188 and the cross-linking agent is $BaCl_2$ at a concentration of 1 mM to 100 mM.

7. The process of claim 6, wherein the cross-linking solution comprises 25 mM HEPES buffer, 20 mM $BaCl_2$, 0.2M mannitol and poloxamer 188.

8. The process of claim 5, wherein the cross-linking agent is $SrCl_2$ at a concentration of 37.5 mM to 100 mM.

9. The process of claim 8, wherein the cross-linking solution comprises 50 mM strontium chloride hexahydrate, 0.165 M mannitol, and 25 mM HEPES.

10. The process of claim 1, wherein the afibrotic hydrogel-forming polymer comprises a compound of Formula (I):

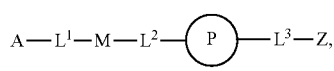

(I)

or a salt thereof, wherein:

A is alkyl, alkenyl, alkynyl, heteroalkyl, cycloalkyl, heterocyclyl, aryl, heteroaryl, —O—, —C(O)O—, —C(O)—, —OC(O)—, —N($R^C$)—, —N($R^C$)C(O)—, —C(O)N($R^C$)—, —N($R^C$)C(O)($C_1$-$C_6$-alkylene)-, —N($R^C$)C(O)($C_1$-$C_6$-alkenylene)-, —N($R^C$)N($R^D$)—, —NCN—, —C(=N($R^C$)($R^D$))O—, —S—, —S(O)$_x$—, —OS(O)$_x$—, —N($R^C$)S(O)$_x$, —S(O)$_x$N($R^C$)—, —P($R^F$)$_y$—, —Si(O$R^A$)$_2$—, —Si($R^G$)(O$R^A$)—, —B(O$R^A$)—, or a metal, each of which is optionally linked to an attachment group and is optionally substituted by one or more $R^1$;

each of $L^1$ and $L^3$ is independently a bond, alkyl, or heteroalkyl, wherein each alkyl and heteroalkyl is optionally substituted by one or more $R^2$;

$L^2$ is a bond;

M is absent, alkyl, heteroalkyl, cycloalkyl, heterocyclyl, aryl, or heteroaryl, each of which is optionally substituted by one or more $R^3$;

P is absent, cycloalkyl, heterocycyl, or heteroaryl, each of which is optionally substituted by one or more $R^4$;

Z is hydrogen, alkyl, alkenyl, alkynyl, heteroalkyl, —O$R^A$, —C(O)$R^A$, —C(O)O$R^A$, —C(O)N($R^C$)($R^D$), —N($R^C$)C(O)$R^A$, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted by one or more $R^5$;

each $R^A$, $R^B$, $R^C$, $R^D$, $R^E$, $R^F$, and $R^G$ is independently hydrogen, alkyl, alkenyl, alkynyl, heteroalkyl, halogen, azido, cycloalkyl, heterocyclyl, aryl, or heteroaryl, wherein each alkyl, alkenyl, alkynyl, heteroalkyl, cycloalkyl, heterocyclyl, aryl, and heteroaryl is optionally substituted with one or more $R^6$;

or $R^C$ and $R^D$, taken together with the nitrogen atom to which they are attached, form a ring, optionally substituted with one or more $R^6$;

each $R^1$, $R^2$, $R^3$, $R^4$, $R^5$, and $R^6$ is independently alkyl, alkenyl, alkynyl, heteroalkyl, halogen, cyano, azido, oxo, —O$R^{41}$, —C(O)O$R^{41}$, —C(O)$R^{B1}$, —OC(O)$R^{B1}$, —N($R^{C1}$)($R^{D1}$), —N($R^{C1}$)C(O)$R^{B1}$, —C(O)N($R^{C1}$), S$R^{E1}$, S(O)$_x$$R^{E1}$, —OS(O)$_x$$R^{E1}$, —N($R^{C1}$)S(O)$_x$$R^{E1}$, —S(O)$_x$N($R^{C1}$)($R^{D1}$), —P($R^{F1}$)$_y$, cycloalkyl, heterocyclyl, aryl, heteroaryl, wherein each alkyl, alkenyl, alkynyl, heteroalkyl, cycloalkyl, heterocyclyl, aryl, and heteroaryl is optionally substituted by one or more $R^7$;

each $R^{41}$, $R^{B1}$, $R^{C1}$, $R^{D1}$, $R^{E1}$, and $R^{F1}$ is independently hydrogen, alkyl, alkenyl, alkynyl, heteroalkyl, cycloalkyl, heterocyclyl, aryl, or heteroaryl, wherein each alkyl, alkenyl, alkynyl, heteroalkyl, cycloalkyl, heterocyclyl, aryl, heteroaryl is optionally substituted by one or more $R^7$;

each $R^7$ is independently alkyl, alkenyl, alkynyl, heteroalkyl, halogen, cyano, oxo, hydroxyl, cycloalkyl, or heterocyclyl;

x is 1 or 2; and y is 2, 3, or 4.

11. The process of claim 10, wherein the compound of Formula (I) is a compound of (II)

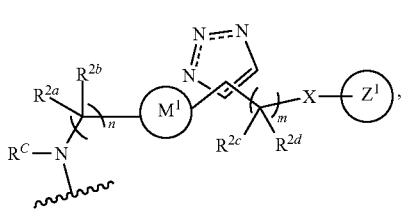

(II)

or a salt thereof, wherein Ring $M^1$ is cycloalkyl, heterocyclyl, aryl, or heteroaryl, each of which is optionally substituted with 1-5 $R^3$; Ring $Z^1$ is cycloalkyl, heterocyclyl, aryl or heteroaryl, optionally substituted with 1-5 $R^5$; each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl, or each of $R^{2a}$ and $R^{2b}$ or $R^{2c}$ and $R^{2d}$ is taken together to form an oxo group; X is O or absent, $N(R^{10})(R^{11})$ O, or S; $R^C$ is hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, or heteroaryl is optionally substituted with 1-6 $R^6$; each $R^3$, $R^5$, and $R^6$ is independently alkyl, alkenyl, alkynyl, heteroalkyl, halogen, cyano, azido, oxo, —$OR^{A1}$, —$C(O)OR^{A1}$, —$C(O)R^{B1}$, —$OC(O)R^{B1}$, —$N(R^{C1})(R^{D1})$, —$N(R^{C1})C(O)R^{B1}$, —$C(O)N(R^{C1})$, $SR^{E1}$, cycloalkyl, heterocyclyl, aryl, or heteroaryl; each of $R^{10}$ and $R^{11}$ is independently hydrogen, alkyl, alkenyl, alkynyl, heteroalkyl, —$C(O)OR^{A1}$, —$C(O)R^{B1}$, —$OC(O)R^{B1}$, —$C(O)N(R^{C1})$, cycloalkyl, heterocyclyl, aryl, or heteroaryl; each $R^{A1}$, $R^{B1}$, $R^{C1}$, $R^{D1}$, and $R^{E1}$ is independently hydrogen, alkyl, alkenyl, alkynyl, heteroalkyl, cycloalkyl, heterocyclyl, aryl, or heteroaryl, wherein each of alkyl, alkenyl, alkynyl, heteroalkyl, cycloalkyl, heterocyclyl, aryl, heteroaryl is optionally substituted with 1-6 $R^7$; each $R^7$ is independently alkyl, alkenyl, alkynyl, heteroalkyl, halogen, cyano, oxo, hydroxyl, cycloalkyl, or heterocyclyl; each m and n is independently 1, 2, 3, 4, 5, or 6; and "～～" refers to a connection to an attachment group or the hydrogel-forming polymer.

12. The process of claim 10, wherein the compound of Formula (I) is a compound of Formula (III):

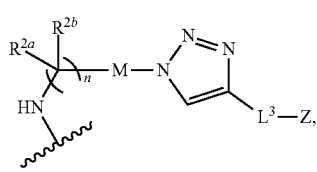

(III)

or a salt thereof, wherein M is a alkyl or aryl, each of which is optionally substituted with one or more $R^3$; $L^3$ is alkyl or heteroalkyl optionally substituted with one or more $R^2$; Z is alkyl, heteroalkyl, cycloalkyl, heterocyclyl, aryl, or heteroaryl, each of which is optionally substituted with one or more $R^5$; each of $R^{2a}$ and $R^{2b}$ is independently hydrogen, alkyl, or heteroalkyl, or $R^{2a}$ and $R^{2b}$ is taken together to form an oxo group; each $R^2$, $R^3$, and $R^5$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; n is independently 1, 2, 3, 4, 5, or 6; and "～～" refers to a connection to an attachment group or the hydrogel-forming polymer.

13. The process of claim 10, wherein the compound of Formula (I) is a compound of Formula (IV):

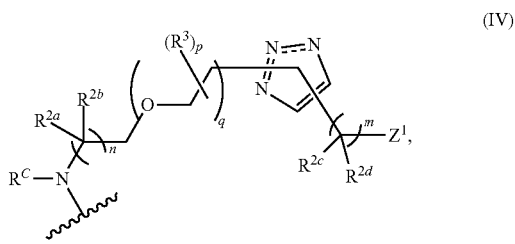

(IV)

or a salt thereof, wherein $Z^1$ is alkyl, alkenyl, alkynyl, heteroalkyl, cycloalkyl, heterocyclyl, aryl, or heteroaryl, each of which is optionally substituted with 1-5 $R^5$; each of $R^{2a}$, $R^{2b}$, $R^{2c}$, and $R^{2d}$ is independently hydrogen, alkyl, alkenyl, alkynyl, heteroalkyl, halo, cyano, nitro, amino, cycloalkyl, heterocyclyl, aryl, or heteroaryl; or $R^{2a}$ and $R^{2b}$ or $R^{2c}$ and $R^{2d}$ are taken together to form an oxo group; $R^C$ is hydrogen, alkyl, alkenyl, wherein each of alkyl and alkenyl is optionally substituted with 1-6 $R^6$; each of $R^3$, $R^5$, and $R^6$ is independently alkyl, heteroalkyl, halogen, oxo, —$OR^{A1}$, —$C(O)OR^{A1}$, or —$C(O)R^{B1}$; each $R^{A1}$ and $R^{B1}$ is independently hydrogen, alkyl, or heteroalkyl; m and n are each independently 1, 2, 3, 4, 5, or 6; q is an integer from 0 to 25; and "～～" refers to a connection to an attachment group or the hydrogel-forming polymer.

14. A process for preparing a hydrogel capsule composition from an alginate polymer solution,
wherein the alginate polymer solution comprises an afibrotic hydrogel-forming alginate polymer and an unmodified hydrogel-forming alginate polymer,
wherein the process comprises contacting a plurality of droplets of the alginate polymer solution with an aqueous cross-linking solution for a period of time sufficient to produce hydrogel capsules,
wherein the cross-linking solution comprises $BaCl_2$, HEPES buffer, mannitol, and poloxamer 188; and
wherein the alginate polymer solution further comprises a cell suspension comprising a plurality of cells.

\* \* \* \* \*

SEQUENCE LISTING

```
<160> NUMBER OF SEQ ID NOS: 2

<210> SEQ ID NO 1
<211> LENGTH: 1457
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
        50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240
```

```
Ala Ala Ser Ala Arg Ala Trp Pro Lys Met His Thr Val Asn Gly Tyr
            245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655
```

```
Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
        740                 745                 750

Asn Asn Ala Ile Glu Pro Arg Ser Phe Ser Gln Asn Pro Pro Val Leu
            755                 760                 765

Lys Arg His Gln Arg Glu Ile Thr Arg Thr Thr Leu Gln Ser Asp Gln
            770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Asn Gln Ser Pro Arg Ser Phe
                805                 810                 815

Gln Lys Lys Thr Arg His Tyr Phe Ile Ala Ala Val Glu Arg Leu Trp
            820                 825                 830

Asp Tyr Gly Met Ser Ser Pro His Val Leu Arg Asn Arg Ala Gln
            835                 840                 845

Ser Gly Ser Val Pro Gln Phe Lys Lys Val Val Phe Gln Glu Phe Thr
850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
                900                 905                 910

Ser Leu Ile Ser Tyr Glu Glu Asp Gln Arg Gln Gly Ala Glu Pro Arg
            915                 920                 925

Lys Asn Phe Val Lys Pro Asn Glu Thr Lys Thr Tyr Phe Trp Lys Val
            930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
            980                 985                 990

Gly Arg Gln Val Thr Val Gln Glu Phe Ala Leu Phe Phe Thr Ile Phe
            995                 1000                1005

Asp Glu Thr Lys Ser Trp Tyr Phe Thr Glu Asn Met Glu Arg Asn
        1010                1015                1020

Cys Arg Ala Pro Cys Asn Ile Gln Met Glu Asp Pro Thr Phe Lys
        1025                1030                1035

Glu Asn Tyr Arg Phe His Ala Ile Asn Gly Tyr Ile Met Asp Thr
        1040                1045                1050

Leu Pro Gly Leu Val Met Ala Gln Asp Gln Arg Ile Arg Trp Tyr
        1055                1060                1065
```

-continued

```
Leu Leu Ser Met Gly Ser Asn Glu Asn Ile His Ser Ile His Phe
    1070            1075            1080

Ser Gly His Val Phe Thr Val Arg Lys Lys Glu Glu Tyr Lys Met
    1085            1090            1095

Ala Leu Tyr Asn Leu Tyr Pro Gly Val Phe Glu Thr Val Glu Met
    1100            1105            1110

Leu Pro Ser Lys Ala Gly Ile Trp Arg Val Glu Cys Leu Ile Gly
    1115            1120            1125

Glu His Leu His Ala Gly Met Ser Thr Leu Phe Leu Val Tyr Ser
    1130            1135            1140

Asn Lys Cys Gln Thr Pro Leu Gly Met Ala Ser Gly His Ile Arg
    1145            1150            1155

Asp Phe Gln Ile Thr Ala Ser Gly Gln Tyr Gly Gln Trp Ala Pro
    1160            1165            1170

Lys Leu Ala Arg Leu His Tyr Ser Gly Ser Ile Asn Ala Trp Ser
    1175            1180            1185

Thr Lys Glu Pro Phe Ser Trp Ile Lys Val Asp Leu Leu Ala Pro
    1190            1195            1200

Met Ile Ile His Gly Ile Lys Thr Gln Gly Ala Arg Gln Lys Phe
    1205            1210            1215

Ser Ser Leu Tyr Ile Ser Gln Phe Ile Ile Met Tyr Ser Leu Asp
    1220            1225            1230

Gly Lys Lys Trp Gln Thr Tyr Arg Gly Asn Ser Thr Gly Thr Leu
    1235            1240            1245

Met Val Phe Phe Gly Asn Val Asp Ser Ser Gly Ile Lys His Asn
    1250            1255            1260

Ile Phe Asn Pro Pro Ile Ile Ala Arg Tyr Ile Arg Leu His Pro
    1265            1270            1275

Thr His Tyr Ser Ile Arg Ser Thr Leu Arg Met Glu Leu Met Gly
    1280            1285            1290

Cys Asp Leu Asn Ser Cys Ser Met Pro Leu Gly Met Glu Ser Lys
    1295            1300            1305

Ala Ile Ser Asp Ala Gln Ile Thr Ala Ser Ser Tyr Phe Thr Asn
    1310            1315            1320

Met Phe Ala Thr Trp Ser Pro Ser Lys Ala Arg Leu His Leu Gln
    1325            1330            1335

Gly Arg Ser Asn Ala Trp Arg Pro Gln Val Asn Asn Pro Lys Glu
    1340            1345            1350

Trp Leu Gln Val Asp Phe Gln Lys Thr Met Lys Val Thr Gly Val
    1355            1360            1365

Thr Thr Gln Gly Val Lys Ser Leu Leu Thr Ser Met Tyr Val Lys
    1370            1375            1380

Glu Phe Leu Ile Ser Ser Ser Gln Asp Gly His Gln Trp Thr Leu
    1385            1390            1395

Phe Phe Gln Asn Gly Lys Val Lys Val Phe Gln Gly Asn Gln Asp
    1400            1405            1410

Ser Phe Thr Pro Val Val Asn Ser Leu Asp Pro Pro Leu Leu Thr
    1415            1420            1425

Arg Tyr Leu Arg Ile His Pro Gln Ser Trp Val His Gln Ile Ala
    1430            1435            1440

Leu Arg Met Glu Val Leu Gly Cys Glu Ala Gln Asp Leu Tyr
    1445            1450            1455
```

```
<210> SEQ ID NO 2
<211> LENGTH: 415
<212> TYPE: PRT
<213> ORGANISM: Homo sapiens

<400> SEQUENCE: 2

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Gly
        35                  40                  45

Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
    130                 135                 140

Arg Ala Glu Thr Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
            180                 185                 190

Pro Trp Gln Val Val Leu Asn Gly Lys Val Asp Ala Phe Cys Gly Gly
        195                 200                 205

Ser Ile Val Asn Glu Lys Trp Ile Val Thr Ala Ala His Cys Val Glu
    210                 215                 220

Thr Gly Val Lys Ile Thr Val Val Ala Gly Glu His Asn Ile Glu Glu
225                 230                 235                 240

Thr Glu His Thr Glu Gln Lys Arg Asn Val Ile Arg Ile Ile Pro His
                245                 250                 255

His Asn Tyr Asn Ala Ala Ile Asn Lys Tyr Asn His Asp Ile Ala Leu
            260                 265                 270

Leu Glu Leu Asp Glu Pro Leu Val Leu Asn Ser Tyr Val Thr Pro Ile
        275                 280                 285

Cys Ile Ala Asp Lys Glu Tyr Thr Asn Ile Phe Leu Lys Phe Gly Ser
    290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Arg Ser Thr Lys Phe Thr Ile Tyr Asn Asn Met Phe Cys Ala Gly
            340                 345                 350

Phe His Glu Gly Gly Arg Asp Ser Cys Gln Gly Asp Ser Gly Gly Pro
        355                 360                 365

His Val Thr Glu Val Glu Gly Thr Ser Phe Leu Thr Gly Ile Ile Ser
    370                 375                 380
```

```
Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr
                405                 410                 415
```